United States Patent
Hunt

(10) Patent No.: US 11,147,878 B2
(45) Date of Patent: *Oct. 19, 2021

(54) ANIMAL PROTEIN-FREE PHARMACEUTICAL COMPOSITIONS

(71) Applicant: Allergan, Inc., Irvine, CA (US)

(72) Inventor: Terrence J. Hunt, Corona, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/322,283

(22) Filed: May 17, 2021

(65) Prior Publication Data

US 2021/0268109 A1 Sep. 2, 2021

Related U.S. Application Data

(63) Continuation of application No. 17/143,770, filed on Jan. 7, 2021, which is a continuation of application No. 17/071,239, filed on Oct. 15, 2020, now Pat. No. 11,033,625, which is a continuation of application No. 16/925,667, filed on Jul. 10, 2020, now abandoned, which is a continuation of application No. 13/427,582, filed on Mar. 22, 2012, now abandoned, which is a continuation of application No. 12/331,816, filed on Dec. 10, 2008, now Pat. No. 8,168,206, which is a continuation of application No. 11/524,683, filed on Sep. 21, 2006, now Pat. No. 8,137,677.

(60) Provisional application No. 60/725,126, filed on Oct. 6, 2005.

(51) Int. Cl.

| | |
|---|---|
| *A61K 47/32* | (2006.01) |
| *A61K 47/10* | (2017.01) |
| *A61K 38/48* | (2006.01) |
| *A61K 9/19* | (2006.01) |
| *A61K 9/00* | (2006.01) |
| *A61K 47/26* | (2006.01) |

(52) U.S. Cl.
CPC ............ *A61K 47/10* (2013.01); *A61K 9/0019* (2013.01); *A61K 9/19* (2013.01); *A61K 38/4893* (2013.01); *A61K 47/26* (2013.01); *A61K 47/32* (2013.01)

(58) Field of Classification Search
CPC ...................................................... A61K 47/10
See application file for complete search history.

(56) References Cited

U.S. PATENT DOCUMENTS

| | | | |
|---|---|---|---|
| 4,201,706 A | 5/1980 | Trager et al. | |
| 4,891,319 A | 1/1990 | Roser | |
| 5,145,871 A | 9/1992 | Cavazza | |
| 5,472,706 A | 12/1995 | Friedman et al. | |
| 5,512,547 A | 4/1996 | Johnson et al. | |
| 5,556,771 A | 9/1996 | Shen | |
| 5,696,077 A | 12/1997 | Johnson et al. | |
| 5,756,468 A | 5/1998 | Johnson et al. | |
| 5,945,098 A | 8/1999 | Sarno | |
| 5,989,545 A | 11/1999 | Foster et al. | |
| 6,087,327 A | 7/2000 | Pearce et al. | |
| 6,306,423 B1 | 10/2001 | Donovan et al. | |
| 6,461,617 B1 | 10/2002 | Shone | |
| 6,585,987 B1 | 7/2003 | Fransoni | |
| 6,632,440 B1 | 10/2003 | Quinn et al. | |
| 6,653,062 B1 | 11/2003 | Depablo | |
| 6,777,196 B2 | 8/2004 | Klein | |
| 6,843,998 B1 | 1/2005 | Steward | |
| 7,132,259 B1 | 11/2006 | Dolly | |
| 7,223,577 B2 | 5/2007 | Steward | |
| 7,354,740 B2 | 4/2008 | Xiang | |
| 7,419,676 B2 | 9/2008 | Dolly et al. | |
| 7,560,100 B2 | 7/2009 | Pinchasi | |
| 7,758,873 B2 | 7/2010 | Hunt | |
| 7,780,967 B2 | 8/2010 | Hunt | |
| 7,829,525 B2 | 11/2010 | Frevert | |
| 7,879,341 B2 | 2/2011 | Taylor | |
| 7,998,489 B2 | 8/2011 | Steward | |
| 8,067,200 B2 | 11/2011 | Foster | |
| 8,137,677 B2 | 3/2012 | Hunt | |
| 8,168,206 B1 | 5/2012 | Hunt | |
| 8,216,591 B2 | 7/2012 | Hunt | |
| 8,322,666 B2 | 12/2012 | Duemmel | |
| 8,372,645 B2 | 2/2013 | Taylor | |
| 8,529,939 B2 | 9/2013 | Masters | |
| 8,580,250 B2 | 11/2013 | Hunt | |
| 8,632,785 B2 | 1/2014 | Hunt | |
| 8,642,047 B2 | 2/2014 | Hunt | |
| 9,044,477 B2 | 6/2015 | Blanda et al. | |
| 9,050,336 B2 | 6/2015 | Blanda et al. | |
| 9,107,815 B2 | 8/2015 | Hunt | |

(Continued)

FOREIGN PATENT DOCUMENTS

| | | |
|---|---|---|
| AU | 2005274822 | 10/2008 |
| CA | 2668417 | 5/2008 |

(Continued)

OTHER PUBLICATIONS

Johnson, Keith A., Preparation of Peptide and Protein Powders for Inhalation, Advance Drup Delivery Reviews, 1997, 26, pp. 3-15, Elsevier, California.

Kedlaya, D., et al., Botulinum Toxin, Medscape, 2019,1-19.

Hunt, T., et al., Potency of the botulinim toxin product CNBTX-A significantly exceeds labeled units in standard potency test, J. Am. Acad. Dermatol. 2008, 58(3): 517-518.

Hunt, T., et al., Reconsistuted onabotulinumtoxinA retains potency and safety under extended refrigerated storage, Abstract Toxins 2013, 68:114 (abstract only).

(Continued)

*Primary Examiner* — Albert M Navarro
(74) *Attorney, Agent, or Firm* — Foley Hoag LLP

(57) ABSTRACT

Animal protein-free, solid-form Clostridial toxin pharmaceutical compositions comprising a Clostridial toxin active ingredient and at least two excipients.

21 Claims, No Drawings

(56) References Cited

U.S. PATENT DOCUMENTS

| | | |
|---|---|---|
| 9,278,140 B2 | 3/2016 | Hunt |
| 9,302,008 B2 | 4/2016 | Hunt |
| 9,629,904 B2 | 4/2017 | Hunt |
| 9,943,576 B2 | 4/2018 | Forssen et al. |
| 10,105,421 B2 | 10/2018 | Taylor |
| 10,369,190 B2 | 8/2019 | Abiad et al. |
| 10,549,042 B2 | 2/2020 | Vogt |
| 10,561,604 B2 | 2/2020 | Webb et al. |
| 11,033,625 B2 | 6/2021 | Hunt |
| 2002/0002185 A1 | 1/2002 | Reed et al. |
| 2002/0037833 A1 | 3/2002 | Donovan |
| 2002/0044968 A1 | 4/2002 | Van |
| 2002/0064536 A1 | 5/2002 | Hunt |
| 2002/0107199 A1 | 8/2002 | Walker |
| 2003/0118598 A1 | 6/2003 | Hunt |
| 2003/0138437 A1* | 7/2003 | Hunt .................. A61K 8/66 424/184.1 |
| 2003/0180289 A1 | 9/2003 | Foster |
| 2004/0009180 A1 | 1/2004 | Donovan |
| 2004/0043374 A1 | 3/2004 | Depablo |
| 2004/0086532 A1* | 5/2004 | Donovan ............... A61P 3/04 424/239.1 |
| 2004/0143213 A1 | 7/2004 | Hunter |
| 2004/0161776 A1 | 8/2004 | Maddon |
| 2004/0204471 A1 | 10/2004 | Seibert |
| 2004/0220386 A1 | 11/2004 | Steward |
| 2005/0147690 A1 | 7/2005 | Masters |
| 2005/0214325 A1 | 9/2005 | David |
| 2006/0002862 A1 | 1/2006 | Truong-le |
| 2006/0018931 A1 | 1/2006 | Taylor |
| 2006/0057165 A1 | 3/2006 | Dimitrakoudis |
| 2006/0073207 A1 | 4/2006 | Masters |
| 2006/0073333 A1 | 4/2006 | Anderson |
| 2006/0211619 A1 | 9/2006 | Steward |
| 2007/0134199 A1 | 6/2007 | Frevert |
| 2007/0166332 A1 | 7/2007 | Steward |
| 2008/0050352 A1 | 2/2008 | Webb et al. |
| 2008/0057575 A1 | 3/2008 | Fernandez-Salas |
| 2008/0096248 A1 | 4/2008 | Steward |
| 2008/0138893 A1 | 6/2008 | Steward |
| 2008/0187960 A1 | 8/2008 | Foster |
| 2008/0241881 A1 | 10/2008 | Steward |
| 2008/0274194 A1 | 11/2008 | Miller |
| 2008/0279896 A1 | 11/2008 | Heinen |
| 2009/0010965 A1 | 1/2009 | Eisele et al. |
| 2009/0025906 A1 | 1/2009 | Huang |
| 2009/0181083 A1 | 7/2009 | Holm |
| 2009/0214685 A1 | 8/2009 | Hunt |
| 2009/0324647 A1 | 12/2009 | Borodic |
| 2010/0158951 A1 | 6/2010 | Randolph |
| 2010/0260796 A1 | 10/2010 | Belin-poput |
| 2011/0091503 A1 | 4/2011 | Taylor |
| 2011/0159047 A1 | 6/2011 | Sullivan |
| 2012/0093866 A1 | 4/2012 | Burger |
| 2012/0122802 A1 | 5/2012 | Hunt |
| 2012/0258126 A1 | 10/2012 | Schoeller |
| 2013/0046275 A1 | 2/2013 | Holzer |
| 2013/0121987 A1 | 5/2013 | Taylor |
| 2013/0203148 A1 | 8/2013 | Steward |
| 2013/0224248 A1 | 8/2013 | Taylor |
| 2015/0352226 A1 | 12/2015 | Hunt |
| 2016/0175410 A1 | 6/2016 | Hunt |
| 2017/0224786 A1 | 8/2017 | Hunt |
| 2018/0015225 A1 | 1/2018 | Vogt |
| 2018/0271959 A1 | 9/2018 | Hunt |
| 2019/0022195 A1 | 1/2019 | Forssen et al. |
| 2019/0247476 A1 | 8/2019 | Abiad et al. |
| 2019/0336691 A1 | 11/2019 | Vogt |
| 2020/0121855 A1 | 4/2020 | Vogt |
| 2020/0330564 A1 | 10/2020 | Hunt |
| 2021/0038720 A1 | 2/2021 | Hunt |

FOREIGN PATENT DOCUMENTS

| | | |
|---|---|---|
| CA | 2532475 | 5/2013 |
| CN | 1215084 | 4/1999 |
| EP | 0436726 | 7/1991 |
| EP | 0778021 | 6/1997 |
| EP | 1112082 | 4/2001 |
| EP | 1253932 | 4/2005 |
| EP | 1994509 B1 | 7/2009 |
| EP | 2248518 | 1/2013 |
| EP | 1931306 B1 | 7/2013 |
| EP | 2679217 B1 | 4/2016 |
| GB | 2419527 | 5/2006 |
| JP | 2763400 | 6/1998 |
| JP | H10203997 | 8/1998 |
| JP | H11507072 | 6/1999 |
| JP | 2001322929 | 11/2001 |
| JP | 2003119115 | 4/2003 |
| JP | 2005527470 | 9/2005 |
| WO | 8404681 | 12/1984 |
| WO | 9735604 | 10/1997 |
| WO | 9841288 A2 | 9/1998 |
| WO | 199841208 A1 | 9/1998 |
| WO | 0101932 | 1/2001 |
| WO | 0137656 A2 | 5/2001 |
| WO | 0158472 A2 | 8/2001 |
| WO | 0137656 A3 | 1/2002 |
| WO | 0158472 A3 | 1/2002 |
| WO | 0193827 | 5/2002 |
| WO | 02038161 | 5/2002 |
| WO | 2003051332 | 1/2003 |
| WO | 2004060384 | 10/2004 |
| WO | 2005007185 A2 | 1/2005 |
| WO | 2005007185 A3 | 5/2005 |
| WO | 2006005910 A2 | 1/2006 |
| WO | 2006-059093 | 6/2006 |
| WO | 2006020208 A3 | 6/2006 |
| WO | 2006005910 A3 | 9/2006 |
| WO | 2007041664 | 4/2007 |
| WO | 2007044809 A2 | 4/2007 |
| WO | 2008079464 A2 | 7/2008 |
| WO | 2010090677 | 8/2010 |
| WO | 2018053004 A2 | 3/2018 |
| WO | 2018053021 A1 | 3/2018 |

OTHER PUBLICATIONS

Parkins, et al., The formulation of biopharmaceutical products, PSTT 2000, 3(4): 129-137.

Roy, et al., Effect of pH on Stability of Recombinant Botulinum Serotype A Vaccine in Aqueous Solution and During Storage of Freeze-Dried Formulations, J. Pharmaceutical Sciences 2008, 97(12): 5132-5146.

Allergan, Inc., Appeal Brief filed Jan. 2, 2019, for U.S. Appl. No. 13/427,582, filed Mar. 22, 2012, in the name of Allergan, Inc., 18 pages.

Allergan, Inc., Appeal Brief filed Jun. 3, 2019, for U.S. Appl. No. 14/139,519, filed Dec. 23, 2013, in the name of Allergan, Inc., 43 pages.

Allergan, Inc., Pre-Appeal Brief filed Jul. 9, 2018, for U.S. Appl. No. 14/139,519, filed Dec. 23, 2013, in the name of Allergan, Inc., 5 pages.

Allergan, Inc., Reply Brief filed Apr. 4, 2019, to Examiner's Answers of Feb. 4, 2019, for U.S. Appl. No. 13/427,582, filed Mar. 22, 2012, in the name of Allergan, Inc., 18 pages.

Allergan, Inc., Reply Brief filed Sep. 30, 2019, to Examiner's Answers of Jul. 31, 2019, for U.S. Appl. No. 14/139,519, filed Dec. 23, 2013, in the name of Allergan, Inc., 20 pages.

United States Patent & Trademark Office, Examiner's Answer dated Feb. 4, 2019, for U.S. Appl. No. 13/427,582, filed Mar. 12, 2012, in the name of Allergan, Inc., 25 pages.

United States Patent & Trademark Office, Examiner's Answer dated Jul. 31, 2019, for U.S. Appl. No. 14/139,519, filed Dec. 23, 2013, in the name of Allergan, Inc., 60 pages.

United States Patent & Trademark Office, Patent Trial & Appeal Board Decision—Examiner decision affirmed, mailed May 12,

(56) References Cited

OTHER PUBLICATIONS 2020, for U.S. Appl. No. 13/427,582, filed Mar. 22, 2012, in the name of Allergan, Inc., 12 pages.
United States Patent & Trademark Office, Patent Trial & Appeal Board Decision—Examiner decision affirmed, mailed May 4, 2020, for U.S. Appl. No. 14/139,519, filed Dec. 23, 2013, in the name of Allergan, Inc., 43 pages.
Allergan, Inc. Response of May 2, 2018, to EPO's preliminary opinion dated Oct. 16, 2017, of EP 2373294, 8 pages.
Allergan, Inc., Formal Appeal dated Nov. 26, 2018, of EP 2373294, 2 pages.
Allergan, Inc., Grounds of Appeal dated Feb. 5, 2019, of EP 2373294, Appeal Case No. T2797/18-3.3.07, 23 pages.
Allergan, Inc., Grounds of Appeal dated Jul. 19, 2019, of EP 2679217, Appeal Case No. T1375/19-3-.3.07, 8 page.
Allergan, Inc., Grounds of Appeal dated Jun. 2, 2020, of EP 1931306, Appeal Case No. T0626/20-3.3.07, 27 pages.
Allergan, Inc., Grounds of Appeal dated Mar. 2, 2016, of EP 1931306, Appeal Case No. T0626/20-3.3.07, 9 pages.
Allergan, Inc., Response of Aug. 14, 2018, to EP Board of Appeal communication of Jul. 3, 2018, of EP 1931306, Appeal Case No. T0626/20-3.3.07, 5 pages.
Allergan, Inc., Response of Dec. 15, 2014, to EP communication Rule 79(1) dated Jun. 5, 2014, 2015, of EP 1931306, Appeal Case No. T0626/20-3.3.07, 13 pages.
Allergan, Inc., Response of Dec. 3, 2019, to Opponent's (Ipsen Pharma S.A.S.) submission of Jul. 19, 2017, of EP 2679217, Appeal Case No. t1375/19-3.3.07, 27 pages.
Allergan, Inc., Response of Jul. 10, 2017, to EPO's Notice of Opposition of Feb. 28, 2017, of EP 2373294, 6 pages.
Allergan, Inc., Response of Jul. 19, 2019, to summons of Jan. 28, 2019, of EP 1 931 306, Appeal Case No. T0626/20-3.3.07, 6 pages.
Allergan, Inc., Response of Jun. 26, 2017, to EP Board of Appeal communication of Feb. 14, 2017, of EP 2679217, Appeal Case No. T1375/19-3.3.07, 5 pages.
Allergan, Inc., Response of Nov. 28, 2018, to Opponent's (Ipsen Pharma S.A.S.) submission of Oct. 16, 2018,of EP 2679217, Appeal Case No. T0626/20-3.3.07, 9 pages.
Allergan, Inc., Response of Nov. 5, 2019, to Ipsen's submission dated Oct. 14, 2019, of EP 1931306Appeal Case No. T0626/20-3. 3.07, 16 pages.
Allergan, Inc., Response of Oct. 2, 2015, to Opponent's (Ipsen Pharma S.A.S.) late submission, of EP 1931306, Appeal Case No. T0626/20-3.3.07, 2 pages.
Allergan, Inc., Response of Oct. 6, 2015, to EP Opposition Division's oral hearing schedule release, of EP 1931306, Appeal Case No. T0626/20-3.3.07, 26 pages.
Allergan, Inc., Response of Sep. 7, 2015, to summons to attend oral hearing dated Feb. 24, 2015, of EP 1931306, Appeal Case No. T0626/20-3.3.07, 166 pages.
Ansel, Howard, Pharmaceutical Dosage Forms and Drug Delivery Systems, 1999, 2 Pages, 7th edition, Lippincott Williams & Wilkins.
Bradshaw, M. et al., Regulation of neurotoxin complex expression in Clostridium botulinum strains 62A, Hall A-hyper, and NCTC 2916, Anaerobe, 2004, 321-333, 10.
Carpenter, J., et al. Formulation and Delivery of Protein and Peptides, vol. 567: 134-147, 2004.
Depiereux, Eric et al, Match-Box: A Fundamentally New Algorithm for the Simultaneous Alignment of Several Protein Sequences, CABIOS, 1992, 501-509, 8 (5), US.
Edgar, Robert, Muscle: Multiple Sequence Alignment with High Accuracy and High Throughput, Nucleic Acids Research, 2004, 1792-1797, 32(5).
European Patent Office, Appeal Decision dated Nov. 8, 2018, of EP 1931306, Appeal Case No. T0626/20-3.3.07, 19 pages.
European Patent Office, Board of Appeal preliminary opinion, dated Apr. 4, 2018, of EP 2679217, Appeal Case No. T1375/19-3.3.07, 17 pages.
European Patent Office, Board of Appeal preliminary opinion, dated Jul. 3, 2018, of EP 1931306, Appeal Case No. T0626/20-3.3.07, 19 pages.
European Patent Office, Board of Appeals minutes dated Mar. 12, 2019, of EP 2679217, Appeal Case No. T1375/19-3.3.07, 14 pages.
European Patent Office, Board of Appeals minutes dated Sep. 17, 2018, of EP 1931306, Appeal Case No. T0626/20-3.3.07, 3 pages.
European Patent Office, minutes from Oral Proceedings of Jul. 3, 2018, of EP 2373294, dated Sep. 25, 2018, 6 pages.
European Patent Office, minutes from Oral Proceedings of Oct. 12, 2019, of EP 1931306, dated Jan. 23, 2020, 35 pages.
European Patent Office, minutes from Oral Proceedings of Oct. 7, 2015, of EP 1931306, dated Oct. 23, 2015, 15 pages.
European Patent Office, Decision Revoking EP 1931306 dated Oct. 23, 2015, 14 pages.
European Patent Office, Decision Revoking EP 2373294 dated Sep. 25, 2018, 15 pages.
European Patent Office, Fax to Allergan, Inc., dated Oct. 5, 2015, oral proceedings date is maintained, of EP 1931306, 4 pages.
European Patent Office, Interlocutory decision dated Jan. 23, 2020, in opposition proceedings of EP 1931306, 20 pages.
European Patent Office, Interlocutory decision dated Mar. 12, 2019, in opposition proceedings of EP 2679217, 29 pages.
European Patent Office, Preliminary Opinion of Feb. 24, 2015, for EP1931306, 10 pages.
European Patent Office, Preliminary Opinion of Oct. 16, 2017, of EP 2373294, 7 pages.
European Patent Office, Summons of Jan. 28, 2019, to attend Oral Proceedings, of EP 1931306, 11 pages.
Goodnough, M., et al., Stabilization of Botulinum Toxin Type A during Lyophilization, Applied and Environmental Microbiology, 1992, 3426-3428, 58 (10).
Goodnough, MC et al, Recovery of type-A botulinal toxin following lyophilization, ACS Symposium Series, 1994, 193-203, 567.
Gotoh, Osamu, Significant Improvement in Accuracy of Multiple Protein Sequence Alignments by Iterative Refinement as Assessed by Reference to Structural Alignments, J. Mol. Biol., 1996, 823-838, 264, US.
Humeau, Yann et al, How Botulinum and Tetanus Neurotoxins Block Neurotransmitter Release, Biochimie, 2000, 427-446, 82.
Ipsen Pharma S.A.S, Notice of Opposition filed Apr. 29, 2014, against EP 1931306, 9 pages.
Ipsen Pharma S.A.S, Notice of Opposition filed Dec. 10, 2009, against EP 2373294, 8 pages.
Ipsen Pharma S.A.S, Notice of Opposition filed Oct. 4, 2006, against EP 2679217, 9 pages.
Ipsen Pharma S.A.S, Response of Aug. 14, 2018, to summons to attend Sep. 11, 2018 hearing, of EP 1931306, Appeal Case No. T0626/20-3.3.07, 2 pages.
Ipsen Pharma S.A.S, Response of Dec. 2, 2019, to Allergan, Inc.'s Grounds of Appeal dated Jul. 19, 2019, of EP 2679217, Appeal Case No. T1375/19-3.3.07, 15 pages.
Ipsen Pharma S.A.S, Response of Jul. 5, 2016, to Allergan, Inc.'s ground of appeal dated Mar. 2, 2016, of EP 1931306, Appeal Case No. T0626/20-3.3.07, 13 pages.
Ipsen Pharma S.A.S, Response of Jun. 3, 2019, to Allergan, Inc.'s Grounds of Appeal dated Feb. 5, 2019, of EP 2373294, Appeal Case No. T2797/18-3.3.07, 18 pages.
Ipsen Pharma S.A.S, Response of Jun. 4, 2018, to Allergan, Inc.'s letter dated May 2, 2018, of EP 2373294, 3 pages.
Ipsen Pharma S.A.S, Response of May 10, 2019, to Decision of the Opposition dated Mar. 12, 2019, of EP 2679217, Appeal Case No. T1375/19-3.3.07, 1 page.
Ipsen Pharma S.A.S, Submision of Sep. 23, 2015, of EP 1931306, Appeal Case No. T0626/20-3.3.07, 3 pages.
Ipsen Pharma S.A.S, Written submission dated Jul. 19, 2019, for EP 2679217, 19 pages.
Ipsen Pharma S.A.S, Written submission dated Oct. 16, 2018, of EP 2679217,13 pages.
Ipsen Pharma S.A.S, Written submissions dated Oct. 8, 2019, of EP 1931306, 9 pages.

(56) References Cited

OTHER PUBLICATIONS

Johnson, Eric, Clostridial botulinum and its Neurotoxins: A Metabolic and Cellular Perspective, Toxicon, 2001, 1703-1722, vol. 39, issue 11.

Kohl, et al., Comparison of the effect of botulinnm toxin A (Botox (R)) with the highly-purified neurotoxin (NT 201) in the extensor digitorum brevis muscle test, Poster Sessions E & F, 2000, 165, P687-P968.

Lalli, Giovanna et al, The Journey of Tetanus and Botulinum Neurotoxins in Neurons, Trends in Microbiology, Sep. 2003, 431-437, 11 (9), US.

Lawrence, Charles et al, Detecting Subtle Sequence Signals: A Gibbs Sampling Strategy for Multiple Alignment, Science, Oct. 8, 1993, 208-214, 262 (5131), US.

Lipham, William, Cosmetic and Clinical Applications of Botulinum Toxin, Slack, 2004, 2 pages, 1.

Morgenstern, Burkhard et al, Multiple DNA and Protein Sequence Alignment Based on Segment-to-Segment Comparison, Proc Natl Acad Sci, Oct. 1996, 12098-12103, 93.

Naumann, M., et al., Botulinum toxin type A (Botox (R)) with the highly-purified neurotxin (NT 201) in the extensor digitorum brevis muscle test, Mv. Disord., 1999, S111-115, Supp 4.

Nizai, S., Handbook of Pharmaceutical Manufacturing Formulations Liquid Products, vol. 3, 2004, p. 58.

Notredame, Cedric et al, T-Coffee: A Novel Method for Fast and Accurate Multiple Sequence Alignment, J. Mol. Biol., 2000, 205-217, 302, US.

Panicker, JN et al., Botulinum toxins: Pharmacology and its current therapeutic evidence for use, Neurology India, 2003, 455-460, 51(4).

Parish, J., Commercial preparations and handling of botulinum toxin type A and type B, Clinics in Dermatology, 2003, 481-484, 21.

Pickar, G., Dosage Calculations, 2004, 3 pages, 7th Ed., Thomson DelMar Learning.

Raffestin, Siephanie et al, Organization and Regulation of the Neurotoxin Genes in Clostridium botulinum and Clostridium tetani, Anaerobe, 2004, 93-100,10.

Ragona, Rosario Marchese et al, Management of Parotid Sialocele With Botulinum Toxin, Laryngoscope, 1999, 1344-1346, 109(8).

Remington, The Science and Practice of Pharmacy, 20th ed. at 831 (2000).

Schantz, E. J., et al., Properties and use of Botulin toxin and other microbial neurotoxins in medicine, Microbial Rev., 1992, 80-99, 56.

Schantz, Edward et al, Preparation And Characterization Of Botulinum Toxin Type A For Human Treatment, Neurological Disease And Therarpy, 1994, 41-49, 25, US.

Singh, B.R., Critical Aspects of Bacterial Protein Toxins, pp. 63-84 (chapter 4) of Natural Toxins II, edited by B.R. Singh et al., Plenum Press, New York (1976).

Subramanian, Amarendran et al, DIALIGN-T: An Improved Algorithm for Segment-Based Multiple Sequence Alignment, BMC Bioinformatics, 2005, 13 Pages, 6(66).

Thompson, Julie et al, CLUSTAL W: Improving the Sensitivity of Progressive Multiple Sequence Alignment Through Sequence Weighting, Position-Specific Gap Penalties and Weight Matrix Choice, Nucleic Acids Research, 1994, 4673-4680, 22(22).

Tuton, Kathryn et al, Botulinum and Tetanus Neurotoxins: Structure, Function and Therapeutic Utility, Trends in Biochemical Sciences, Nov. 2002, 552-558, 27(11).

Walle, Ivo et al, Align-m A New Algorithm for Multiple Alignment of Highly Divergent Sequences, Bioinformatics, 2004, 1428-1435, 20 (9), US.

* cited by examiner

ANIMAL PROTEIN-FREE PHARMACEUTICAL COMPOSITIONS

This application is a continuation of U.S. patent application Ser. No. 17/143,770, filed Jan. 7, 2021, which is a continuation of U.S. patent application Ser. No. 17/071,239, filed Oct. 15, 2020, which is a continuation of U.S. patent application Ser. No. 16/925,667, filed Jul. 10, 2020, now abandoned, which is a continuation of U.S. application Ser. No. 13/427,582, filed Mar. 22, 2012, now abandoned, which is a continuation of U.S. patent application Ser. No. 12/331,816, filed Dec. 10, 2008, now U.S. Pat. No. 8,168,206, issued May 1, 2012, which is a continuation-in-part that claims priority pursuant to 35 U.S.C. § 120 to U.S. patent application Ser. No. 11/524,683, filed Sep. 21, 2006, now U.S. Pat. No. 8,137,677, issued Mar. 20, 2012, which claims priority pursuant to 35 U.S.C. § 119(e) to U.S. Provisional Application No. 60/725,126, filed Oct. 6, 2005, each of which is hereby incorporated by reference in its entirety.

A pharmaceutical composition is a formulation comprises at least one active ingredient and at least one inert ingredient, called an excipient, used as a diluent or vehicle for the active ingredient. An excipient is useful in one or more of the following as a stabilizing agent, a bulking agent, a cryo-protectant, a lyo-protectant, a preservative, and a buffer. A pharmaceutical composition can be processed into a solid form, such as, e.g., a lyophilized (freeze dried), or vacuum dried powder which can be reconstituted with a suitable fluid, such as saline or water, prior to administration to a patient. Alternately, a pharmaceutical composition can be formulated as an aqueous solution or suspension.

The vast majority of pharmaceutical compositions include a small molecule (or chemical entity) as their active ingredient. Recently, with the advent of the biotechnology industry, pharmaceutical compositions comprising a protein active ingredient have been, or are currently being, developed. Unfortunately, a protein active ingredient can be very difficult to stabilize (i.e., maintained in a state where loss of biological activity is minimized), thereby resulting in a loss of protein and/or loss of protein activity during the formulation, reconstitution (if required) and storage of the pharmaceutical composition prior to use. Stability problems can arise due to surface adsorption of a protein active ingredient, physical instability, such as, e.g., denaturation or aggregation, or chemical instability, such as, e.g., cross-linking, deamidation, isomerization, oxidation, formation of acidic or basic species, Maillard reaction, and fragmentation. To prevent such instability, various protein-based excipients, such as albumin and gelatin, have been used to stabilize a protein active ingredient present in a pharmaceutical composition.

Unfortunately, despite their known stabilizing effects, significant drawbacks exist to the use of protein excipients, such as albumin or gelatin, in a pharmaceutical composition. For example albumin and gelatin are expensive and increasingly difficult to obtain. Furthermore, blood products or animal derived products such as albumin and gelatin, when administered to a patient can subject the patient to a potential risk of receiving blood borne pathogens or infectious agents. Thus, it is known that the possibility exists that the presence of an animal-derived protein excipients in a pharmaceutical composition can result in inadvertent incorporation of infectious elements into the pharmaceutical composition. For example, it has been reported that use of human serum albumin may transmit prions into a pharmaceutical composition. Thus, it is desirable to find a suitable non-protein excipients, such as, e.g., stabilizers, cryo-protectants and lyo-protectants, which can be used to stabilize the protein active ingredient present in a pharmaceutical composition.

The unique characteristics of Clostridial toxins further constrain and hinder the selection of suitable non-protein excipients for a pharmaceutical composition comprising a Clostridial toxin active ingredient. For example, Clostridial toxins are large proteins having an average molecular weight of approximately 150 kDa, and are further complexed with non-toxin associated proteins that increase the size to approximately 300-900-kDa. The size of a Clostridial toxin complex makes it much more fragile and labile than smaller, less complex proteins, thereby compounding the formulation and handling difficulties if Clostridial toxin stability is to be maintained. Hence, the use of non-protein excipients, such as, e.g., stabilizers, cryo-protectants and lyo-protectants must be able to interact with the Clostridial toxin active ingredient in a manner which does not denature, fragment or otherwise inactivate the toxin or cause disassociation of the non-toxin associated proteins present in the toxin complex.

Another problem associated with a Clostridial toxin active ingredient, is the exceptional safety, precision, and accuracy that is necessary for at all steps of the formulation process. Thus, a non-protein excipient should not itself be toxic or difficult to handle so as to not exacerbate the already extremely stringent requirements currently in place to formulate a pharmaceutical composition comprising a Clostridial toxin active ingredient.

Still another difficulty linked with a Clostridial toxin active ingredient, is the incredible low amounts of Clostridial toxin that is used in a pharmaceutical composition. As with enzymes generally, the biological activities of the Clostridial toxins are dependant, at least in part, upon their three dimensional conformation. Thus, a Clostridial toxin is detoxified by heat, various chemicals, surface stretching, and surface drying. Additionally, it is known that dilution of a Clostridial toxin complex obtained by the known culturing, fermentation and purification methods to the much lower concentration used in a pharmaceutical composition results in rapid inactivation of the toxin. The extremely low amount of a Clostridial toxin active ingredient that is used in a pharmaceutical composition, makes this active ingredient very susceptible to adsorption to, e.g., the surfaces of laboratory glassware, vessels, to the vial in which the pharmaceutical composition is reconstituted and to the inside surface of a syringe used to inject the pharmaceutical composition. Such adsorption of a Clostridial toxin active ingredient to surfaces can lead to a loss of active ingredient and to denaturation of the remaining Clostridial toxin active ingredient, both of which reduce the total activity of the active ingredient present in the pharmaceutical composition. Hence, the use of non-protein excipients, such as, e.g., stabilizers, cryo-protectants and lyo-protectants must be able to act as surface blockers to prevent the adsorption of a Clostridial toxin active ingredient to a surface. To date, the only successful stabilizing agent for this purpose has been the animal derived proteins, such as, e.g., human serum albumin and gelatin.

Yet another problem connected to a Clostridial toxin active ingredient, is the pH-sensitivity associates with complex formation. For example, the 900-kDa BoNT/A complex is known to be soluble in dilute aqueous solutions at pH 3.5-6.8. However, at a pH above about 7 the non-toxic associated proteins dissociate from the 150-kDa neurotoxin, resulting in a loss of toxicity, particularly as the pH rises above pH 8.0. See Edward J. Schantz et al., pp. 44-45, *Preparation and characterization of botulinum toxin type A*

*for human treatment*, in Jankovic, J., et al., THERAPY WITH BOTULINUM TOXIN (Marcel Dekker, Inc., 1994). As the non-toxic associated proteins are believed to preserve or help stabilize the secondary and tertiary structures upon which toxicity is depends, the dissociation of these proteins results in a more unstable Clostridial toxin active ingredient. Thus, non-protein excipients useful to formulate a pharmaceutical composition comprising a Clostridial toxin active ingredient must be able to operate within the confines of a pH level necessary to maintain the activity a Clostridial toxin active ingredient.

In light of the unique nature of Clostridial toxins and the requirements set forth above, the probability of finding suitable non-protein excipients useful to formulate a pharmaceutical composition comprising a Clostridial toxin active ingredient has been difficult. Prior to the present invention, only animal derived protein excipients, such as, e.g., human serum albumin and gelatin, were used successfully as stabilizers. Thus, albumin, by itself or with one or more additional substances such as sodium phosphate or sodium citrate, is known to permit high recovery of toxicity of botulinum toxin type A after lyophilization. Unfortunately, as already set forth, human serum albumin, as a pooled blood product, can, at least potentially, carry infectious or disease causing elements when present in a pharmaceutical composition. Indeed, any animal product or protein such as human serum albumin or gelatin can also potentially contain pyrogens or other substances that can cause adverse reactions upon injection into a patient.

What is needed therefore is a Clostridial toxin pharmaceutical compositions wherein the Clostridial toxin (such as a botulinum toxin) is stabilized by a non-protein excipient. The present invention relates to Clostridial toxin pharmaceutical compositions with one or more non-protein excipients which functions to stabilize the Clostridial toxin present in the pharmaceutical composition.

Thus, in an aspect of the present invention, a Clostridial toxin pharmaceutical composition comprises an animal protein-free excipient and a Clostridial toxin active ingredient. In another aspect, a Clostridial toxin pharmaceutical composition comprises at least two an animal protein-free excipients and a Clostridial toxin active ingredient. In yet another aspect, a Clostridial toxin pharmaceutical composition comprises at least three an animal protein-free excipients and a Clostridial toxin active ingredient. A Clostridial toxin active ingredient can be a Clostridial toxin complex comprising the approximately 150-kDa Clostridial toxin and other proteins collectively called non-toxin associated proteins (NAPs), the approximately 150-kDa Clostridial toxin alone, or a modified Clostridial toxin, such as, e.g., a re-targeted Clostridial toxin.

Thus, in an aspect of the present invention, a Clostridial toxin pharmaceutical composition comprises a non-protein-based excipient and a Clostridial toxin active ingredient. In another aspect, a Clostridial toxin pharmaceutical composition comprises at least two non-protein-based excipients and a Clostridial toxin active ingredient. In yet another aspect, a Clostridial toxin pharmaceutical composition comprises at least three non-protein-based excipients and a Clostridial toxin active ingredient. A Clostridial toxin active ingredient can be a Clostridial toxin complex comprising the approximately 150-kDa Clostridial toxin and other proteins collectively called non-toxin associated proteins (NAPs), the approximately 150-kDa Clostridial toxin alone, or a modified Clostridial toxin, such as, e.g., a re-targeted Clostridial toxin.

In another aspect of the present invention, a Botulinum toxin pharmaceutical composition comprises an animal protein-free excipient and a Botulinum toxin active ingredient. In another aspect, a Botulinum toxin pharmaceutical composition comprises at least two animal protein-free excipients and a Botulinum toxin active ingredient. In yet another aspect, a Botulinum toxin pharmaceutical composition comprises at least three animal protein-free excipients and a Botulinum toxin active ingredient. A Botulinum toxin active ingredient can be a Botulinum toxin complex comprising the approximately 150-kDa botulinum toxin and NAPs, the 150-kDa Botulinum toxin alone, or a modified Botulinum toxin, such as, e.g., a re-targeted botulinum toxin.

In another aspect of the present invention, a Botulinum toxin pharmaceutical composition comprises a non-protein-based excipient and a Botulinum toxin active ingredient. In another aspect, a Botulinum toxin pharmaceutical composition comprises at least two non-protein-based excipients and a Botulinum toxin active ingredient. In yet another aspect, a Botulinum toxin pharmaceutical composition comprises at least three non-protein-based excipients and a Botulinum toxin active ingredient. A Botulinum toxin active ingredient can be a Botulinum toxin complex comprising the approximately 150-kDa botulinum toxin and NAPs, the 150-kDa Botulinum toxin alone, or a modified Botulinum toxin, such as, e.g., a re-targeted botulinum toxin.

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and/F), animals (BoNT/C, and/D), or isolated from soil (BoNT/G). BoNTs possess approximately 35% amino acid identity with each other and share the same functional domain organization and overall structural architecture. It is recognized by those of skill in the art that within each type of Clostridial toxin there can be subtypes that differ somewhat in their amino acid sequence, and also in the nucleic acids encoding these proteins. For example, there are presently five BoNT/A subtypes, BoNT/A1, BoNT/A2, BoNT/A3, BoNT/A4 and BoNT/A5, with specific subtypes showing approximately 89% amino acid identity when compared to another BoNT/A subtype. While all seven BoNT serotypes have similar structure and pharmacological properties, each also displays heterogeneous bacteriological characteristics. In contrast, tetanus toxin (TeNT) is produced by a uniform group of *C. tetani*. Two other species of Clostridia, *C. baratii* and *C. butyricum*, also produce toxins, BaNT and BuNT respectively, which are similar to BoNT/F and BoNT/E, respectively.

Clostridial toxins are released by Clostridial bacterium as complexes comprising the approximately 150-kDa Clostridial toxin along with associated non-toxin proteins (NAPs). Identified NAPs include proteins possessing hemagglutination activity, such as, e.g., a hemagglutinin of approximately 17-kDa (HA-17), a hemagglutinin of approximately 33-kDa (HA-33) and a hemagglutinin of approximately 70-kDa (HA-70); as well as non-toxic non-hemagglutinin (NTNH), a protein of approximately 130-kDa, see, e.g., Eric A. Johnson and Marite Bradshaw, *Clostridial botulinum and its Neurotoxins: A Metabolic and Cellular Perspective*, 39 Toxicon 1703-1722 (2001); and Stephanie Raffestin et al., *Organization and Regulation of the Neurotoxin Genes in Clostridium botulinum and Clostridium tetani*, 10 Anaerobe 93-100 (2004). Thus, the botulinum toxin type A complex can be produced by Clostridial bacterium as 900-kDa, 500-kDa and 300-kDa forms. Botulinum toxin types B and $C_1$ are apparently produced as only a 500-kDa complex. Botulinum toxin type D is produced as both 300-kDa and 500-kDa complexes. Finally, botulinum toxin types E and F are produced as only approximately 300-kDa complexes. The differences in molecular weight for the complexes are due to differing ratios of NAPs. The toxin complex is important for the intoxication process because it provides protection from adverse environmental conditions, resistance to protease digestion, and appears to facilitate internalization and activation of the toxin.

Clostridial toxins are each translated as a single chain polypeptide that is subsequently cleaved by proteolytic scission within a disulfide loop by a naturally-occurring protease. This cleavage occurs within the discrete di-chain loop region created between two cysteine residues that form a disulfide bridge. This posttranslational processing yields a di-chain molecule comprising an approximately 50 kDa light chain (LC) and an approximately 100 kDa heavy chain (HC) held together by the single disulfide bond and non-covalent interactions between the two chains. The naturally-occurring protease used to convert the single chain molecule into the di-chain is currently not known. In some serotypes, such as, e.g., BoNT/A, the naturally-occurring protease is produced endogenously by the bacteria serotype and cleavage occurs within the cell before the toxin is release into the environment. However, in other serotypes, such as, e.g., BoNT/E, the bacterial strain appears not to produce an endogenous protease capable of converting the single chain form of the toxin into the di-chain form. In these situations, the toxin is released from the cell as a single-chain toxin which is subsequently converted into the di-chain form by a naturally-occurring protease found in the environment.

TABLE 1

Clostridial Toxin Reference Sequences and Regions

| Toxin | LC | $H_N$ | $H_C$ | |
|---|---|---|---|---|
| | | | $H_{CN}$ | $H_{CC}$ |
| BoNT/A | M1-K448 | A449-I873 | I874-P1110 | Y1111-L1296 |
| BoNT/B | M1-K441 | A442-I860 | L861-E1097 | Y1098-E1291 |
| BoNT/C1 | M1-K449 | T450-I868 | N869-E1111 | Y1112-E1291 |
| BoNT/D | M1-R445 | D446-I864 | N865-E1098 | Y1099-E1276 |
| BoNT/E | M1-R422 | K423-I847 | K848-E1085 | Y1086-K1252 |
| BoNT/F | M1-K439 | A440-I866 | K867-K1105 | Y1106-E1274 |
| BoNT/G | M1-K446 | S447-I865 | S866-Q1105 | Y1106-E1297 |
| TeNT | M1-A457 | S458-L881 | K882-E1127 | Y1128-D1315 |
| BaNT | M1-K431 | N432-I857 | I858-K1094 | Y1095-E1268 |
| BuNT | M1-R422 | K423-I847 | K848-E1085 | Y1086-E1251 |

Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC ($H_N$) that facilitates release of the LC from intracellular vesicles into the cytoplasm of the target cell; and 3) a binding domain found within the carboxyl-terminal half of the HC ($H_C$) that determines the binding activity and binding specificity of the toxin to the receptor complex located at the surface of the target cell. The $H_C$ domain comprises two distinct structural features of roughly equal size that indicate function and are designated the $H_CN$ and $H_{CC}$ subdomains. Table 1 gives approximate boundary regions for each domain and subdomain found in exemplary Clostridial toxins.

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of type. Although the applicants have no wish to be limited by the following description, the intoxication mechanism can be described as comprising at least four steps: 1) receptor binding, 2) complex internalization, 3) light chain translocation, and 4) enzymatic target modification. The process is initiated when the $H_C$ domain of a Clostridial toxin binds to a toxin-specific receptor complex located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain endopeptidase of the toxin is released from the intracellular vesicle into the cytosol where it specifically targets one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. BuNT cleaves at conserved portion of SNAP-25 near the carboxyl-terminus. The botulinum serotypes BoNT/B, BoNT/D, BoNT/F and BoNT/G, TeNT, and BaNT act on the conserved central portion of VAMP, and release the amino-terminal portion of VAMP into the cytosol. BoNT/C, cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem. Sci. 552-558. (2002); Giovanna Lalli et al., *The Journey of Tetanus and Botulinum Neurotoxins in Neurons*, 11(9) Trends Microbiol. 431-437, (2003).

The ability of Clostridial toxins, such as, e.g., BoNT/A, BoNT/B, BoNT/$C_1$, BoNT/D, BoNT/E, BoNT/F and BoNT/G, TeNT, BaNT and BuNT to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). Clostridial toxins commercially available as pharmaceutical compositions include, BoNT/A preparations, such as, e.g., BOTOX® (Allergan, Inc., Irvine, Calif.), Dysport®/Reloxin®, (Beaufour Ipsen, Porton Down, England), Neuronox® (Medy-Tox, Inc., Ochang-myeon, South Korea), BTX-A (Lanzhou Institute Biological Products, China) and Xeomin® (Merz Pharmaceuticals, GmbH., Frankfurt, Germany); and BoNT/B preparations, such as, e.g., MyoBloc™/NeuroBloc™ (Solstice Neurosciences, Inc., South San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

Aspects of the present pharmaceutical compositions provide, in part, a Clostridial toxin pharmaceutical composition. As used herein, the term "Clostridial toxin pharmaceutical composition" refers to a formulation in which an active ingredient is a Clostridial toxin. As used herein, the term "formulation" means that there is at least one additional ingredient in the pharmaceutical composition besides a Clostridial toxin active ingredient. A pharmaceutical composition is therefore a formulation which is suitable for diagnostic or therapeutic administration to a subject, such as a human patient. The pharmaceutical composition can be a solid formulation, such as, e.g., lyophilized (freeze-dried) or vacuum dried condition, or an aqueous formulation. The constituent ingredients of a pharmaceutical composition can be included in a single composition (that is all the constituent ingredients, except for any required reconstitution fluid, are present at the time of initial compounding of the pharmaceutical composition) or as a two-component system, for example a vacuum-dried composition reconstituted with a diluent such as saline which diluent contains an ingredient not present in the initial compounding of the pharmaceutical composition. A two-component system provides the benefit of allowing incorporation of ingredients which are not sufficiently compatible for long-term shelf storage with the first component of the two component system. For example, the reconstitution vehicle or diluent may include a preservative which provides sufficient protection against microbial growth for the use period, for example one-week of refrigerated storage, but is not present during the two-year freezer storage period during which time it might degrade the toxin. Other ingredients, which may not be compatible with a Clostridial toxin active ingredient or other ingredients for long periods of time, may be incorporated in this manner; that is, added in a second vehicle (i.e. in the reconstitution fluid) at the approximate time of use.

Aspects of the present pharmaceutical compositions provide, in part, animal protein-free. Clostridial toxin pharmaceutical composition. As used herein, the term "animal protein-free" refers to the absence of blood-derived, blood-pooled and other animal-derived products or compounds. As used herein, the term "animal" refers to a mammal, bird, amphibian, reptile, fish, arthropod, or other animal species. "Animal" excludes plants and microorganisms, such as, e.g., yeast and bacteria. For example, an animal protein-free pharmaceutical composition can be a pharmaceutical composition which is either substantially free or essentially free or entirely free of a serum derived albumin, gelatin and other animal-derived proteins, such as, e.g., immunoglobulins. As used herein, the term "entirely free" (or "consisting of" terminology) means that within the detection range of the instrument or process being used, the substance cannot be detected or its presence cannot be confirmed. As used herein, the term "essentially free" (or "consisting essentially of") means that only trace amounts of the substance can be detected. As used herein, the term "substantially free" means present at a level of less than one percent by weight of the pharmaceutical composition. As used herein, the term "animal-derived" refers to any compounds or products purified directly from an animal source. As such, an animal protein recombinantly produced from a microorganism is excluded from the term "animal-derived product or compound." Thus, animal protein-free Clostridial toxin pharmaceutical compositions can include any of the Clostridial neurotoxin active ingredients disclosed in the present specification. As a non-limiting example of an animal protein-free Clostridial toxin pharmaceutical composition is a pharmaceutical composition comprising a BoNT/A toxin as the active ingredient and a suitable sugar and surfactant as excipients. As another non-limiting example of an animal protein-free Clostridial toxin pharmaceutical composition is a pharmaceutical composition comprising a 900-kDa BoNT/A toxin complex as the active ingredient and a suitable sugar and surfactant as excipients. As yet another non-limiting example of an animal protein-free Clostridial toxin pharmaceutical composition is a pharmaceutical composition comprising a modified BoNT/A toxin including an additional di-leucine motif as the active ingredient and a suitable sugar and surfactant as excipients. As still another non-limiting example of an animal protein-free Clostridial toxin pharmaceutical composition is a pharmaceutical composition comprising a re-targeted BoNT/A including an opioid peptide targeting moiety as the active ingredient and a suitable sugar and surfactant as excipients.

Aspects of the present pharmaceutical compositions provide, in part, a Clostridial toxin active ingredient. As used herein, the term "Clostridial toxin active ingredient" refers to a therapeutically effective concentration of a Clostridial toxin active ingredient, such as, e.g., a Clostridial toxin complex, a Clostridial toxin, a modified Clostridial toxin, or a re-targeted Clostridial toxin. As used herein, the term "therapeutically effective concentration" is synonymous with "therapeutically effective amount," "effective amount," "effective dose," "therapeutically effective dose" and refers to the minimum dose of a Clostridial toxin active ingredient necessary to achieve the desired therapeutic effect and includes a dose sufficient to reduce a symptom associated with aliment being treated. In aspects of this embodiment, a therapeutically effective concentration of a Clostridial toxin active ingredient reduces a symptom associated with the aliment being treated by, e.g., at least 10%, at least 20%, at least 30%, at least 40%, at least 50%, at least 60%, at least 70%, at least 80%, at least 90% or at least 100%. In other aspects of this embodiment, a therapeutically effective concentration of a Clostridial toxin active ingredient reduces a symptom associated with the aliment being treated by, e.g., at most 10%, at most 20%, at most 30%, at most 40%, at most 50%, at most 60%, at most 70%, at most 80%, at most 90% or at most 100%.

It is envisioned that any amount of Clostridial toxin active ingredient can be added in formulating a Clostridial toxin pharmaceutical compositions disclosed in the present specification, with the proviso that a therapeutically effective amount of Clostridial toxin active ingredient is recoverable. In aspects of this embodiment, the amount of Clostridial toxin active ingredient added to the formulation is at least 0.001 U/kg, at least 0.01 U/kg, at least 0.1 U/kg, at least 1.0 U/kg, at least 10 U/kg, at least 100 U/kg, or at least 1000 U/kg. In other aspects of this embodiment, the amount of Clostridial toxin active ingredient added to the formulation is at most 0.001 U/kg, at most 0.01 U/kg, at most 0.1 U/kg, at most 1.0 U/kg, at most 10 U/kg, at most 100 U/kg, or at most 1000 U/kg. In yet other aspects of this embodiment, the amount of Clostridial toxin active ingredient added to the formulation is from about 0.001 U/kg to about 1000 U/kg, about 0.01 U/kg to about 1000 U/kg, about 0.1 U/kg to about 1000 U/kg, or about 1.0 U/kg to about 1000 U/kg. In still other aspects of this embodiment, the amount of Clostridial toxin active ingredient added to the formulation is from about 0.001 U/kg to about 100 U/kg, about 0.01 U/kg to about 100 U/kg, about 0.1 U/kg to about 100 U/kg, or about 1.0 U/kg to about 100 U/kg. As used herein, the term "unit" or "U" is refers to the $LD_{50}$ dose, which is defined as the amount of a Clostridial toxin, Clostridial toxin complex or modified Clostridial toxin that killed 50% of the mice injected with the Clostridial toxin, Clostridial toxin complex or modified Clostridial toxin. As used herein, the term "about" when qualifying a value of a stated item, number, percentage, or term refers to a range of plus or minus ten percent of the value of the stated item, percentage, parameter, or term.

In other aspects of this embodiment, the amount of Clostridial toxin active ingredient added to the formulation is at least 1.0 pg, at least 10 pg, at least 100 pg, at least 1.0 ng, at least 10 ng, at least 100 ng, at least 1.0 µg, at least 10 µg, at least 100 µg, or at least 1.0 mg. In still other aspects of this embodiment, the amount of Clostridial toxin active ingredient added to the formulation is at most 1.0 pg, at most 10 pg, at most 100 pg, at most 1.0 ng, at most 10 ng, at most 100 ng, at most 1.0 µg, at most 10 µg, at most 100 µg, or at most 1.0 mg. In still other aspects of this embodiment, the amount of Clostridial toxin active ingredient added to the formulation is about 1.0 pg to about 10 µg, about 10 pg to about 10 µg, about 100 pg to about 10 µg, about 1.0 ng to about 10 µg, about 10 ng to about 10 µg, or about 100 ng to about 10 µg. In still other aspects of this embodiment, the amount of Clostridial toxin active ingredient added to the formulation is about 1.0 pg to about 1.0 µg, about 10 pg to about 1.0 µg, about 100 pg to about 1.0 µg, about 1.0 ng to about 1.0 µg, about 10 ng to about 1.0 µg, or about 100 ng to about 1.0 µg.

Aspects of the present pharmaceutical compositions provide, in part, a Clostridial toxin as a Clostridial toxin active ingredient. As used herein, the term "Clostridial toxin" refers to any neurotoxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate. Non-limiting examples of Clostridial toxins include a Botulinum toxin like BoNT/A, a BoNT/B, a BoNT/$C_1$, a BoNT/D, a BoNT/E, a BoNT/F, a BoNT/G, a Tetanus toxin (TeNT), a *Baratii* toxin (BaNT), and a *Butyricum* toxin (BuNT). The BoNT/$C_2$ cytotoxin and BoNT/$C_3$ cytotoxin, not being neurotoxins, are excluded from the term "Clostridial toxin." Clostridial toxins can be obtained from, e.g., List Biological Laboratories, Inc. (Campbell, Calif.), the Centre for Applied Microbiology and Research (Porton Down, U.K), Wako (Osaka, Japan), and Sigma Chemicals (St Louis, Mo.). In addition, Clostridial toxins can be produced using standard purification or recombinant biology techniques known to those skilled in the art. For example, using the Schantz process, NAPs can be separated out to obtain purified toxin, such as e.g., BoNT/A with an approximately 150 kD molecular weight with a specific potency of $1-2\times10^8$ $LD_{50}$ U/mg or greater, purified BoNT/B with an approximately 156 kD molecular weight with a specific potency of $1-2\times10^8$ $LD_{50}$ U/mg or greater, and purified BoNT/F with an approximately 155 kD molecular weight with a specific potency of $1-2\times10^7$ $LD_{50}$ U/mg or greater. See Edward J. Schantz & Eric A. Johnson, *Properties and use of Botulinum Toxin and Other Microbial Neurotoxins in Medicine*, Microbiol Rev. 56: 80-99 (1992). As another example, recombinant Clostridial toxins can be recombinantly produced as described in Lance E. Steward et al., Optimizing Expression of Active Botulinum Toxin Type A, U.S. Patent Publication 2008/0057575; and Lance E. Steward et al., Optimizing Expression of Active Botulinum Toxin Type E, U.S. Patent Publication 2008/0138893, each of which is hereby incorporated in its entirety.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., *Align-M-A New Algorithm for Multiple Alignment of Highly Divergent Sequences*, 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

Thus in an embodiment, a Clostridial toxin pharmaceutical composition comprises a Clostridial toxin as the Clostridial toxin active ingredient. In aspects of this embodiment, a Clostridial toxin pharmaceutical composition comprises a BoNT/A, a BoNT/B, a BoNT/C₁, a BoNT/D, a BoNT/E, a BoNT/F, a BoNT/G, a TeNT, a BaNT, or a BuNT. In another embodiment, a Clostridial toxin pharmaceutical composition comprises a Clostridial toxin variant as the Clostridial toxin active ingredient. In aspects of this embodiment, a Clostridial toxin pharmaceutical composition comprises naturally-occurring Clostridial toxin variant or a non-naturally-occurring Clostridial toxin variant. In other aspects of this embodiment, a Clostridial toxin pharmaceutical composition comprises a BoNT/A variant, a BoNT/B variant, a BoNT/C₁ variant, a BoNT/D variant, a BoNT/E variant, a BoNT/F variant, a BoNT/G variant, a TeNT variant, a BaNT variant, or a BuNT variant, where the variant is either a naturally-occurring variant or a non-naturally-occurring variant.

Aspects of the present pharmaceutical compositions provide, in part, a Clostridial toxin complex as a Clostridial toxin active ingredient. As used herein, the term "Clostridial toxin complex" refers to a complex comprising a Clostridial toxin and associated NAPs, such as, e.g., a Botulinum toxin complex, a Tetanus toxin complex, a *Baratii* toxin complex, and a *Butyricum* toxin complex. Non-limiting examples of Clostridial toxin complexes include those produced by a *Clostridium botulinum*, such as, e.g., a 900-kDa BoNT/A complex, a 500-kDa BoNT/A complex, a 300-kDa BoNT/A complex, a 500-kDa BoNT/B complex, a 500-kDa BoNT/C, complex, a 500-kDa BoNT/D complex, a 300-kDa BoNT/D complex, a 300-kDa BoNT/E complex, and a 300-kDa BoNT/F complex. Clostridial toxin complexes can be purified using the methods described in Schantz, supra, (1992); Hui Xiang et al., Animal Product Free System and Process for Purifying a Botulinum Toxin, U.S. Pat. No. 7,354,740, each of which is hereby incorporated by reference in its entirety. Clostridial toxin complexes can be obtained from, e.g., List Biological Laboratories, Inc. (Campbell, Calif.), the Centre for Applied Microbiology and Research (Porton Down, U.K), Wako (Osaka, Japan), and Sigma Chemicals (St Louis, Mo.).

For example, high quality crystalline BoNT/A complex can be produced from the Hall A strain of *Clostridium botulinum* with characteristics of ≥3×10⁷ U/mg, an A260/A278 of less than 0.60 and a distinct pattern of banding on gel electrophoresis using the Schantz process. See Schantz, supra, (1992). Generally, the BoNT/A complex can be isolated and purified from an anaerobic fermentation by cultivating *Clostridium botulinum* type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline BoNT/A complex with a specific potency of 3×10⁷ LD₅₀ U/mg or greater.

Thus in an embodiment, a Clostridial toxin pharmaceutical composition comprises a Clostridial toxin complex as the Clostridial toxin active ingredient. In aspects of this embodiment, a Clostridial toxin pharmaceutical composition comprises a BoNT/A complex, a BoNT/B complex, a BoNT/C, complex, a BoNT/D complex, a BoNT/E complex, a BoNT/F complex, a BoNT/G complex, a TeNT complex, a BaNT complex, or a BuNT complex. In other aspects of this embodiment, a Clostridial toxin pharmaceutical composition comprises a 900-kDa BoNT/A complex, a 500-kDa BoNT/A complex, a 300-kDa BoNT/A complex, a 500-kDa BoNT/B complex, a 500-kDa BoNT/C1 complex, a 500-kDa BoNT/D complex, a 300-kDa BoNT/D complex, a 300-kDa BoNT/E complex, or a 300-kDa BoNT/F complex.

Aspects of the present pharmaceutical compositions provide, in part, a modified Clostridial toxin as a Clostridial toxin active ingredient. As used herein, the term "modified Clostridial toxin" refers to any Clostridial toxin modified in some manner to provide a property or characteristic not present in the unmodified Clostridial toxin, but can still execute the overall cellular mechanism whereby a Clostridial toxin intoxicates a cell, including, e.g., the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate. Non-limiting examples of Clostridial toxin variants are described in Steward, L. E. et al., Post-Translational Modifications and Clostridial Neurotoxins, U.S. Pat. No. 7,223,577; Wei-Jen Lin et al., Neurotoxins with Enhanced Target Specificity, U.S. Pat. No. 7,273,722; Lance E. Steward et al., Clostridial Neurotoxin Compositions and Modified Clostridial Toxin Neurotoxins, U.S. Patent Publication 2004/0220386; Steward, L. E. et al., Clostridial Toxin Activatable Clostridial Toxins, U.S. Patent Publication 2007/0166332; Lance E. Steward et al., Modified Clostridial Toxins With Enhanced Targeting Capabilities For Endogenous Clostridial Toxin Receptor Systems, U.S. Patent Publication 2008/0096248; Steward, L. E. et al., Modified Clostridial Toxins with Enhanced Translocation Capability and Enhanced Targeting Activity, U.S. patent application Ser. No. 11/776,043; Steward, L. E. et al., Modified Clostridial Toxins with Enhanced Translocation Capabilities and Altered Targeting Activity For Clostridial Toxin Target Cells, U.S. patent application Ser. No. 11/776,052; each of which is incorporated by reference in its entirety. Steward, L. E. et al., Degradable Clostridial Toxins, U.S. patent application Ser. No. 12/192,905; each of which is incorporated by reference in its entirety.

Thus in an embodiment, a Clostridial toxin pharmaceutical composition comprises a modified Clostridial toxin as the Clostridial toxin active ingredient. In aspects of this embodiment, a Clostridial toxin pharmaceutical composition comprises a modified BoNT/A, a modified BoNT/B, a modified BoNT/C₁, a modified BoNT/D, a modified BoNT/E, a modified BoNT/F, a modified BoNT/G, a modified TeNT, a modified BaNT, or a modified BuNT.

Aspects of the present pharmaceutical compositions provide, in part, a re-targeted Clostridial toxin as a Clostridial toxin active ingredient. As used herein, the term "re-targeted Clostridial toxin" refers to a Clostridial toxin modified to selectively bind to a non-Clostridial toxin receptor present on a non-Clostridial toxin target cell, but otherwise execute the remaining intoxication steps of a Clostridial toxin, such as, e.g., the internalization of the toxin/receptor complex, the translocation of the Clostridial toxin light chain into the cytoplasm and the enzymatic modification of a Clostridial toxin substrate. A retargeted Clostridial toxin can intoxicate wither a neuronal cell or a non-neuronal cell, depending on the modification made to the Clostridial toxin. A re-targeted Clostridial toxin can be a re-targeted Botulinum toxin, re-targeted Tetanus toxin, re-targeted *Baratii* toxin and a re-targeted *Butyricum* toxin. Non-limiting examples of a re-targeted Clostridial toxin are described in, e.g., Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Conrad P. Quinn et al., Methods and Compounds for the Treatment of Mucus Hypersecretion, U.S. Pat. No. 6,632,440; Lance E. Steward et al., Methods And Compositions For The Treatment Of Pancreatitis, U.S. Pat. No. 6,843,998; J. Oliver Dolly et al., Activatable Recombinant Neurotoxins, U.S. Pat. No. 7,132,259; Stephan Donovan, Clostridial Toxin Derivatives and Methods For Treating Pain, U.S. Patent Publication 2002/0037833; Keith A. Foster et al., Inhibition of Secretion from Non-neural Cells, U.S. Patent Publication 2003/0180289; Lance E. Steward et al., Multivalent Clostridial Toxin Derivatives and Methods of Their Use, U.S. Patent Publication 2006/0211619; Keith A. Foster et al., Non-Cytotoxic Protein Conjugates, U.S. Patent Publication 2008/0187960; Steward, L. E. et al., Modified Clostridial Toxins with Enhanced Translocation Capabilities and Altered Targeting Activity For Non-Clostridial Toxin Target Cells, U.S. patent application Ser. No. 11/776,075; Keith A. Foster et al., Re-targeted Toxin Conjugates, U.S. patent application Ser. No. 11/792,210; each of which is incorporated by reference in its entirety.

Thus in an embodiment, a Clostridial toxin pharmaceutical composition comprises a re-targeted Clostridial toxin as the Clostridial toxin active ingredient. In aspects of this embodiment, a Clostridial toxin pharmaceutical composition comprises a re-targeted BoNT/A, a re-targeted BoNT/B, a re-targeted BoNT/C$_1$, a re-targeted BoNT/D, a re-targeted BoNT/E, a re-targeted BoNT/F, a re-targeted BoNT/G, a re-targeted TeNT, a re-targeted BaNT, or a re-targeted BuNT. In another aspect of this embodiment, a Clostridial toxin pharmaceutical composition comprises a re-targeted Clostridial toxin comprises an opioid targeting moiety, such as, e.g., an enkephalin, an endomorphin, an endorphin, a dynorphin, a nociceptin or a hemorphin. In yet another aspect of this embodiment, a Clostridial toxin pharmaceutical composition comprises a re-targeted Clostridial toxin comprises a tachykinin targeting moiety, such as, e.g., a Substance P, a neuropeptide K (NPK), a neuropeptide gamma (NP gamma), a neurokinin A (NKA; Substance K, neurokinin alpha, neuromedin L), a neurokinin B (NKB), a hemokinin or a endokinin. In still another aspect of this embodiment, a Clostridial toxin pharmaceutical composition comprises a re-targeted Clostridial toxin comprises a melanocortin targeting moiety, such as, e.g., a melanocyte stimulating hormone, adrenocorticotropin, or a lipotropin. In still another aspect of this embodiment, a Clostridial toxin pharmaceutical composition comprises a re-targeted Clostridial toxin comprises a galanin targeting moiety, such as, e.g., a galanin or a galanin message-associated peptide. In a further aspect of this embodiment, a Clostridial toxin pharmaceutical composition comprises a re-targeted Clostridial toxin comprises a granin targeting moiety, such as, e.g., a Chromogranin A, a Chromogranin B, or a Chromogranin C. In another aspect of this embodiment, a Clostridial toxin pharmaceutical composition comprises a re-targeted Clostridial toxin comprises a Neuropeptide Y related peptide targeting moiety, such as, e.g., a Neuropeptide Y, a Peptide YY, Pancreatic peptide ora Pancreatic icosapeptide. In yet another aspect of this embodiment, a Clostridial toxin pharmaceutical composition comprises a re-targeted Clostridial toxin comprises a neurohormone targeting moiety, such as, e.g., a corticotropin-releasing hormone, a parathyroid hormone, a thyrotropin-releasing hormone, or a somatostatin. In still another aspect of this embodiment, a Clostridial toxin pharmaceutical composition comprises a re-targeted Clostridial toxin comprises a neuroregulatory cytokine targeting moiety, such as, e.g., a ciliary neurotrophic factor, a glycophorin-A, a leukemia inhibitory factor, a cholinergic differentiation factor, an interleukin, an onostatin M, a cardiotrophin-1, a cardiotrophin-like cytokine, or a neuroleukin. In a further aspect of this embodiment, a Clostridial toxin pharmaceutical composition comprises a re-targeted Clostridial toxin comprises a kinin peptide targeting moiety, such as, e.g., a bradykinin, a kallidin, a desArg9 bradykinin, or a desArg10 bradykinin. In another aspect of this embodiment, a Clostridial toxin pharmaceutical composition comprises a re-targeted Clostridial toxin comprises a fibroblast growth factor targeting moiety, a nerve growth factor targeting moiety, an insulin growth factor targeting moiety, an epidermal growth factor targeting moiety, a vascular endothelial growth factor targeting moiety, a brain derived neurotrophic factor targeting moiety, a growth derived neurotrophic factor targeting moiety, a neurotrophin targeting moiety, such as, e.g., a neurotrophin-3, a neurotrophin-4/5, a head activator peptide targeting moiety, a neurturin targeting moiety, a persephrin targeting moiety, an artemin targeting moiety, a transformation growth factor β targeting moiety, such as, e.g., a TGFβ1, a TGFβ2, a TGFβ3 or a TGFβ4, a bone morphogenic protein targeting moiety, such as, e.g., a BMP2, a BMP3, a BMP4, a BMP5, a BMP6, a BMP7, a BMP8 or a BMP10, a growth differentiation factor targeting moiety, such as, e.g., a GDF1, a GDF2, a GDF3, a GDF5, a GDF6, a GDF7, a GDF8, a GDF10, a GDF11 or a GDF15, or an activin targeting moiety, such as, e.g., an activin A, an activin B, an activin C, an activin E or an inhibin A. In another aspect of this embodiment, a Clostridial toxin pharmaceutical composition comprises a re-targeted Clostridial toxin comprises a glucagon like hormone targeting moiety, such as, e.g., a secretin, a glucagon-like peptide, like a GLP-1 and a GLP-2, a pituitary adenylate cyclase activating peptide targeting moiety, a growth hormone-releasing hormone targeting moiety, vasoactive intestinal peptide targeting moiety like a VIP1 or a VIP2, a gastric inhibitory polypeptide targeting moiety, a calcitonin-related peptidesvisceral gut peptide targeting moiety like a gastrin, a gastrin-releasing peptide or a cholecystokinin, or a PAR peptide targeting moiety like a PAR1 peptide, a PAR2 peptide, a PAR3 peptide or a PAR4 peptide.

Aspects of the present pharmaceutical compositions provide, in part, a pharmacologically acceptable excipient. As used herein, the term "pharmacologically acceptable excipient" is synonymous with "pharmacological excipient" or "excipient" and refers to any excipient that has substantially no long term or permanent detrimental effect when administered to mammal and encompasses compounds such as, e.g., stabilizing agent, a bulking agent, a cryo-protectant, a lyo-protectant, an additive, a vehicle, a carrier, a diluent, or an auxiliary. An excipient generally is mixed with an active ingredient, or permitted to dilute or enclose the active ingredient and can be a solid, semi-solid, or liquid agent. It is also envisioned that a pharmaceutical composition comprising a Clostridial toxin active ingredient can include one or more pharmaceutically acceptable excipients that facilitate processing of an active ingredient into pharmaceutically acceptable compositions. Insofar as any pharmacologically acceptable excipient is not incompatible with the Clostridial toxin active ingredient, its use in pharmaceutically acceptable compositions is contemplated. Non-limiting examples of pharmacologically acceptable excipients can be found in, e.g., Pharmaceutical Dosage Forms and Drug Delivery Systems (Howard C. Ansel et al., eds., Lippincott Williams & Wilkins Publishers, 7$^{th}$ ed. 1999); Remington: The Science and Practice of Pharmacy (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003), each of which is hereby incorporated by reference in its entirety.

Aspects of the present pharmaceutical compositions provide, in part, an effective amount." As used herein, the term "effective amount," when used in reference to the amount of an excipient or specific combination of excipients added to a Clostridial toxin composition, refers to the amount of each excipient that is necessary to achieve the desired initial recovered potency of a Clostridial toxin active ingredient. In aspects of this embodiment, an effective amount of an excipient or combination of excipients results in an initial recovered potency of, e.g., at least 10%, at least 20%, at least 30%, at least 40%, at least 50%, at least 60%, at least 70%, at least 80%, at least 90% or at least 100%. In other aspects of this embodiment, a therapeutically effective concentration of a Clostridial toxin active ingredient reduces a symptom associated with the aliment being treated by, e.g., at most 10%, at most 20%, at most 30%, at most 40%, at most 50%, at most 60%, at most 70%, at most 80%, at most 90% or at most 100%.

In yet aspects of this embodiment, an effective amount of an excipient is, e.g., at least 0.1 mg, at least 0.125 mg, at least 0.2 mg, at least 0.25 mg, at least 0.3 mg, at least 0.3125 mg, at least 0.4 mg, at least 0.5 mg, at least 0.6 mg, at least 0.625 mg, at least 0.7 mg, at least 0.8 mg, or at least 0.9 mg. In still aspects of this embodiment, an effective amount of an excipient is, e.g., at least 1.0 mg, at least 2.0 mg, at least 3.0 mg, at least 4.0 mg, at least 5.0 mg, at least 6.0 mg, at least 7.0 mg, at least 8.0 mg, or at least 9.0 mg. In further aspects of this embodiment, an effective amount of an excipient is, e.g., at least 10 mg, at least 20 mg, at least 30 mg, at least 40 mg, at least 50 mg, at least 60 mg, at least 70 mg, at least 80 mg, at least 90 mg, or at least 100 mg.

In yet aspects of this embodiment, an effective amount of an excipient is, e.g., at most 0.1 mg, at most 0.125 mg, at most 0.2 mg, at most 0.25 mg, at most 0.3 mg, at most 0.3125 mg, at most 0.4 mg, at most 0.5 mg, at most 0.6 mg, at most 0.625 mg, at most 0.7 mg, at most 0.8 mg, or at most 0.9 mg. In still aspects of this embodiment, an effective amount of an excipient is, e.g., at most 1.0 mg, at most 2.0 mg, at most 3.0 mg, at most 4.0 mg, at most 5.0 mg, at most 6.0 mg, at most 7.0 mg, at most 8.0 mg, or at most 9.0 mg. In further aspects of this embodiment, an effective amount of an excipient is, e.g., at most 10 mg, at most 20 mg, at most 30 mg, at most 40 mg, at most 50 mg, at most 60 mg, at most 70 mg, at most 80 mg, at most 90 mg, or at most 100 mg.

In yet aspects of this embodiment, an effective amount of an excipient is, e.g., from about 0.1 mg to about 100 mg, from about 0.1 mg to about 50 mg, from about 0.1 mg to about 10 mg, from about 0.25 mg to about 100 mg, from about 0.25 mg to about 50 mg, from about 0.25 mg to about 10 mg, from about 0.5 mg to about 100 mg, from about 0.5 mg to about 50 mg, from about 0.5 mg to about 10 mg, from about 0.75 mg to about 100 mg, from about 0.75 mg to about 50 mg, from about 0.75 mg to about 10 mg, from about 1.0 mg to about 100 mg, from about 1.0 mg to about 50 mg, or from about 1.0 mg to about 10 mg.

Aspects of the present pharmaceutical compositions provide, in part, non-protein excipient. As used herein, the term "non-protein excipient" refers to any excipient that is not a polypeptide comprising at least fifteen amino acids. It is envisioned that any non-protein excipient is useful in formulating a Clostridial toxin pharmaceutical compositions disclosed in the present specification, with the proviso that a therapeutically effective amount of the Clostridial toxin active ingredient is recovered using this non-protein excipient.

Aspects of the present pharmaceutical compositions provide, in part, a sugar. As used herein, the term "sugar" refers to a compound comprising one to 10 monosaccharide units, e.g., a monosaccharide, a disaccharide, a trisaccharide, and an oligosaccharide comprising four to ten monosaccharide units. It is envisioned that any sugar is useful in formulating a Clostridial toxin pharmaceutical compositions disclosed in the present specification, with the proviso that a therapeutically effective amount of the Clostridial toxin active ingredient is recovered using this sugar. Monosaccharides are polyhydroxy aldehydes or polyhydroxy ketones with three or more carbon atoms, including aldoses, dialdoses, aldoketoses, ketoses and diketoses, as well as cyclic forms, deoxy sugars and amino sugars, and their derivatives, provided that the parent monosaccharide has a (potential) carbonyl group. Monosaccharides include trioses, like glyceraldehyde and dihydroxyacetone; tetroses, like erythrose, threose and erythrulose; pentoses, like arabinose, lyxose, ribose, xylose, ribulose, xylulose; hexoses, like allose, altrose, galactose, glucose, gulose, idose, mannose, talose, fructose, psicose, sorbose, tagatose, fucose, rhamnose; heptoses, like sedoheptulose and mannoheptulose; octooses, like octulose and 2-keto-3-deoxy-manno-octonate; nonoses like sialose; and decose. Oligosaccharides are compounds in which at least two monosaccharide units are joined by glycosidic linkages. According to the number of units, they are called disaccharides, trisaccharides, tetrasaccharides, pentasaccharides, hexasaccharides, heptasaccharides, octosaccharides, nonosaccharides, decosaccharides, etc. An oligosaccharide can be unbranched, branched or cyclic. Common disaccharides include, without limitation, sucrose, lactose, maltose, trehalose, cellobiose, gentiobiose, kojibiose, laminaribiose, mannobiose, melibiose, nigerose, rutinose, and xylobiose. Common trisaccharides include, without limitation, raffinose, acarbose, maltotriose, and melezitose. Other non-limiting examples of specific uses of sugar excipients can be found in, e.g., ANSEL, SUPRA, (1999); GENNARO, SUPRA, (2000); HARDMAN, SUPRA, (2001); AND ROWE, SUPRA, (2003), each of which is hereby incorporated by reference in its entirety.

Thus in an embodiment, a Clostridial toxin pharmaceutical composition comprises a sugar. In aspects of this embodiment, a Clostridial toxin pharmaceutical composition comprises a monosaccharide. In other aspects of this embodiment, a Clostridial toxin pharmaceutical composition comprises a disaccharide, a trisaccharide, a tetrasaccharide, a pentasaccharide, a hexasaccharide, a heptasaccharide, an octosaccharide, a nonosaccharide, or a decosaccharide. In yet other aspects of this embodiment, a Clostridial toxin pharmaceutical composition comprises an oligosaccharide comprising two to ten monosaccharide units.

It is envisioned that any amount of sugar is useful in formulating a Clostridial toxin pharmaceutical compositions disclosed in the present specification, with the proviso that a therapeutically effective amount of the Clostridial toxin active ingredient is recovered using this sugar amount. In aspects of this embodiment, the amount of sugar added to the formulation is at least 0.5% (w/v), at least 1.0% (w/v), at least 2.0% (w/v), at least 3.0% (w/v), at least 4.0% (w/v), at least 5.0% (w/v), at least 6.0% (w/v), at least 7.0% (w/v), at least 8.0% (w/v), at least 9.0% (w/v), at least 10% (w/v), at least 15% (w/v), at least 20% (w/v), at least 25% (w/v), at least 30% (w/v), or at least 35% (w/v). In other aspects of this embodiment, the amount of sugar added to the formulation is at most 0.5% (w/v), at most 1.0% (w/v), at most 2.0% (w/v), at most 3.0% (w/v), at most 4.0% (w/v), at most 5.0% (w/v), at most 6.0% (w/v), at most 7.0% (w/v), at most 8.0% (w/v), at most 9.0% (w/v), at most 10% (w/v), at most 15% (w/v), at most 20% (w/v), at most 25% (w/v), at most 30% (w/v), or at most 35% (w/v).

Aspects of the present pharmaceutical compositions provide, in part, a polyol. As used herein, the term "polyol" is synonymous with "sugar alcohol," "polyhydric alcohol," and "polyalcohol" and refers to a sugar derivative having an alcohol group ($CH_2OH$) instead of the aldehyde group (CHO), such as, e.g., mannitol from mannose, xylitol from xylose, and lactitol from lactulose. It is envisioned that any polyol is useful in formulating a Clostridial toxin pharmaceutical compositions disclosed in the present specification, with the proviso that a therapeutically effective amount of the Clostridial toxin active ingredient is recovered using this polyol. Non-limiting examples of polyols include, glycol, glycerol, arabitol, erythritol, xylitol, maltitol, sorbitol (glucitol), mannitol, inositol, lactitol, galactitol (iditol), isomalt. Other non-limiting examples of sugar excipients can be found in, e.g., Ansel, supra, (1999); Gennaro, supra, (2000); Hardman, supra, (2001); and Rowe, supra, (2003), each of which is hereby incorporated by reference in its entirety.

Thus in an embodiment, a Clostridial toxin pharmaceutical composition comprises a polyol. In aspects of this embodiment, a Clostridial toxin pharmaceutical composition comprises glycol, glycerol, arabitol, erythritol, xylitol, maltitol, sorbitol (glucitol), mannitol, inositol, lactitol, galactitol (iditol), or isomalt.

It is envisioned that any amount of polyol is useful in formulating a Clostridial toxin pharmaceutical compositions disclosed in the present specification, with the proviso that a therapeutically effective amount of the Clostridial toxin active ingredient is recovered using this polyol amount. In aspects of this embodiment, the amount of polyol added to the formulation is at least 0.5% (w/v), at least 1.0% (w/v), at least 2.0% (w/v), at least 3.0% (w/v), at least 4.0% (w/v), at least 5.0% (w/v), at least 6.0% (w/v), at least 7.0% (w/v), at least 8.0% (w/v), at least 9.0% (w/v), at least 10% (w/v), at least 15% (w/v), at least 20% (w/v), at least 25% (w/v), at least 30% (w/v), or at least 35% (w/v). In other aspects of this embodiment, the amount of polyol added to the formulation is at most 0.5% (w/v), at most 1.0% (w/v), at most 2.0% (w/v), at most 3.0% (w/v), at most 4.0% (w/v), at most 5.0% (w/v), at most 6.0% (w/v), at most 7.0% (w/v), at most 8.0% (w/v), at most 9.0% (w/v), at most 10% (w/v), at most 15% (w/v), at most 20% (w/v), at most 25% (w/v), at most 30% (w/v), or at most 35% (w/v).

Aspects of the present pharmaceutical compositions provide, in part, a polymer. As used herein, the term "polymer" refers to high molecular weight compounds comprising at least eleven monomeric units. Polymers consisting of only one kind of repeating unit are called homopolymers, whereas polymers formed from two or more different repeating units and called copolymers. A polymer can be natural or synthetic. Non-limiting examples of polymers include polysaccharides, such as, e.g., dextrans (like dextran 1K, dextran 4K, dextran 40K, dextran 60K, and dextran 70K), dextrin, glycogen, inulin, starch, starch derivatives (like hydroxymethyl starch, hydroxyethyl starch, hydroxypropyl starch, hydroxybutyl starch, and hydroxypentyl starch), hetastarch, cellulose, FICOLL, methyl cellulose (MC), carboxymethyl cellulose (CMC), hydroxyethyl cellulose (HEC), hydroxypropyl cellulose (HPC), hydroxyethyl methyl cellulose (HEMC), hydroxypropyl methyl cellulose (HPMC); polyvinyl acetates (PVA); polyvinyl pyrrolidones (PVP), also known as povidones, having a K-value of less than or equal to 18, a K-value greater than 18 or less than or equal to 95, or a K-value greater than 95, like PVP 12 (KOLLIDON® 12), PVP 17 (KOLLIDON® 17), PVP 25 (KOLLIDON® 25), PVP 30 (KOLLIDON® 30), PVP 90 (KOLLIDON® 90); polyethylene glycols like PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 75000, PEG 7500, or PEG 8000; and polyethylene imines (PEI); polypeptides (proteins) like bovine serum albumin, gelatin, and ovalbumin; polynucleotides like DNA and RNA. Other non-limiting examples of polymer excipients can be found in, e.g., Ansel, supra, (1999); Gennaro, supra, (2000); Hardman, supra, (2001); and Rowe, supra, (2003), each of which is hereby incorporated by reference in its entirety.

It is envisioned that any non-protein polymer is useful in formulating a Clostridial toxin pharmaceutical compositions disclosed in the present specification, with the proviso that a therapeutically effective amount of the Clostridial toxin active ingredient is recovered using this non-protein polymer. Thus in an embodiment, a Clostridial toxin pharmaceutical composition comprises a non-protein polymer. In an aspect of this embodiment, a Clostridial toxin pharmaceutical composition comprises a polysaccharide. In aspects of this embodiment, a Clostridial toxin pharmaceutical composition comprises a dextran, an inulin, a starch, a starch derivative, a hetastarch, a dextrin, a glycogen, a cellulose, FICOLL, a methyl cellulose (MC), a carboxymethyl cellulose (CMC), a hydroxyethyl cellulose (HEC), a hydroxypropyl cellulose (HPC), a hydroxyethyl methyl cellulose (HEMC), or a hydroxypropyl methyl cellulose (HPMC). In another aspect of this embodiment, a Clostridial toxin pharmaceutical composition comprises a polyvinyl acetate. In another aspect of this embodiment, a Clostridial toxin pharmaceutical composition comprises a polyvinylpyrrolidone. In aspects of this embodiment, a Clostridial toxin pharmaceutical composition comprises dextran 1K, dextran 4K, dextran 40K, dextran 60K, or dextran 70K. In another aspect of this embodiment, a Clostridial toxin pharmaceutical composition comprises PVP 12, PVP 17, PVP 25, PVP 30, or PVP 90. In yet another aspect of this embodiment, a Clostridial toxin pharmaceutical composition comprises a polyethylene glycol. In an aspect of this embodiment, a Clostridial toxin pharmaceutical composition comprises a room temperature solid PEG. In aspects of this embodiment, a Clostridial toxin pharmaceutical composition comprises PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 75000, PEG 7500, or PEG 8000. In another aspect of this embodiment, a Clostridial toxin pharmaceutical composition comprises a polyethylene imine.

It is envisioned that any amount of non-protein polymer is useful in formulating a Clostridial toxin pharmaceutical compositions disclosed in the present specification, with the proviso that a therapeutically effective amount of the Clostridial toxin active ingredient is recovered using this non-protein polymer amount. In other aspects of this embodiment, the amount of non-protein polymer added to the formulation is at least 0.5% (w/v), at least 1.0% (w/v), at least 2.0% (w/v), at least 3.0% (w/v), at least 4.0% (w/v), at least 5.0% (w/v), at least 6.0% (w/v), at least 7.0% (w/v), at least 8.0% (w/v), at least 9.0% (w/v), at least 10% (w/v), at least 15% (w/v), at least 20% (w/v), at least 25% (w/v), at least 30% (w/v), or at least 35% (w/v). In other aspects of this embodiment, the amount of non-protein polymer added to the formulation is at most 0.5% (w/v), at most 1.0% (w/v), at most 2.0% (w/v), at most 3.0% (w/v), at most 4.0% (w/v), at most 5.0% (w/v), at most 6.0% (w/v), at most 7.0% (w/v), at most 8.0% (w/v), at most 9.0% (w/v), at most 10% (w/v), at most 15% (w/v), at most 20% (w/v), at most 25% (w/v), at most 30% (w/v), or at most 35% (w/v).

Aspects of the present pharmaceutical compositions provide, in part, a surfactant. As used hereon, the term "surfactant" refers to a natural or synthetic amphiphilic compound. A surfactant can be non-ionic, zwitterionic, or ionic. It is envisioned that any surfactant is useful in formulating a Clostridial toxin pharmaceutical compositions disclosed in the present specification, with the proviso that a therapeutically effective amount of the Clostridial toxin active ingredient is recovered using this surfactant amount. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyl) dimethylammonio]-1-propanesulfonate (CHAPS); 3-[(3-Cholamidopropyl) dimethylammonio]-2-hydroxy-1-propanesulfonate (CHAPSO); sucrose monolaurate; and sodium cholate. Other non-limiting examples of surfactant excipients can be found in, e.g., Ansel, supra, (1999); Gennaro, supra, (2000); Hardman, supra, (2001); and Rowe, supra, (2003), each of which is hereby incorporated by reference in its entirety.

Thus in an embodiment, a Clostridial toxin pharmaceutical composition comprises a surfactant. In aspects of this embodiment, a Clostridial toxin pharmaceutical composition comprises a polysorbate, a poloxamer, a polyoxyethyleneglycol dodecyl ether, 2-dodecoxyethanol, polyoxyethylene octyl phenyl ether, sodium dodecyl sulfate, 3-[(3-Cholamidopropyl)dimethylammonio]-1-propanesulfonate, 3-[(3-Cholamidopropyl) dimethylammonio]-2-hydroxy-1-propanesulfonate, sucrose monolaurate; or sodium cholate.

It is envisioned that any amount of surfactant is useful in formulating a Clostridial toxin pharmaceutical compositions disclosed in the present specification, with the proviso that a therapeutically effective amount of the Clostridial toxin active ingredient is recovered using this surfactant amount. In aspects of this embodiment, the amount of surfactant added to the formulation is at least 0.5% (w/v), at least 1.0% (w/v), at least 2.0% (w/v), at least 3.0% (w/v), at least 4.0% (w/v), at least 5.0% (w/v), at least 6.0% (w/v), at least 7.0% (w/v), at least 8.0% (w/v), at least 9.0% (w/v), at least 10% (w/v), at least 15% (w/v), at least 20% (w/v), at least 25% (w/v), at least 30% (w/v), or at least 35% (w/v). In other aspects of this embodiment, the amount of surfactant added to the formulation is at most 0.5% (w/v), at most 1.0% (w/v), at most 2.0% (w/v), at most 3.0% (w/v), at most 4.0% (w/v), at most 5.0% (w/v), at most 6.0% (w/v), at most 7.0% (w/v), at most 8.0% (w/v), at most 9.0% (w/v), at most 10% (w/v), at most 15% (w/v), at most 20% (w/v), at most 25% (w/v), at most 30% (w/v), or at most 35% (w/v).

In yet other aspects of this embodiment, the amount of surfactant added to the formulation is at least 0.5% (v/v), at least 1.0% (v/v), at least 2.0% (v/v), at least 3.0% (v/v), at least 4.0% (v/v), at least 5.0% (v/v), at least 6.0% (v/v), at least 7.0% (v/v), at least 8.0% (v/v), at least 9.0% (v/v), at least 10% (v/v), at least 15% (v/v), at least 20% (v/v), at least 25% (v/v), at least 30% (v/v), or at least 35% (v/v). In other aspects of this embodiment, the amount of surfactant added to the formulation is at most 0.5% (v/v), at most 1.0% (v/v), at most 2.0% (v/v), at most 3.0% (v/v), at most 4.0% (v/v), at most 5.0% (v/v), at most 6.0% (v/v), at most 7.0% (v/v), at most 8.0% (v/v), at most 9.0% (v/v), at most 10% (v/v), at most 15% (v/v), at most 20% (v/v), at most 25% (v/v), at most 30% (v/v), or at most 35% (v/v).

Aspects of the present pharmaceutical compositions provide, in part, an amino acid. As used hereon, the term "amino acid" refers to a molecule with the general formula $H_2NCHRCOOH$, where R is an organic substitute. It is envisioned that any amino acid is useful in formulating a Clostridial toxin pharmaceutical compositions disclosed in the present specification, with the proviso that a therapeutically effective amount of the Clostridial toxin active ingredient is recovered using this amino acid amount. Amino acids include both the twenty standard amino acids and non-standard amino acids. Non-limiting examples of amino acids include glycine, proline, 4-hydroxyproline, serine, glutamate, alanine, lysine, sarcosine, γ-aminobutyric acid. Other non-limiting examples of amino acids excipients can be found in, e.g., Ansel, supra, (1999); Gennaro, supra, (2000); Hardman, supra, (2001); and Rowe, supra, (2003), each of which is hereby incorporated by reference in its entirety.

Thus in an embodiment, a Clostridial toxin pharmaceutical composition comprises an amino acid. In aspects of this embodiment, a Clostridial toxin pharmaceutical composition comprises a glycine, proline, 4-hydroxyproline, serine, glutamate, alanine, lysine, sarcosine, or γ-aminobutyric acid.

It is envisioned that any amount of amino acid is useful in formulating a Clostridial toxin pharmaceutical compositions disclosed in the present specification, with the proviso that a therapeutically effective amount of the Clostridial toxin active ingredient is recovered using this amino acid amount. In aspects of this embodiment, the amount of amino acid added to the formulation is at least 0.5% (w/v), at least 1.0% (w/v), at least 2.0% (w/v), at least 3.0% (w/v), at least 4.0% (w/v), at least 5.0% (w/v), at least 6.0% (w/v), at least 7.0% (w/v), at least 8.0% (w/v), at least 9.0% (w/v), at least 10% (w/v), at least 15% (w/v), at least 20% (w/v), at least 25% (w/v), at least 30% (w/v), or at least 35% (w/v). In other aspects of this embodiment, the amount of amino acid added to the formulation is at most 0.5% (w/v), at most 1.0% (w/v), at most 2.0% (w/v), at most 3.0% (w/v), at most 4.0% (w/v), at most 5.0% (w/v), at most 6.0% (w/v), at most 7.0% (w/v), at most 8.0% (w/v), at most 9.0% (w/v), at most 10% (w/v), at most 15% (w/v), at most 20% (w/v), at most 25% (w/v), at most 30% (w/v), or at most 35% (w/v).

It is envisioned that a plurality of non-protein excipients is useful in formulating a Clostridial toxin pharmaceutical compositions disclosed in the present specification, with the proviso that a therapeutically effective amount of the Clostridial toxin active ingredient is recovered using this plurality of non-protein excipients. Thus in an embodiment, a Clostridial toxin pharmaceutical composition comprises a plurality of non-protein excipients. In aspects of this embodiment, a Clostridial toxin pharmaceutical composition can comprise, e.g., at least two non-protein excipients, at least three non-protein excipients, at least four non-protein excipients, at least five non-protein excipients, at least six non-protein excipients, at least seven non-protein excipients or at least eight non-protein excipients. In other aspects of this embodiment, a Clostridial toxin pharmaceutical composition can comprise, e.g., at most two non-protein excipients, at most three non-protein excipients, at most four non-protein excipients, at most five non-protein excipients, at most six non-protein excipients, at most seven non-protein excipients or at most eight non-protein excipients. In other aspects of this embodiment, a Clostridial toxin pharmaceutical composition can comprise, e.g., 2-10 non-protein excipients, 2-8, non-protein excipients, 2-6 non-protein excipients, 2-4 non-protein excipients, 3-10 non-protein excipients, 3-8, non-protein excipients, 3-6 non-protein excipients, 3-4 non-protein excipients, 4-10 non-protein excipients, 4-8 non-protein excipients, or 4-6 non-protein excipients. For example, a Clostridial toxin pharmaceutical composition can comprise two different sugars and a Clostridial toxin active ingredient, a Clostridial toxin pharmaceutical composition can comprise a sugar, a surfactant and a Clostridial toxin active ingredient, a Clostridial toxin pharmaceutical composition can comprise a non-protein polymer, a surfactant and a Clostridial toxin active ingredient, or a Clostridial toxin pharmaceutical composition can comprise a sugar, a non-protein polymer, a surfactant and a Clostridial toxin active ingredient.

It is envisioned that any ratio of non-protein excipients is useful in formulating a Clostridial toxin pharmaceutical compositions disclosed in the present specification, with the proviso that a therapeutically effective amount of the Clostridial toxin active ingredient is recovered using this excipient ratio. In aspects of this embodiment, when two non-protein excipients are added to the formulation, the ratio of the first excipient to the second excipient is at least 20:1, at least 15:1, at least 10:1, at least 9:1, at least 8:1, at least 7:1, at least 6:1, at least 5:1, at least 4:1, at least 3:1, at least 2:1, at least 1:1, at least 1:2, at least 1:3, at least 1:4, at least 1:5, at least 1:6, at least 1:7, at least 1:8, at least 1:9, at least 1:10, at least 1:15, or at least 1:20. In other aspects of this embodiment, when three non-protein excipients are added to the formulation, the ratio of the first excipient to the second excipient and third excipient is at least 10:2:1, at least 9:2:1, at least 8:2:1, at least 7:2:1, at least 6:2:1, at least 5:2:1, at least 4:2:1, at least 3:2:1, at least 2:2:1, at least 10:1:1, at least 9:1:1, at least 8:1:1, at least 7:1:1, at least 6:1:1, at least 5:1:1, at least 4:1:1, at least 3:1:1, at least 2:1:1, or at least 1:1:1.

It is further envisioned that a Clostridial toxin pharmaceutical composition disclosed in the present specification can optionally include, without limitation, other pharmaceutically acceptable components (or pharmaceutical components), including, without limitation, buffers, preservatives, tonicity adjusters, salts, antioxidants, osmolality adjusting agents, emulsifying agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a pharmaceutical composition as needed. It is envisioned that any buffered pH level can be useful in formulating a Clostridial toxin pharmaceutical composition, with the proviso that a therapeutically effective amount of the Clostridial toxin active ingredient is recovered using this effective pH level. In an aspect of this embodiment, an effective pH level is at least about pH 5.0, at least about pH 5.5, at least about pH 6.0, at least about pH 6.5, at least about pH 7.0 or at about about pH 7.5. In another aspect of this embodiment, an effective pH level is at most about pH 5.0, at most about pH 5.5, at most about pH 6.0, at most about pH 6.5, at most about pH 7.0 or at most about pH 7.5. In yet another aspect of this embodiment, an effective pH level is about pH 5.0 to about pH 8.0, an effective pH level is about pH 5.0 to about pH 7.0, an effective pH level is about pH 5.0 to about pH 6.0, is about pH 5.5 to about pH 8.0, an effective pH level is about pH 5.5 to about pH 7.0, an effective pH level is about pH 5.5 to about pH 5.0, is about pH 5.5 to about pH 7.5, an effective pH level is about pH 5.5 to about pH 6.5.

It is envisioned that any concentration of a buffer can be useful in formulating a Clostridial toxin pharmaceutical composition, with the proviso that a therapeutically effective amount of the Clostridial toxin active ingredient is recovered using this effective concentration of buffer. In aspects of this embodiment, an effective concentration of buffer is at least 0.1 mM, at least 0.2 mM, at least 0.3 mM, at least 0.4 mM, at least 0.5 mM, at least 0.6 mM, at least 0.7 mM, at least 0.8 mM, or at least 0.9 mM. In other aspects of this embodiment, an effective concentration of buffer is at least 1.0 mM, at least 2.0 mM, at least 3.0 mM, at least 4.0 mM, at least 5.0 mM, at least 6.0 mM, at least 7.0 mM, at least 8.0 mM, or at least 9.0 mM. In yet other aspects of this embodiment, an effective concentration of buffer is at least 10 mM, at least 20 mM, at least 30 mM, at least 40 mM, at least 50 mM, at least 60 mM, at least 70 mM, at least 80 mM, or at least 90 mM. In still other aspects of this embodiment, an effective concentration of buffer is at least 100 mM, at least 200 mM, at least 300 mM, at least 400 mM, at least 500 mM, at least 600 mM, at least 700 mM, at least 800 mM, or at least 900 mM. In further aspects of this embodiment, an effective concentration of buffer is at most 0.1 mM, at most 0.2 mM, at most 0.3 mM, at most 0.4 mM, at most 0.5 mM, at most 0.6 mM, at most 0.7 mM, at most 0.8 mM, or at most 0.9 mM. In still other aspects of this embodiment, an effective concentration of buffer is at most 1.0 mM, at most 2.0 mM, at most 3.0 mM, at most 4.0 mM, at most 5.0 mM, at most 6.0 mM, at most 7.0 mM, at most 8.0 mM, or at most 9.0 mM. In yet other aspects of this embodiment, an effective concentration of buffer is at most 10 mM, at most 20 mM, at most 30 mM, at most 40 mM, at most 50 mM, at most 60 mM, at most 70 mM, at most 80 mM, or at most 90 mM. In still other aspects of this embodiment, an effective concentration of buffer is at most 100 mM, at most 200 mM, at most 300 mM, at most 400 mM, at most 500 mM, at most 600 mM, at most 700 mM, at most 800 mM, or at most 900 mM. In still further aspects of this embodiment, an effective concentration of buffer is about 0.1 mM to about 900 mM, 0.1 mM to about 500 mM, 0.1 mM to about 100 mM, 0.1 mM to about 90 mM, 0.1 mM to about 50 mM, 1.0 mM to about 900 mM, 1.0 mM to about 500 mM, 1.0 mM to about 100 mM, 1.0 mM to about 90 mM, or 1.0 mM to about 50 mM.

Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride and potassium chloride. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention. Other non-limiting examples of pharmacologically acceptable components can be found in, e.g., Ansel, supra, (1999); Gennaro, supra, (2000); Hardman, supra, (2001); and Rowe, supra, (2003), each of which is hereby incorporated by reference in its entirety.

It is envisioned that any concentration of a salt can be useful in formulating a Clostridial toxin pharmaceutical composition, with the proviso that a therapeutically effective amount of the Clostridial toxin active ingredient is recovered using this effective concentration of salt. In aspects of this embodiment, an effective concentration of salt is at least 0.1 mM, at least 0.2 mM, at least 0.3 mM, at least 0.4 mM, at least 0.5 mM, at least 0.6 mM, at least 0.7 mM, at least 0.8 mM, or at least 0.9 mM. In other aspects of this embodiment, an effective concentration of salt is at least 1.0 mM, at least 2.0 mM, at least 3.0 mM, at least 4.0 mM, at least 5.0 mM, at least 6.0 mM, at least 7.0 mM, at least 8.0 mM, or at least 9.0 mM. In yet other aspects of this embodiment, an effective concentration of salt is at least 10 mM, at least 20 mM, at least 30 mM, at least 40 mM, at least 50 mM, at least 60 mM, at least 70 mM, at least 80 mM, or at least 90 mM. In still other aspects of this embodiment, an effective concentration of salt is at least 100 mM, at least 200 mM, at least 300 mM, at least 400 mM, at least 500 mM, at least 600 mM, at least 700 mM, at least 800 mM, or at least 900 mM. In further aspects of this embodiment, an effective concentration of salt is at most 0.1 mM, at most 0.2 mM, at most 0.3 mM, at most 0.4 mM, at most 0.5 mM, at most 0.6 mM, at most 0.7 mM, at most 0.8 mM, or at most 0.9 mM. In still other aspects of this embodiment, an effective concentration of salt is at most 1.0 mM, at most 2.0 mM, at most 3.0 mM, at most 4.0 mM, at most 5.0 mM, at most 6.0 mM, at most 7.0 mM, at most 8.0 mM, or at most 9.0 mM. In yet other aspects of this embodiment, an effective concentration of salt is at most 10 mM, at most 20 mM, at most 30 mM, at most 40 mM, at most 50 mM, at most 60 mM, at most 70 mM, at most 80 mM, or at most 90 mM. In still other aspects of this embodiment, an effective concentration of salt is at most 100 mM, at most 200 mM, at most 300 mM, at most 400 mM, at most 500 mM, at most 600 mM, at most 700 mM, at most 800 mM, or at most 900 mM. In still further aspects of this embodiment, an effective concentration of salt is about 0.1 mM to about 900 mM, 0.1 mM to about 500 mM, 0.1 mM to about 100 mM, 0.1 mM to about 90 mM, 0.1 mM to about 50 mM, 1.0 mM to about 900 mM, 1.0 mM to about 500 mM, 1.0 mM to about 100 mM, 1.0 mM to about 90 mM, or 1.0 mM to about 50 mM.

A pharmaceutical compositions disclosed in the present specification generally is administered as a pharmaceutical acceptable composition comprising a botulinum toxin active ingredient. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the Clostridial toxin active ingredients disclosed in the present specification. A pharmaceutical composition comprising a Clostridial toxin active ingredient is useful for medical and veterinary applications. A pharmaceutical composition may be administered to a patient alone, or in combination with other supplementary active ingredients, agents, drugs or hormones.

Aspects of the present pharmaceutical compositions provide, in part, recovered potency of a pharmaceutical composition. As used hereon, the term "recovered potency" is synonymous with "recovered activity" and, when used in reference to a solid-form Clostridial toxin pharmaceutical composition, refers to the percentage calculated by dividing the potency of the Clostridial toxin active ingredient in the stored reconstitution formulation by the potency of the active Clostridial toxin ingredient determined prior to its addition into the test solution. When used in reference to an aqueous-form Clostridial toxin pharmaceutical composition, "recovered potency" refers to the percentage calculated by dividing the potency of the Clostridial toxin active ingredient in the stored formulation by the potency of the active Clostridial toxin ingredient determined prior to its addition into the test solution. The maximum theoretical recovered potency is 100%. As used herein, the term "potency" refers to the level of biological activity exhibited by a Clostridial toxin active ingredient as measured by, e.g., a mouse bioassay or an in vitro Clostridial toxin light chain activity assay. As a non-limiting example, with respect to a solid-form Clostridial toxin pharmaceutical composition, a recovery of 60% means that the potency of the Clostridial toxin active ingredient after reconstitution was 60% of the potency of the Clostridial toxin active ingredient prior to its addition to the formulation. As another non-limiting example, with respect to an aqueous-form Clostridial toxin pharmaceutical composition, a recovery of 50% means that the potency of the Clostridial toxin active ingredient after storage was 50% of the potency of the Clostridial toxin active ingredient prior to its addition to the formulation.

It is envisioned that any level of recovered potency is useful in formulating a Clostridial toxin pharmaceutical compositions disclosed in the present specification, with the proviso that a therapeutically effective amount of the Clostridial toxin active ingredient is present. Thus, in an embodiment, a Clostridial toxin pharmaceutical composition disclosed in the present specification exhibits a recovered potency of at least 10%, at least 20%, at least 30%, at least 40%, at least 50%, at least 60%, at least 70%, at least 80%, at least 90%, or at least 100%. In another embodiment, a Clostridial toxin pharmaceutical composition disclosed in the present specification exhibits a recovered potency of at most 10%, at most 20%, at most 30%, at most 40%, at most 50%, at most 60%, at most 70%, at most 80%, at most 90%, or at most 100%. In yet another embodiment, a Clostridial toxin pharmaceutical composition disclosed in the present specification exhibits a recovered potency of about 20% to about 100%, about 20% to about 90%, about 20% to about 80%, about 20% to about 70%, about 20% to about 60%, or about 20% to about 50%. In still another embodiment, a Clostridial toxin pharmaceutical composition disclosed in the present specification exhibits a recovered potency of about 40% to about 100%, about 40% to about 90%, about 40% to about 80%, about 40% to about 70%, about 40% to about 60%, or about 40% to about 50%.

Aspects of the present pharmaceutical compositions provide, in part, a pharmaceutical composition form. As used herein, the term "pharmaceutical composition form" refers to whether the pharmaceutical composition is processed into a solid form or aqueous form. Processing a formulation of a pharmaceutical composition into a solid form can be achieved by, e.g., lyophilization (freeze-drying) or vacuum-drying. Processing a formulation of a pharmaceutical composition into an aqueous form can simply be achieved during the compounding stage by the addition of a solute that dissolves or suspends solid excipients to form a solution. Thus, in an embodiment, a Clostridial toxin pharmaceutical composition is in a solid form. In another embodiment, a Clostridial toxin pharmaceutical composition is in an aqueous form.

Aspects of the present pharmaceutical compositions provide, in part, storage condition of a pharmaceutical composition. As used hereon, the term "storage condition of a pharmaceutical composition" refers to the location a pharmaceutical composition is stored while in its solid form before reconstitution with an appropriate solution prior to administration. It is envisioned that any storage condition is useful for storing a Clostridial toxin pharmaceutical compositions disclosed in the present specification, with the proviso that a therapeutically effective amount of the Clostridial toxin active ingredient is recovered upon reconstitution with the appropriate solution. In an embodiment, a Clostridial toxin pharmaceutical composition disclosed in the present specification is stored at ambient temperature. In aspects of this embodiment, a Clostridial toxin pharmaceutical composition disclosed in the present specification is stored at an ambient temperature of at least 16° C., at least 18° C., at least 20° C., or at least 22° C. In other aspects of this embodiment, a Clostridial toxin pharmaceutical composition disclosed in the present specification is stored at an ambient temperature of at most 16° C., at most 18° C., at most 20° C., or at most 22° C. In yet other aspects of this embodiment, a Clostridial toxin pharmaceutical composition disclosed in the present specification is stored at an ambient temperature of about 16° C. to about 24° C., at about 16° C. to about 22° C., at about 16° C. to about 20° C., or at about 18° C. to about 24° C. In another embodiment, a Clostridial toxin pharmaceutical composition disclosed in the present specification is stored at a temperature below freezing. In aspects of this embodiment, a Clostridial toxin pharmaceutical composition disclosed in the present specification is stored at a temperature of at least 0° C., at least −20° C., at least −70° C., or at least −120° C. In other aspects of this embodiment, a Clostridial toxin pharmaceutical composition disclosed in the present specification is stored at a temperature of at most 0° C., at most −20° C., at most −70° C., or at most −120° C. In yet other aspects of this embodiment, a Clostridial toxin pharmaceutical composition disclosed in the present specification is stored at a temperature of about 0° C. to about −20° C., at about −5° C. to about −20° C., at about 0° C. to about −15° C., at about −5° C. to about −15° C., at about 0° C. to about −70° C., at about −20° C. to about −70° C., or at about −20° C. to about −120° C.

Aspects of the present pharmaceutical compositions provide, in part, a Clostridial toxin active ingredient that is stable. For purposes of the present Clostridial toxin pharmaceutical compositions, a Clostridial toxin active ingredient is stable when the recovered potency of the active ingredient when stored for a certain period of time is at least 70% of the initial recovered potency for that active ingredient. For example, a Clostridial toxin active ingredient is stable when the Clostridial toxin pharmaceutical composition containing that Clostridial toxin active ingredient demonstrates, e.g., an initial recovered potency of 100% and a recovered potency of at least 70% when tested one year later, an initial recovered potency of 90% and a recovered potency of at least 63% when tested one year later, an initial recovered potency of 80% and a recovered potency of at least 56% when tested one year later, an initial recovered potency of 70% and a recovered potency of at least 49% when tested one year later, or an initial recovered potency of 60% and a recovered potency of at least 42% when tested one year later.

Aspects of the Clostridial toxin pharmaceutical compositions disclosed in the present specification can also be described as follows:

1. A citrate-buffered, animal-protein free, solid-form Clostridial toxin pharmaceutical composition comprising a Clostridial toxin active ingredient and an effective amount of sucrose, wherein the composition is buffered to about pH 5.5, and wherein the Clostridial toxin active ingredient is stable for at least one-year when stored at either ambient or below freezing temperatures.
2. An animal-protein free, solid-form Clostridial toxin pharmaceutical composition comprising a Clostridial toxin active ingredient and an effective amount of lactose, wherein the Clostridial toxin active ingredient is stable for at least one-year when stored at either ambient or below freezing temperatures.
3. A buffered, animal-protein free, solid-form Clostridial toxin pharmaceutical composition comprising a Clostridial toxin active ingredient and an effective amount of lactose, wherein the composition is buffered to about pH 5.5, and wherein the Clostridial toxin active ingredient is stable for at least one-year when stored at either ambient or below freezing temperatures.
4. A citrate-buffered, animal-protein free, solid-form Clostridial toxin pharmaceutical composition comprising a Clostridial toxin active ingredient and an effective amount of lactose, wherein the composition is buffered to about pH 6.5, and wherein the Clostridial toxin active ingredient is stable for at least one-year when stored at below freezing temperatures.
5. An animal-protein free, solid-form Clostridial toxin pharmaceutical composition comprising a Clostridial toxin active ingredient and an effective amount of lactose in sodium chloride solution, wherein the Clostridial toxin active ingredient is stable for at least one-year when stored at below freezing temperatures.
6. A phosphate-buffered, animal-protein free, solid-form Clostridial toxin pharmaceutical composition comprising a Clostridial toxin active ingredient and an effective amount of dextran 3K, wherein the composition is buffered to about pH 6.5, and wherein the Clostridial toxin active ingredient is stable for at least one-year when stored at below freezing temperatures.
7. An animal-protein free, solid-form Clostridial toxin pharmaceutical composition comprising a Clostridial toxin active ingredient and an effective amount of PVP 17, wherein the Clostridial toxin active ingredient is stable for at least one-year when stored at below freezing temperatures.

8. A buffered, animal-protein free, solid-form Clostridial toxin pharmaceutical composition comprising a Clostridial toxin active ingredient and an effective amount of PVP 17, wherein the composition is buffered to about pH 5.5 to about pH 6.5, and wherein the Clostridial toxin active ingredient is stable for at least one-year when stored at below freezing temperatures.

9. A citrate-buffered, animal-protein free, solid-form Clostridial toxin pharmaceutical composition comprising a Clostridial toxin active ingredient and an effective amount of PVP 17, wherein the composition is buffered to about pH 5.5, and wherein the Clostridial toxin active ingredient is stable for at least one-year when stored at either ambient or below freezing temperatures.

10. An animal-protein free, solid-form Clostridial toxin pharmaceutical composition comprising a Clostridial toxin active ingredient, an effective amount of PVP 17, and an effective amount of sodium chloride, wherein the Clostridial toxin active ingredient is stable for at least one-year when stored at below freezing temperatures.

11. A citrate-buffered, animal-protein free, solid-form Clostridial toxin pharmaceutical composition comprising a Clostridial toxin active ingredient and an effective amount of PEG 3350, wherein the composition is buffered to about pH 5.5 to about pH 6.5, and wherein the Clostridial toxin active ingredient is stable for at least one-year when stored at either ambient or below freezing temperatures.

12. A histidine-buffered, animal-protein free, solid-form Clostridial toxin pharmaceutical composition comprising a Clostridial toxin active ingredient and an effective amount of PEG 3350, wherein the composition is buffered to about pH 5.5 to about pH 6.5, and wherein the Clostridial toxin active ingredient is stable for at least one-year when stored at either ambient or below freezing temperatures.

13. A citrate-buffered, animal-protein free, solid-form Clostridial toxin pharmaceutical composition comprising a Clostridial toxin active ingredient and an effective amount of Poloxamer 188, wherein the composition is buffered to about pH 5.5, and wherein the Clostridial toxin active ingredient is stable for at least one-year when stored at either ambient or below freezing temperatures.

14. A citrate-buffered, animal-protein free, solid-form Clostridial toxin pharmaceutical composition comprising a Clostridial toxin active ingredient and an effective amount of Poloxamer 188, wherein the composition is buffered to about pH 5.5 to about pH 6.5, and wherein the Clostridial toxin active ingredient is stable for at least one-year when stored at below freezing temperatures.

15. An animal-protein free, solid-form Clostridial toxin pharmaceutical composition comprising a Clostridial toxin active ingredient, an effective amount of lactose and an effective amount of sucrose, wherein the Clostridial toxin active ingredient is stable for at least one-year when stored at either ambient or below freezing temperatures.

16. A buffered, animal-protein free, solid-form Clostridial toxin pharmaceutical composition comprising a Clostridial toxin active ingredient, an effective amount of lactose and an effective amount of sucrose, wherein the composition is buffered to about pH 5.5, and wherein the Clostridial toxin active ingredient is stable for at least one-year when stored at either ambient or below freezing temperatures.

17. A phosphate-buffered, animal-protein free, solid-form Clostridial toxin pharmaceutical composition comprising a Clostridial toxin active ingredient, effective amount of lactose and an effective amount of sucrose, wherein the composition is buffered to about pH 6.5, and wherein the Clostridial toxin active ingredient is stable for at least one-year when stored at below freezing temperatures.

18. An animal-protein free, solid-form Clostridial toxin pharmaceutical composition comprising a Clostridial toxin active ingredient, an effective amount of lactose, an effective amount of sucrose and an effective amount of sodium chloride, wherein the Clostridial toxin active ingredient is stable for at least one-year when stored at either ambient or below freezing temperatures.

19. An animal-protein free, solid-form Clostridial toxin pharmaceutical composition comprising a Clostridial toxin active ingredient, an effective amount of sucrose and an effective amount of PVP 17, wherein the Clostridial toxin active ingredient is stable for at least one-year when stored at below freezing temperatures.

20. A buffered, animal-protein free, solid-form Clostridial toxin pharmaceutical composition comprising a Clostridial toxin active ingredient, an effective amount of sucrose and an effective amount of PVP 17, wherein the composition is buffered to about pH 5.5 to about pH 6.5, and wherein the Clostridial toxin active ingredient is stable for at least one-year when stored at below freezing temperatures.

21. A citrate-buffered, animal-protein free, solid-form Clostridial toxin pharmaceutical composition comprising a Clostridial toxin active ingredient, an effective amount of sucrose and an effective amount of PVP 17, wherein the composition is buffered to about pH 5.5, and wherein the Clostridial toxin active ingredient is stable for at least one-year when stored at either ambient or below freezing temperatures.

22. A phosphate-buffered, animal-protein free, solid-form Clostridial toxin pharmaceutical composition comprising a Clostridial toxin active ingredient, an effective amount of sucrose and an effective amount of PVP 17, wherein the composition is buffered to about pH 5.5 to about pH 6.5, and wherein the Clostridial toxin active ingredient is stable for at least one-year when stored at either ambient or below freezing temperatures.

23. An animal-protein free, solid-form Clostridial toxin pharmaceutical composition comprising a Clostridial toxin active ingredient, an effective amount of sucrose, an effective amount of PVP 17 and an effective amount of sodium chloride, wherein the Clostridial toxin active ingredient is stable for at least one-year when stored at either ambient or below freezing temperatures.

24. An animal-protein free, solid-form Clostridial toxin pharmaceutical composition comprising a Clostridial toxin active ingredient, an effective amount of sucrose and an effective amount of PEG 3350, wherein the Clostridial toxin active ingredient is stable for at least one-year when stored at either ambient or below freezing temperatures.

25. An animal-protein free, solid-form Clostridial toxin pharmaceutical composition comprising a Clostridial toxin active ingredient, an effective amount of lactose and an effective amount of PVP 17, wherein the Clostridial toxin active ingredient is stable for at least one-year when stored at below freezing temperatures.

26. An animal-protein free, solid-form Clostridial toxin pharmaceutical composition comprising a Clostridial toxin active ingredient, an effective amount of lactose and an effective amount of PEG 3350, wherein the Clostridial toxin active ingredient is stable for at least one-year when stored at either ambient or below freezing temperatures.

26. A citrate-buffered, animal-protein free, solid-form Clostridial toxin pharmaceutical composition comprising a Clostridial toxin active ingredient, an effective amount of lactose and an effective amount of PEG 3350, wherein the composition is buffered to about pH 5.5, and wherein the Clostridial toxin active ingredient is stable for at least one-year when stored at either ambient or below freezing temperatures.

27. An animal-protein free, solid-form Clostridial toxin pharmaceutical composition comprising a Clostridial toxin active ingredient, an effective amount of sucrose and an effective amount of Poloxamer 188, wherein the Clostridial toxin active ingredient is stable for at least one-year when stored at below freezing temperatures.

28. A buffered, animal-protein free, solid-form Clostridial toxin pharmaceutical composition comprising a Clostridial toxin active ingredient, an effective amount of sucrose and an effective amount of Poloxamer 188, wherein the composition is buffered to about pH 5.5 to about pH 6.5, and wherein the Clostridial toxin active ingredient is stable for at least one-year when stored at either ambient or below freezing temperatures.

29. An animal-protein free, solid-form Clostridial toxin pharmaceutical composition comprising a Clostridial toxin active ingredient, an effective amount of sucrose, an effective amount of Poloxamer 188, and an effective amount of sodium chloride, wherein the Clostridial toxin active ingredient is stable for at least one-year when stored at either ambient or below freezing temperatures.

30. An animal-protein free, solid-form Clostridial toxin pharmaceutical composition comprising a Clostridial toxin active ingredient, an effective amount of sucrose and an effective amount of polysorbate 80, wherein the Clostridial toxin active ingredient is stable for at least one-year when stored at below freezing temperatures.

31. An animal-protein free, solid-form Clostridial toxin pharmaceutical composition comprising a Clostridial toxin active ingredient, an effective amount of lactose and an effective amount of Poloxamer 188, wherein the Clostridial toxin active ingredient is stable for at least one-year when stored at below freezing temperatures.

32. A buffered, animal-protein free, solid-form Clostridial toxin pharmaceutical composition comprising a Clostridial toxin active ingredient, an effective amount of lactose and an effective amount of Poloxamer 188, wherein the composition is buffered to about pH 5.5 to an about pH 6.5, and wherein the Clostridial toxin active ingredient is stable for at least one-year when stored at either ambient or below freezing temperatures.

33. An animal-protein free, solid-form Clostridial toxin pharmaceutical composition comprising a Clostridial toxin active ingredient, an effective amount of lactose, an effective amount of Poloxamer 188, and an effective amount of sodium chloride, wherein the Clostridial toxin active ingredient is stable for at least one-year when stored at either ambient or below freezing temperatures.

34. A buffered, animal-protein free, solid-form Clostridial toxin pharmaceutical composition comprising a Clostridial toxin active ingredient, an effective amount of Dextran 3K and an effective amount of PEG 3350, wherein the composition is buffered to about pH 5.5 to about pH 6.5, and wherein the Clostridial toxin active ingredient is stable for at least one-year when stored at below freezing temperatures.

35. An animal-protein free, solid-form Clostridial toxin pharmaceutical composition comprising a Clostridial toxin active ingredient, an effective amount of PVP 17 and an effective amount of PEG 3350, wherein the Clostridial toxin active ingredient is stable for at least one-year when stored at below freezing temperatures.

36. A buffered, animal-protein free, solid-form Clostridial toxin pharmaceutical composition comprising a Clostridial toxin active ingredient, an effective amount of PVP 17 and an effective amount of PEG 3350, wherein the composition is buffered to about pH 5.5 to about pH 6.5, and wherein the Clostridial toxin active ingredient is stable for at least one-year when stored at below freezing temperatures.

37. An animal-protein free, solid-form Clostridial toxin pharmaceutical composition comprising a Clostridial toxin active ingredient, an effective amount of Dextran 3K and an effective amount of Poloxamer 188, wherein the Clostridial toxin active ingredient is stable for at least one-year when stored at below freezing temperatures.

38. A buffered, animal-protein free, solid-form Clostridial toxin pharmaceutical composition comprising a Clostridial toxin active ingredient, an effective amount of Dextran 3K and an effective amount of Poloxamer 188, wherein the composition is buffered to about pH 5.5 to about pH 6.5, and wherein the Clostridial toxin active ingredient is stable for at least one-year when stored at below freezing temperatures.

39. An animal-protein free, solid-form Clostridial toxin pharmaceutical composition comprising a Clostridial toxin active ingredient, an effective amount of Dextran 40K and an effective amount of Poloxamer 188, wherein the Clostridial toxin active ingredient is stable for at least one-year when stored at below freezing temperatures.

40. A buffered, animal-protein free, solid-form Clostridial toxin pharmaceutical composition comprising a Clostridial toxin active ingredient, an effective amount of Dextran 40K and an effective amount of Poloxamer 188, wherein the composition is buffered to about pH 5.5 to about pH 6.5, and wherein the Clostridial toxin active ingredient is stable for at least one-year when stored at below freezing temperatures.

41. An animal-protein free, solid-form Clostridial toxin pharmaceutical composition comprising a Clostridial toxin active ingredient, an effective amount of PVP 17 and an effective amount of Poloxamer 188, wherein the Clostridial toxin active ingredient is stable for at least one-year when stored at below freezing temperatures.

42. A buffered, animal-protein free, solid-form Clostridial toxin pharmaceutical composition comprising a Clostridial toxin active ingredient, an effective amount of PVP 17 and an effective amount of Poloxamer 188, wherein the composition is buffered to about pH 5.5 to about pH 6.5, and wherein the Clostridial toxin active ingredient is stable for at least one-year when stored at below freezing temperatures.

43. An animal-protein free, solid-form Clostridial toxin pharmaceutical composition comprising a Clostridial toxin active ingredient, an effective amount of PVP 17, an effective amount of Poloxamer 188, and an effective amount of sodium chloride, wherein the Clostridial toxin active ingredient is stable for at least one-year when stored at below freezing temperatures.

44. A citrate-buffered, animal-protein free, solid-form Clostridial toxin pharmaceutical composition comprising a Clostridial toxin active ingredient, an effective amount of PEG 3350 and an effective amount of Poloxamer 188, wherein the composition is buffered to about pH 5.5 to about pH 6.5, and wherein the Clostridial toxin active ingredient is stable for at least one-year when stored at below freezing temperatures.

45. A phosphate-buffered, animal-protein free, solid-form Clostridial toxin pharmaceutical composition comprising a Clostridial toxin active ingredient, an effective amount of PEG 3350 and an effective amount of Poloxamer 188, wherein the composition is buffered to about pH 5.5, and wherein the Clostridial toxin active ingredient is stable for at least one-year when stored at below freezing temperatures.

46. A histidine-buffered, animal-protein free, solid-form Clostridial toxin pharmaceutical composition comprising a Clostridial toxin active ingredient, an effective amount of PEG 3350 and an effective amount of Poloxamer 188, wherein the composition is buffered to about pH 5.5 to about pH 6.5, and wherein the Clostridial toxin active ingredient is stable for at least one-year when stored at either ambient or below freezing temperatures.

47. An animal-protein free, solid-form Clostridial toxin pharmaceutical composition comprising a Clostridial toxin active ingredient, an effective amount of PVP 17 and an effective amount of Polysorbate 80, wherein the Clostridial toxin active ingredient is stable for at least one-year when stored at below freezing temperatures.

48. An animal-protein free, solid-form Clostridial toxin pharmaceutical composition comprising a Clostridial toxin active ingredient, an effective amount of sucrose, an effective amount of PVP 17 and an effective amount of Poloxamer 188, wherein the Clostridial toxin active ingredient is stable for at least one-year when stored at below freezing temperatures.

49. A buffered, animal-protein free, solid-form Clostridial toxin pharmaceutical composition comprising a Clostridial toxin active ingredient, an effective amount of sucrose, an effective amount of PVP 17 and an effective amount of Poloxamer 188, wherein the composition is buffered to about pH 5.5 to about pH 6.5, and wherein the Clostridial toxin active ingredient is stable for at least one-year when stored at below freezing temperatures.

50. A phosphate-buffered, animal-protein free, solid-form Clostridial toxin pharmaceutical composition comprising a Clostridial toxin active ingredient, an effective amount of sucrose, an effective amount of PVP 17 and an effective amount of Poloxamer 188, wherein the composition is buffered to about pH 5.5 to about pH 6.5, and wherein the Clostridial toxin active ingredient is stable for at least one-year when stored at either ambient or below freezing temperatures.

51. An animal-protein free, solid-form Clostridial toxin pharmaceutical composition comprising a Clostridial toxin active ingredient, an effective amount of sucrose, an effective amount of PVP 17, an effective amount of Poloxamer 188, and an effective amount of sodium chloride, wherein the Clostridial toxin active ingredient is stable for at least one-year when stored at either ambient or below freezing temperatures.

52. An animal-protein free, solid-form Clostridial toxin pharmaceutical composition comprising a Clostridial toxin active ingredient, an effective amount of sucrose, an effective amount of lactose and an effective amount of Poloxamer 188, wherein the Clostridial toxin active ingredient is stable for at least one-year when stored at either ambient or below freezing temperatures.

53. A buffered, animal-protein free, solid-form Clostridial toxin pharmaceutical composition comprising a Clostridial toxin active ingredient, an effective amount of sucrose, an effective amount of lactose and an effective amount of Poloxamer 188, wherein the composition is buffered to about pH 5.5 to about pH 6.5, and wherein the Clostridial toxin active ingredient is stable for at least one-year when stored at either ambient or below freezing temperatures.

54. An animal-protein free, solid-form Clostridial toxin pharmaceutical composition comprising a Clostridial toxin active ingredient, an effective amount of sucrose, an effective amount of PVP 17 and an effective amount of PEG 3350, wherein the Clostridial toxin active ingredient is stable for at least one-year when stored at either ambient or below freezing temperatures.

55. An animal-protein free, solid-form Clostridial toxin pharmaceutical composition comprising a Clostridial toxin active ingredient, an effective amount of lactose, an effective amount of PEG 3350 and an effective amount of Poloxamer 188, wherein the Clostridial toxin active ingredient is stable for at least one-year when stored at either ambient or below freezing temperatures.

56. An animal-protein free, solid-form Clostridial toxin pharmaceutical composition comprising a Clostridial toxin active ingredient, an effective amount of Dextran 3K, an effective amount of PEG 3350 and an effective amount of Poloxamer 188, wherein the Clostridial toxin active ingredient is stable for at least one-year when stored at either ambient or below freezing temperatures.

57. A buffered, animal-protein free, solid-form Clostridial toxin pharmaceutical composition comprising a Clostridial toxin active ingredient, an effective amount of Dextran 3K, an effective amount of PEG 3350 and an effective amount of Poloxamer 188, wherein the composition is buffered to about pH 5.5 to about pH 6.5, and wherein the Clostridial toxin active ingredient is stable for at least one-year when stored at either ambient or below freezing temperatures.

57. An animal-protein free, solid-form Clostridial toxin pharmaceutical composition comprising a Clostridial toxin active ingredient, an effective amount of PVP 17, an effective amount of PEG 3350 and an effective amount of Poloxamer 188, wherein the Clostridial toxin active ingredient is stable for at least one-year when stored at either ambient or below freezing temperatures.

58. A buffered, animal-protein free, solid-form Clostridial toxin pharmaceutical composition comprising a Clostridial toxin active ingredient, an effective amount of PVP 17, an effective amount of PEG 3350 and an effective amount of Poloxamer 188, wherein the composition is buffered to about pH 5.5 to about pH 6.5, and wherein the Clostridial toxin active ingredient is stable for at least one-year when stored at either ambient or below freezing temperatures.

58. An animal-protein free, solid-form Clostridial toxin pharmaceutical composition comprising a Clostridial toxin active ingredient, an effective amount of PVP 17, an effective amount of glycine and an effective amount of Poloxamer 188, wherein the Clostridial toxin active ingredient is stable for at least one-year when stored at either ambient or below freezing temperatures.

59. An animal-protein free, solid-form Clostridial toxin pharmaceutical composition comprising a Clostridial toxin active ingredient, an effective amount of a sugar excipient and an effective amount of surfactant excipient.

60. The composition according to 59, wherein the sugar excipient is a monosaccharide, a disaccharide or a trisaccharide.

61. The composition according to 59, wherein the surfactant excipient is a poloxamer, a polysorbate, a polyoxyethylene glycol dodecyl ether, or a polyoxyethylene octyl phenyl ether.

62. The composition according to 59, wherein the Clostridial toxin active ingredient is stable for at least one-year when stored at either ambient or below freezing temperatures.

63. The composition according to 59, wherein the composition is buffered to about pH 5.5 to about pH 6.5.

64. The composition according to 63, wherein the composition is buffered using a citrate buffer, a phosphate buffer or a histidine buffer.

65. The composition according to 59, wherein the composition further comprises an effective amount of sodium chloride.

66. The composition according to 59, wherein the composition further comprises an effective amount of a non-protein polymer excipient.

67. The composition according to 66, wherein the non-protein polymer excipient is a dextran, a polyethylene glycol, a polyethylene imine, a polyvinyl pyrrolidone, a polyvinyl acetate, an inulin, a starch, or a starch derivative.

68. An animal-protein free, solid-form Clostridial toxin pharmaceutical composition comprising a Clostridial toxin active ingredient, an effective amount of a non-protein polymer excipient and an effective amount of surfactant excipient.

69. The composition according to 68, wherein the non-protein polymer excipient is a dextran, a polyethylene glycol, a polyethylene imine, a polyvinyl pyrrolidone, a polyvinyl acetate, an inulin, a starch, or a starch derivative.

70. The composition according to 68, wherein the surfactant excipient is a poloxamer, a polysorbate, a polyoxyethylene glycol dodecyl ether, or a polyoxyethylene octyl phenyl ether.

71. The composition according to 68, wherein the Clostridial toxin active ingredient is stable for at least one-year when stored at either ambient or below freezing temperatures.

72. The composition according to 68, wherein the composition is buffered to about pH 5.5 to about pH 6.5.

73. The composition according to 72, wherein the composition is buffered using a citrate buffer, a phosphate buffer or a histidine buffer.

74. The composition according to 68, wherein the composition further comprises an effective amount of sodium chloride.

75. An animal-protein free, solid-form Clostridial toxin pharmaceutical composition comprising a Clostridial toxin active ingredient, an effective amount of a first non-protein polymer excipient, an effective amount of a second non-protein polymer excipient, and an effective amount of surfactant excipient.

76. The composition according to 75, wherein the first non-protein polymer excipient is a dextran, a polyethylene glycol, a polyethylene imine, a polyvinyl pyrrolidone, a polyvinyl acetate, an inulin, a starch, or a starch derivative.

77. The composition according to 75, wherein the second non-protein polymer excipient is a dextran, a polyethylene glycol, a polyethylene imine, a polyvinyl pyrrolidone, a polyvinyl acetate, an inulin, a starch, or a starch derivative.

78. The composition according to 75, wherein the surfactant excipient is a poloxamer, a polysorbate, a polyoxyethylene glycol dodecyl ether, or a polyoxyethylene octyl phenyl ether.

79. The composition according to 75, wherein the Clostridial toxin active ingredient is stable for at least one-year when stored at either ambient or below freezing temperatures.

80. The composition according to 75, wherein the composition is buffered to about pH 5.5 to about pH 6.5.

81. The composition according to 80, wherein the composition is buffered using a citrate buffer, a phosphate buffer or a histidine buffer.

82. The composition according to 75, wherein the composition further comprises an effective amount of sodium chloride.

83. The composition according to 1-82, wherein the Clostridial toxin active ingredient is a Clostridial toxin complex, a Clostridial toxin, a modified Clostridial toxin or a re-targeted Clostridial toxin.

84. The composition according to 83, wherein the Clostridial toxin complex is a BoNT/A complex, a BoNT/B complex, a BoNT/C, complex, a BoNT/D complex, a BoNT/E complex, a BoNT/F complex, a BoNT/G complex, a TeNT complex, a BaNT complex, or a BuNT complex.

85. The composition according to 83, wherein the Clostridial toxin complex is a 900-kDa BoNT/A complex, a 500-kDa BoNT/A complex, a 300-kDa BoNT/A complex, a 500-kDa BoNT/B complex, a 500-kDa BoNT/C1 complex, a 500-kDa BoNT/D complex, a 300-kDa BoNT/D complex, a 300-kDa BoNT/E complex, or a 300-kDa BoNT/F complex.

86. The composition according to 83, wherein the Clostridial toxin is a BoNT/A, a BoNT/B, a BoNT/$C_1$, a BoNT/D, a BoNT/E, a BoNT/F, a BoNT/G, a TeNT, a BaNT, or a BuNT.

87. The composition according to 83, wherein the BoNT/A is a BoNT/A1, a BoNT/A2, a BoNT/A3, a BoNT/A4, or a BoNT/A5.

88. The composition according to 83, wherein the re-targeted Clostridial toxin is a re-targeted BoNT/A, a re-targeted BoNT/B, a re-targeted BoNT/C1, a re-targeted BoNT/D, a re-targeted BoNT/E, a re-targeted BoNT/F, a re-targeted BoNT/G, a re-targeted TeNT, a re-targeted BaNT, or a re-targeted BuNT.

89. The composition according to 83, wherein the re-targeted Clostridial toxin comprises an opioid targeting moiety, a tachykinin targeting moiety, a melanocortin targeting moiety, a granin targeting moiety, a Neuropeptide Y related peptide targeting moiety, a neurohormone targeting moiety, a neuroregulatory cytokine targeting moiety, a kinin peptide targeting moiety, a fibroblast growth factor targeting moiety, a nerve growth factor targeting moiety, an insulin growth factor targeting moiety, an epidermal growth factor targeting moiety, a vascular endothelial growth factor targeting moiety, a brain derived neurotrophic factor targeting moiety, a growth derived neurotrophic factor targeting moiety, a neurotrophin targeting moiety, a head activator peptide targeting moiety, a neurturin targeting moiety, a persephrin targeting moiety, an artemin targeting moiety, a transformation growth factor β targeting moiety, a bone morphogenic protein targeting moiety, a growth differentiation factor targeting moiety, an activin targeting moiety, a glucagon like hormone targeting moiety, a pituitary adenylate cyclase activating peptide targeting moiety, a growth hormone-releasing hormone targeting moiety, vasoactive intestinal peptide targeting moiety, a gastric inhibitory polypeptide targeting moiety, a calcitonin-related peptidesvisceral gut peptide targeting moiety, or a PAR peptide targeting moiety.

90. The composition according to 89, wherein the opioid targeting moiety is an enkephalin, an endomorphin, an endorphin, a dynorphin, a nociceptin or a hemorphin.

91. The composition according to 89, wherein the tachykinin targeting moiety is a Substance P, a neuropeptide K, a neuropeptide gamma, a neurokinin A, a neurokinin B, a hemokinin or a endokinin.

EXAMPLES

The following examples set forth specific embodiments of the present Clostridial toxin pharmaceutical compositions and are not intended to limit the scope of the invention.

Example 1

Non-Protein Stabilized Formulations—One Excipient

Experiments were carried out to determine the effects of formulations comprising a single non-protein excipient on Clostridial toxin active ingredient recovery after reconstitution. The non-protein excipients tested were added separately or in combination with the listed buffers or salts (Table 2). All of the formulations were compounded, lyophilized, reconstituted and potency assessed in the same manner, and with the same Clostridial toxin active ingredient used in each formulation, except that each formulation was prepared with different non-protein excipient or with different amounts of the non-protein excipient.

Formulations were compounded by first adding the indicated amount of the non-protein excipient(s) to sterile water to form a solution. Next the Clostridial toxin active ingredient was added to the solution to produce the formulation. The Clostridial toxin active ingredient added was about 150 units of a 900-kDaBoNT/A complex, about 150 units of a 150 kDa BoNT/A, or about 250 ng of a 100 kDa re-targeted BoNT/A, where the modification was the substitution of the BoNT/A binding domain with an opioid ligand, see e.g., Steward, L. E. et al., Modified Clostridial Toxins with Enhanced Translocation Capabilities and Altered Targeting Activity For Non-Clostridial Toxin Target Cells, U.S. patent application Ser. No. 11/776,075 (Jul. 11, 2007); Dolly, J. O. et al., Activatable Clostridial Toxins, U.S. patent application Ser. No. 11/829,475 (Jul. 27, 2007); Foster, K. A. et al., Fusion Proteins, International Patent Publication WO 2006/059093 (Jun. 8, 2006); and Foster, K. A. et al., Non-Cytotoxic Protein Conjugates, International Patent Publication WO 2006/059105 (Jun. 8, 2006), each of which is incorporated by reference in its entirety. The formulations were processed into solid forms (either by lyophilization or vacuum drying), stored for a specified period of time (about one-day, at least three months or at least one year), reconstitution with either sterile water or a specified buffer, and then assayed to determine the recovered potency of the Clostridial toxin active ingredient.

To determine the recovered potency of a Clostridial toxin, Clostridial toxin complex or modified Clostridial toxin, the reconstituted formulation was assayed by a mouse $LD_{50}$ bioassay. For each reconstituted formulation, a minimum of six serial dilutions at 1.33 dose intervals were prepared in normal saline and typically five or six mice (female Swiss Weber weighing between 17-22 grams) were used in each dosage group. The mice were injected intraperitoneally into the lower right abdomen and the death rates over the ensuing 72 hours for each dilution were recorded. The dilutions were prepared so that the most concentrated dilution produces a death rate of at least 80% of the mice injected, and the least concentration dilution produces a death rate no greater than 20% of the mice injected. A minimum of four dilutions must fall within the monotone decreasing range of the death rates, i.e., the two largest and the two smallest rates must be decreasing (not equivalent). The monotone decreasing range commences with a death rate of no less than 80%. Two reference standard assays are carried out concurrently. The dilution at which 50% of the mice die within the three day post injection observation period is defined as a dilution which comprises one unit (1 U) of the botulinum toxin. The mouse $LD_{50}$ bioassay provides a determination of the potency of a Clostridial toxin, Clostridial toxin complex or modified Clostridial toxin in terms of its mouse 50% lethal dose or "$LD_{50}$." Thus, one unit (U) of a Clostridial toxin, Clostridial toxin complex or modified Clostridial toxin is defined as the amount of toxin which upon intraperitoneal injection killed 50% of the mice injected, i.e., $LD_{50}$.

Recovery is expressed as a percentage and is calculated by dividing the potency of the Clostridial toxin active ingredient in the stored reconstitution formulation by the potency of the active Clostridial toxin ingredient determined prior to its addition into the test solution. Thus, for example, a recovery of 60% means that the potency of the Clostridial toxin active ingredient after reconstitution was 60% of the potency of the Clostridial toxin active ingredient prior to its addition to the formulation. The maximum theoretical recovered potency is 100%. The results show that, in general, a Clostridial toxin pharmaceutical composition comprising a Clostridial toxin complex was poorly stabilized when the formulation comprised a single non-protein excipient (Table 2).

When the single excipient used was a sugar, only the disaccharide lactose exhibited any degree of initial recovered potency, showing about 15% to about 41% recovery of the Clostridial toxin active ingredient when about 10 mg to about 50 mg of lactose was added (about 1% (w/v) to about 5% (w/v)) (Table 2). Furthermore, although exhibiting recovery, the test formulations containing lactose as the single excipient did not appear very stable after one year in storage since recovered potency was not detected at this time for any amount tested except for 20 mg lactose (Table 2). Addition of 10 mM sodium citrate (pH 5.5) and potassium phosphate (pH 5.5) improved both initial recovered potency and long-term stability of the Clostridial toxin active ingredient in Clostridial toxin pharmaceutical compositions containing lactose as the single excipient. Initial recovered potency increased from about 41% to about 60% when the lactose formulation comprised 10 mM sodium citrate (pH 5.5) and increased from about 41% to about 71% when the lactose formulation comprised 10 mM potassium phosphate (pH 5.5) (Table 2). In addition, increased recovered potency of the Clostridial toxin active ingredient was also observed after at least one-year of storage using either pH 5.5 buffer, as opposed to water, in Clostridial toxin pharmaceutical compositions stored at ambient or freezing temperatures (Table 2). However, addition of 10 mM sodium citrate (pH 6.5) to Clostridial toxin pharmaceutical compositions containing lactose as the single excipient did not improve either initial recovered potency or long-term stability of the Clostridial toxin active ingredient (Table 2). Surprisingly, addition of 10 mM potassium phosphate (pH 6.5) to Clostridial toxin pharmaceutical compositions containing lactose as the single excipient actually eliminated recovery of the Clostridial toxin active ingredient altogether (Table 2). Lastly, the addition of 10 mM sodium chloride to Clostridial toxin pharmaceutical compositions containing lactose as the single excipient did not improve either recovered potency or long-term stability of the Clostridial toxin active ingredient (Table 2).

The disaccharides sucrose and trehalose and the trisaccharide raffinose showed no recovered potency of the Clostridial toxin active ingredient whatsoever when used as the single excipient. Furthermore, with one exception, the addition of buffers or sodium chloride to Clostridial toxin pharmaceutical compositions containing these sugars as the single excipient did not improve either initial recovered potency or long-term stability of the Clostridial toxin active ingredient (Table 2). The single exception was the Clostridial toxin pharmaceutical composition comprising sucrose and 10 mM sodium citrate (pH 5.5). This formulation exhibited 44% initial recovered potency of the Clostridial toxin active ingredient and this degree of recover was maintained for at least one year when stored at either ambient or freezing temperatures (Table 2).

Clostridial toxin pharmaceutical compositions containing a polyol (mannitol) as the single excipient did not exhibit any recovered potency (Table 2). Addition of buffers or sodium chloride to Clostridial toxin pharmaceutical compositions containing mannitol as the single excipient did not improve either recovered potency or long-term stability of the Clostridial toxin active ingredient (Table 2).

When the single excipient used was a non-protein polymer, recovered potency of the Clostridial toxin active ingredient dependent on the both type of non-protein polymer used and the specific buffer added. For example, Dextran 3K and Dextran 40K showed no initial recovered potency of the Clostridial toxin active ingredient whatsoever when used as the single excipient. On the other hand, the addition of about 60 mg of PEG 3350 (about 2% (w/v)) resulted in an initial recovered potency of about 47%. Similarly the addition of about 5 mg to about 20 mg of PVP 17 (about 0.5% (w/v) to about 2% (w/v)) resulted in an initial recovered potency of about 39% to about 52% (Table 2).

In general, the addition various buffers did not improve the initial recovered potency of the Clostridial toxin active ingredient when Dextran 3K or Dextran 40K was used as the single excipient. The sole exception was a Clostridial toxin pharmaceutical compositions comprising dextran 3K in 10 mM potassium phosphate (pH 5.5), where initial recovered potency increased from 0% to about 66%, a recovered potency that was maintained for at least one year. Surprisingly, the addition various buffers dramatically improved both recovered potency and long-term stability of the Clostridial toxin active ingredient when PEG 3350 or PVP 17 was used as the single excipient. For example, in Clostridial toxin pharmaceutical compositions comprising PEG 3350, the addition of 10 mM sodium citrate (pH 5.5) increased recovered potency from 0% to about 76%; the addition of 10 mM potassium phosphate (pH 5.5) increased recovered potency from 0% to about 80%; and the addition of 10 mM histidine buffer (pH 5.5) increased recovered potency from 0% to about 72% (Table 2). In all cases, the addition of these various buffers resulted in long-term stability of at least one-year both at ambient and freezing temperatures.

TABLE 2

Formulations using Botulinum Neurotoxin Complex[a] - One Excipient

| Excipient 1 | | | | Recovered Potency[b] (%) | | | | |
| | | | | Ambient Temperature[c] | | | Below Freezing Temperature[d] | |
| Type | Amount (mg) | Ratio | Solution (pH) | Initial | 3 months | 12 months | 3 months | 12 months |
| --- | --- | --- | --- | --- | --- | --- | --- | --- |
| Sucrose | 5 | — | Water (pH 5.6) | 0 | 0 | 0 | 0 | 0 |
| Sucrose | 10 | — | Water (pH 5.6) | 0 | 0 | 0 | 0 | 0 |
| Sucrose | 20 | — | Water (pH 5.6) | 0 | 0 | 0 | 0 | 0 |
| Sucrose | 30 | — | Water (pH 5.3) | 0 | 0 | 0 | 0 | 0 |
| Sucrose | 50 | — | Water (pH 5.6) | 0 | 0 | 0 | 0 | 0 |
| Sucrose | 100 | — | Water (pH 5.6) | 0 | 0 | 0 | 0 | 0 |
| Sucrose | 250 | — | Water (pH 5.6) | 0 | 0 | 0 | 0 | 0 |
| Sucrose | 20 | — | 10 mM SC (pH 5.5) | 44 | 44 | 44 | 39 | 49 |
| Sucrose | 20 | — | 10 mM SC (pH 6.5) | 0 | 0 | 0 | 0 | 0 |
| Sucrose | 20 | — | 10 mM PP (pH 5.5) | 0 | 0 | 0 | 0 | 0 |
| Sucrose | 20 | — | 10 mM PP (pH 6.5) | 0 | 0 | 0 | 0 | 0 |
| Sucrose | 20 | — | 10 mM NaCl (pH 5.5) | 0 | 0 | 0 | 0 | 0 |
| Sucrose | 30 | — | 10 mM NaCl (pH 5.4) | 0 | 0 | 0 | 0 | 0 |
| Sucrose | 60 | — | 10 mM NaCl (pH 5.3) | 46 | 0 | 0 | 46 | 46 |
| Lactose | 5 | — | Water (pH 4.8) | 0 | 0 | 0 | 0 | 0 |
| Lactose | 10 | — | Water (pH 4.8) | 15 | | | | |
| Lactose | 20 | — | Water (pH 4.8) | 41 | 45 | 38 | 38 | 51 |
| Lactose | 50 | — | Water (pH 4.8) | 35 | | | | |
| Lactose | 20 | — | 10 mM SC (pH 5.5) | 60 | 55 | 55 | 85 | 67 |
| Lactose | 20 | — | 10 mM SC (pH 6.5) | 45 | 0 | 0 | 49 | 49 |
| Lactose | 20 | — | 10 mM PP (pH 5.5) | 71 | 46 | 49 | 58 | 55 |
| Lactose | 20 | — | 10 mM PP (pH 6.5) | 0 | 0 | 0 | 0 | 0 |
| Lactose | 20 | — | 10 mM NaCl (pH 4.8) | 39 | 50 | 0 | 58 | — |
| Trehalose | 5 | — | Water | 0 | 0 | 0 | 0 | 0 |
| Trehalose | 10 | — | Water | 0 | 0 | 0 | 0 | 0 |
| Trehalose | 50 | — | Water | 0 | 0 | 0 | 0 | 0 |
| Raffinose | 5 | — | Water | 0 | 0 | 0 | 0 | 0 |
| Raffinose | 10 | — | Water | 0 | 0 | 0 | 0 | 0 |
| Raffinose | 50 | — | Water | 0 | 0 | 0 | 0 | 0 |
| Mannitol | 5 | — | Water | 0 | 0 | 0 | 0 | 0 |

TABLE 2-continued

Formulations using Botulinum Neurotoxin Complex[a] - One Excipient

| Excipient 1 | | | | Recovered Potency[b] (%) | | | | |
| --- | --- | --- | --- | --- | --- | --- | --- | --- |
| | | | | Ambient Temperatrue[c] | | | Below Frerezing Temperature[d] | |
| Type | Amount (mg) | Ratio | Solution (pH) | Initial | 3 months | 12 months | 3 months | 12 months |
| Mannitol | 10 | — | Water | 0 | 0 | 0 | 0 | 0 |
| Mannitol | 20 | — | Water | 0 | 0 | 0 | 0 | 0 |
| Mannitol | 50 | — | Water | 0 | 0 | 0 | 0 | 0 |
| Mannitol | 20 | — | 10 mM PP (pH 5.5) | 0 | 0 | 0 | 0 | 0 |
| Inulin | 5 | — | Water | 0 | 0 | 0 | 0 | 0 |
| Inulin | 10 | — | Water | 0 | 0 | 0 | 0 | 0 |
| Inulin | 50 | — | Water | 0 | 0 | 0 | 0 | 0 |
| Detran 3K | 60 | — | Water (pH 5.2) | 0 | 0 | 0 | 0 | 0 |
| Detran 3K | 60 | — | 10 mM SC (pH 5.5) | 0 | 0 | 0 | 0 | 0 |
| Detran 3K | 60 | — | 10 mM SC (pH 6.5) | 0 | 0 | 0 | 0 | 0 |
| Detran 3K | 60 | — | 10 mM PP (pH 5.5) | 66 | 0 | 0 | 66 | 73 |
| Detran 3K | 60 | — | 10 mM PP (pH 6.5) | 0 | 0 | 0 | 0 | 0 |
| Detran 3K | 60 | — | 10 mM HB (pH 5.5) | 0 | 0 | 0 | 0 | 0 |
| Detran 3K | 60 | — | 10 mM HB (pH 6.5) | 0 | 0 | 0 | 0 | 0 |
| Detran 40K | 60 | — | Water (pH 5.2) | 0 | 0 | 0 | 0 | 0 |
| Detran 40K | 60 | — | 10 mM SC (pH 5.5) | 0 | 0 | 0 | 0 | 0 |
| Detran 40K | 60 | — | 10 mM SC (pH 6.5) | 0 | 0 | 0 | 0 | 0 |
| Detran 40K | 60 | — | 10 mM PP (pH 5.5) | 0 | 0 | 0 | 0 | 0 |
| Detran 40K | 60 | — | 10 mM PP (pH 6.5) | 0 | 0 | 0 | 0 | 0 |
| Detran 40K | 60 | — | 10 mM HB (pH 5.5) | 0 | 0 | 0 | 0 | 0 |
| Detran 40K | 60 | — | 10 mM HB (pH 6.5) | 0 | 0 | 0 | 0 | 0 |
| PVP 17 | 0.5 | — | Water (pH 4.2) | 0 | 0 | 0 | 0 | 0 |
| PVP 17 | 5 | — | Water (pH 4.2) | 48 | — | — | — | — |
| PVP 17 | 10 | — | Water (pH 4.2) | 52 | — | — | — | — |
| PVP 17 | 20 | — | Water (pH 4.2) | 43 | 0 | 0 | 55 | 52 |
| PVP 17 | 30 | — | Water (pH 4.0) | 0 | 0 | 0 | 0 | 0 |
| PVP 17 | 50 | — | Water (pH 4.2) | 0 | 0 | 0 | 0 | 0 |
| PVP 17 | 60 | — | Water (pH 4.0) | 55 | 0 | 0 | 46 | 46 |
| PVP 17 | 100 | — | Water (pH 4.2) | 0 | 0 | 0 | 0 | 0 |
| PVP 17 | 250 | — | Water (pH 4.2) | 0 | 0 | 0 | 0 | 0 |
| PVP 17 | 20 | — | 10 mM SC (pH 5.5) | 113 | 70 | 41 | 101 | 115 |
| PVP 17 | 20 | — | 10 mM SC (pH 6.5) | 81 | 44 | 0 | 88 | 58 |
| PVP 17 | 20 | — | 10 mM PP (pH 5.5) | 79 | 0 | 0 | 75 | 73 |
| PVP 17 | 20 | — | 10 mM PP (pH 6.5) | 83 | 0 | 0 | 69 | 69 |
| PVP 17 | 60 | — | 10 mM NaCl (pH 3.1) | 100 | 0 | 0 | 100 | 100 |
| PVP 17 | 20 | — | 10 mM NaCl (pH 4.2) | 44 | 0 | 0 | 44 | — |
| PVP 17 | 30 | — | 10 mM NaCl (pH 4.0) | 46 | — | — | 58 | 62 |
| PEG 3350 | 60 | — | Water (pH 7.0) | 47 | 0 | 0 | 47 | 47 |
| PEG 3350 | 50 | — | Water (pH 7.0) | 0 | 0 | 0 | 0 | 0 |
| PEG 3350 | 60 | — | 10 mM SC (pH 5.5) | 76 | 58 | 0 | 87 | 82 |
| PEG 3350 | 60 | — | 10 mM SC (pH 6.5) | 57 | 0 | 0 | 57 | 66 |
| PEG 3350 | 60 | — | 10 mM PP (pH 5.5) | 80 | 0 | 0 | 70 | 97 |
| PEG 3350 | 60 | — | 10 mM PP (pH 6.5) | 0 | 0 | 0 | 0 | 0 |
| PEG 3350 | 60 | — | 10 mM HB (pH 5.5) | 72 | 97 | 87 | 110 | 74 |
| PEG 3350 | 60 | — | 10 mM HB (pH 6.5) | 73 | 73 | 76 | 59 | 62 |
| Poloxamer 188 | 50 | — | Water | 0 | 0 | 0 | 0 | 0 |
| Poloxamer 188 | 20 | — | Water (pH 6.5) | 0 | 0 | 0 | 0 | 0 |
| Poloxamer 188 | 20 | — | 10 mM SC (pH 5.5) | 81 | 73 | 67 | 87 | 97 |
| Poloxamer 188 | 20 | — | 10 mM SC (pH 6.5) | 56 | 0 | 0 | 50 | 38 |
| Poloxamer 188 | 20 | — | 10 mM PP (pH 5.5) | 39 | 0 | 0 | 0 | 0 |
| Poloxamer 188 | 20 | — | 10 mM PP (pH 6.5) | 0 | 0 | 0 | 0 | 0 |
| Poloxamer 188 | 20 | — | 10 mM NaCl (pH 6.4) | 0 | 0 | 0 | 0 | 0 |
| Glycine | 5 | — | Water | 0 | 0 | 0 | 0 | 0 |
| Glycine | 10 | — | Water | 0 | 0 | 0 | 0 | 0 |
| Glycine | 50 | — | Water | 0 | 0 | 0 | 0 | 0 |

[a]Amount of botulinum neurotoxin serotype A complex added per formulation was 150 units. Total volume of formulation was 1.0 mL.
[b]Recovery is expressed as a percentage and is calculated by dividing the potency of the active ingredient determined after reconstitution divided by the potency of the active ingredient determined before addition to the formulation. 3 months refers to the length of time a formulation was minimally stored at the indicated temperature. 12 months refers to the length of time a formulation was minimally stored at the indicated temperature.
[c]Ambient temperature is between about 18° C. to about 22° C.
[d]Below freezing temperature is between about −5° C. to about −20° C.

Similar, but more complex results were observed in Clostridial toxin pharmaceutical compositions comprising PVP 17 as the single excipient. For example, in Clostridial toxin pharmaceutical compositions comprising PVP 17, the addition of 10 mM sodium citrate (pH 5.5) increased initial recovered potency from about 43% to about 113%; the addition of 10 mM sodium citrate (pH 6.5) increased initial recovered potency from about 43% to about 81%; the addition of 10 mM potassium phosphate (pH 5.5) increased initial recovered potency from about 43% to about 97%; and the addition of 10 mM potassium phosphate (pH 5.5) increased initial recovered potency from about 43% to about 83%. However, while all buffers tested exhibited increased recovered potency of the Clostridial toxin active ingredient, only the addition of the sodium citrate buffers resulted in long-term stability of at least one year. Lastly, the addition of 10 mM sodium chloride to pharmaceutical compositions containing PVP 17 as the single excipient did not improve either initial recovered potency or long-term stability of the Clostridial toxin active ingredient.

When the single excipient used was a surfactant, recovered potency of the Clostridial toxin active ingredient dependent was not detected. In addition, use of various buffers resulted in mixed recovered potency. For example, in Clostridial toxin pharmaceutical compositions comprising Poloxamer 188, the addition of 10 mM sodium citrate (pH 5.5) increased initial recovered potency from 0% to about 81%; the addition of 10 mM sodium citrate (pH 6.5) increased initial recovered potency from 0% to about 56%; and the addition of 10 mM potassium phosphate (pH 5.5) increased initial recovered potency from 0% to about 39%; but the addition of 10 mM potassium phosphate (pH 6.5) did not improve recovery at all (Table 2). However, only the addition of 10 mM sodium citrate (pH 5.5) resulted in long-term stability of the Clostridial toxin active ingredient stored at either ambient or freezing temperatures (Table 2).

Thus, generally, Clostridial toxin pharmaceutical compositions comprising a single excipient does not result in significant recovered potency of the Clostridial toxin active ingredient, especially when such compositions ate stored for at least one year. Surprisingly, however, both the addition of a buffer to the Clostridial toxin pharmaceutical composition can result in both improved recovered potency and increased long-term stability of the Clostridial toxin active ingredient. However, the pairing of a particular excipient with a specific buffer can only be determined empirically.

Example 2

Non-Protein Stabilized Formulations—Two Excipients

Experiments were carried out to determine the effects of formulations comprising two different non-protein excipients on Clostridial toxin active ingredient recovery after reconstitution. The non-protein excipients tested were added separately or in combination with the listed buffers or salts (Tables 3-5). All of the formulations were compounded, lyophilized, reconstituted and potency assessed in the same manner, and with the same Clostridial toxin active ingredient used in each formulation, except that each formulation was prepared with different non-protein excipients or with different amounts of the non-protein excipients.

The tested formulations were compounded, processed, stored and reconstituted as described in Example 1. Recovered potency was determined using the mouse $LD_{50}$ bioassay described in Example 1. Recovery is expressed as a percentage and is calculated by dividing the potency of the Clostridial toxin active ingredient in the stored reconstitution formulation by the potency of the active Clostridial toxin ingredient determined prior to its addition into the test solution. The results show that a Clostridial toxin pharmaceutical composition comprising a Clostridial toxin complex could be stabilized when the formulation comprised two non-protein excipients (Tables 3-5).

Clostridial toxin pharmaceutical compositions comprising two different sugars yielded mixed results. For example, Clostridial toxin pharmaceutical compositions comprising lactose and sucrose did not appear to dramatically improve recovered potency. For example, compositions comprising about 5% (w/v) lactose resulted in an initial recovered potency of about 35% (Table 2), compositions comprising about 5% (w/v) sucrose resulted in no recovered potency (Table 2), and compositions comprising about 5% (w/v) lactose and about 5% (w/v) sucrose resulted in an initial recovered potency of about 27% (Table 3). Similarly, compositions comprising about 2% (w/v) lactose resulted in an initial recovered potency of about 41% (Table 2), compositions comprising about 1% (w/v) sucrose resulted in no recovered potency (Table 2), and compositions comprising about 2% (w/v) lactose and about 1% (w/v) sucrose resulted in an initial recovered potency of about 68% (Table 3). Although there was an increased initial recovered potency in compositions comprising both about 2% (w/v) lactose and about 1% (w/v) sucrose, long-term stability of the Clostridial toxin active ingredient in Clostridial toxin pharmaceutical compositions comprising about 2% lactose and about 1% sucrose were similar to compositions comprising about 2% (w/v) lactose alone (See Tables 3 & 4).

Similarly, the addition of 10 mM sodium citrate (pH 5.5), 10 mM sodium citrate (pH 6.5), and 10 mM potassium phosphate (pH 5.5) had no effect on either initial recovered potency or long-term stability of the Clostridial toxin active ingredient in Clostridial toxin pharmaceutical compositions comprising about 2% lactose and about 1% sucrose when compared to compositions comprising about 2% lactose as the sole sugar excipient. Surprisingly, however, in Clostridial toxin pharmaceutical compositions comprising lactose, 2% (w/v), and sucrose, 1% (w/v), the addition of 10 mM potassium phosphate (pH 6.5) increased initial recovered potency from 0% to about 50%, and this formulation was stable for at least one year at freezing temperatures. Similarly striking, in Clostridial toxin pharmaceutical compositions comprising lactose, 2% (w/v), and sucrose, 1% (w/v), the addition of 10 mM sodium chloride increased initial recovered potency (compare lactose, 2% (w/v), 10 mM sodium chloride at about 39%, sucrose, 2% (w/v), 10 mM sodium chloride at 0%, and lactose, 2% (w/v), sucrose, 1% (w/v), 10 mM sodium chloride at about 61%). More importantly, this formulation resulted in long-term stability of at least one year at both ambient and freezing temperatures.

Clostridial toxin pharmaceutical compositions comprising sucrose and either trehalose or mannitol did not improve initial recovered potency, with most combinations resulting in no recovery whatsoever. Similarly, Clostridial toxin pharmaceutical compositions comprising lactose and mannitol did not improve initial recovered potency (compare 5% (w/v) lactose at about 35% (Table 2), 5% (w/v) mannitol at 0% (Table 2), and 5% (w/v) lactose 5% (w/v) and mannitol at about 23% (Table 3)).

Clostridial toxin pharmaceutical compositions comprising a sugar and a non-protein polymer expanded the range of excipient amounts effective at producing initial recovered potency and long-term stability of the Clostridial toxin active ingredient. For example, various amount of sucrose in combination with various amount of PVP 17 expanded the range of excipient amounts effective at increased recovered potency and long-term stability of the Clostridial toxin active ingredient. When sucrose was used as the sole excipient at ranges from about 5 mg to about 250 mg (about 0.5% (w/v) to about 25% (w/v)), no detectable recovered potency of a Clostridial toxin active ingredient was observed, whereas PVP 17 at about 5 mg to about 20 mg (about 0.5% (w/v) to about 2% (w/v)) resulted in an initial recovered potency. However, Clostridial toxin pharmaceutical compositions comprising about 30 mg to about 250 mg (about 3% (w/v) to about 25% (w/v)) of sucrose in combination with about 30 mg to about 250 mg (about 3% (w/v) to about 25% (w/v)) of PVP 17 resulted in about 39 to about 62% initial recovered potency of the Clostridial toxin active ingredient (each of these excipients at these amounts alone resulted in no detectable recovery). As another example, about 5 mg of sucrose (about 0.5% (w/v)) in combination with from about 50 mg of PVP 17 (about 5% (w/v)) increased recovered potency of the Clostridial toxin active ingredient to about 39% (Table 3) (each of these excipients at these amounts alone resulted in no detectable recovery).

Depending on the amounts added, the addition of various buffers to Clostridial toxin pharmaceutical compositions comprising sucrose and PVP 17 affected the initial recovered potency or long-term stability of the Clostridial toxin active ingredient (Table 3). For example, Clostridial toxin pharmaceutical compositions comprising about 20 mg sucrose and 10 mg PVP 17 resulted in an initial recovered potency of about 77% (Table 2). However, the addition of a sodium citrate buffer to this formulation resulted in an increased recovered potency of about 87% to about 100% (Table 3). Furthermore, the addition of an about pH 5.5 sodium citrate buffer to Clostridial toxin pharmaceutical compositions comprising about 20 mg sucrose and 10 mg PVP 17 resulted in at least one year long-term stability when stored at either ambient or below freezing temperatures (Table 3). Likewise, although not increasing the degree of initial recovered potency observed, Clostridial toxin pharmaceutical compositions comprising about 20 mg sucrose and 10 mg PVP 17 in about pH 5.5 to about pH 6.5 potassium phosphate buffer resulted in significantly increased long term stability of the formulations stored at ambient temperatures (Table 3).

In Clostridial toxin pharmaceutical compositions comprising sucrose and PVP 17, the addition of sodium chloride to the formulation did not appear to have a great effect on initial recovered potency. However, Clostridial toxin pharmaceutical compositions comprising about 20 mg sucrose and 10 mg PVP 17 in sodium chloride resulted in significantly increased long term stability of the formulations stored at ambient temperatures (Table 3).

TABLE 3

Formulations using Botulinum Neurotoxin Complex[a] - Two Excipients with One Being a Sugar

| Excipient 1 | | Excipient 2 | | | | Recovered Potency[b] (%) | | | | |
|---|---|---|---|---|---|---|---|---|---|---|
| | | | | | | | Ambient Temperature[c] | | Below Freezing Temperature[d] | |
| Type | Amount (mg) | Type | Amount (mg) | Ratio | Solution (pH) | Initial | 3 months | 12 months | 3 months | 12 months |
| Sucrose | 50 | Lactose | 50 | 1:1 | Water (pH 4.8) | 27 | | | | |
| Sucrose | 10 | Lactose | 20 | 1:2 | Water (pH 4.8) | 68 | 44 | 44 | 46 | 50 |
| Sucrose | 10 | Lactose | 20 | 1:2 | 10 mM SC (pH 5.5) | 64 | 68 | 58 | 65 | 65 |
| Sucrose | 10 | Lactose | 20 | 1:2 | 10 mM SC (pH 6.5) | 41 | 0 | 0 | 41 | 0 |
| Sucrose | 10 | Lactose | 20 | 1:2 | 10 mM PP (pH 5.5) | 43 | 55 | 49 | 55 | 68 |
| Sucrose | 10 | Lactose | 20 | 1:2 | 10 mM PP (pH 6.5) | 50 | 0 | 0 | 51 | 38 |
| Sucrose | 10 | Lactose | 20 | 1:2 | 10 mM NaCl (pH 4.8) | 61 | 58 | 45 | 66 | 58 |
| Sucrose | 50 | Trehalose | 50 | 1:1 | Water (pH 4.3) | 0 | 0 | 0 | 0 | 0 |
| Sucrose | 50 | Trehalose | 5 | 10:1 | Water (pH 4.3) | 0 | 0 | 0 | 0 | 0 |
| Sucrose | 5 | Trehalose | 50 | 1:10 | Water (pH 4.3) | 0 | 0 | 0 | 0 | 0 |
| Sucrose | 50 | Mannitol | 5 | 10:1 | Water (pH 4.3) | 0 | 0 | 0 | 0 | 0 |
| Sucrose | 50 | Mannitol | 50 | 1:1 | Water (pH 4.3) | 27 | — | — | — | — |
| Sucrose | 5 | Mannitol | 50 | 1:10 | Water (pH 4.3) | 0 | 0 | 0 | 0 | 0 |
| Sucrose | 250 | PVP 17 | 10 | 25:1 | Water (pH 4.3) | 58 | — | — | — | — |
| Sucrose | 5 | PVP 17 | 0.5 | 10:1 | Water (pH 4.3) | 0 | 0 | 0 | 0 | 0 |
| Sucrose | 20 | PVP 17 | 10 | 2:1 | Water (pH 4.3) | 77 | 49 | 0 | 76 | 101 |
| Sucrose | 250 | PVP 17 | 250 | 1:1 | Water (pH 4.3) | 39 | — | — | — | — |
| Sucrose | 30 | PVP 17 | 30 | 1:1 | Water (pH 4.1) | 62 | — | — | — | — |
| Sucrose | 15 | PVP 17 | 15 | 1:1 | Water (pH 4.1) | 77 | 0 | 0 | 68 | 80 |
| Sucrose | 5 | PVP 17 | 5 | 1:1 | Water (pH 4.3) | 49 | — | — | — | — |
| Sucrose | 0.5 | PVP 17 | 0.5 | 1:1 | Water (pH 4.3) | 0 | 0 | 0 | 0 | 0 |
| Sucrose | 5 | PVP 17 | 10 | 1:2 | Water (pH 4.3) | 58 | — | — | — | — |
| Sucrose | 5 | PVP 17 | 20 | 1:4 | Water (pH 4.3) | 47 | — | — | — | — |
| Sucrose | 5 | PVP 17 | 50 | 1:10 | Water (pH 4.3) | 39 | — | — | — | — |
| Sucrose | 0.5 | PVP 17 | 5 | 1:10 | Water (pH 4.3) | 58 | — | — | — | — |
| Sucrose | 5 | PVP 17 | 100 | 1:20 | Water (pH 4.3) | 0 | 0 | 0 | 0 | 0 |
| Sucrose | 0.5 | PVP 17 | 10 | 1:20 | Water (pH 4.3) | 46 | — | — | — | — |
| Sucrose | 0.5 | PVP 17 | 20 | 1:40 | Water (pH 4.3) | 49 | — | — | — | — |
| Sucrose | 20 | PVP 17 | 10 | 2:1 | 10 mM SC (pH 5.5) | 100 | 52 | 38 | 87 | 101 |
| Sucrose | 20 | PVP 17 | 10 | 2:1 | 10 mM SC (pH 6.5) | 87 | 0 | 0 | 88 | 85 |
| Sucrose | 20 | PVP 17 | 10 | 2:1 | 10 mM PP (pH 5.5) | 65 | 42 | 47 | 83 | 87 |
| Sucrose | 20 | PVP 17 | 10 | 2:1 | 10 mM PP (pH 6.5) | 63 | 61 | 51 | 75 | 99 |
| Sucrose | 20 | PVP 17 | 10 | 2:1 | 10 mM NaCl (pH 4.4) | 83 | 112 | 43 | 77 | 93 |
| Sucrose | 30 | PVP 17 | 30 | 1:1 | 10 mM NaCl (pH 4.1) | 66 | 0 | 0 | 66 | 66 |
| Sucrose | 15 | PVP 17 | 15 | 1:1 | 10 mM NaCl (pH 4.1) | 59 | 0 | 0 | 59 | 59 |
| Sucrose | 50 | PEG 3350 | 5 | 10:1 | Water | 41 | — | — | — | — |
| Sucrose | 50 | PEG 3350 | 50 | 1:1 | Water | 44 | — | — | — | — |
| Sucrose | 5 | PEG 3350 | 50 | 1:10 | Water | 35 | — | — | — | — |
| Sucrose | 10 | Poloxamer 188 | 0.25 | 40:1 | Water (pH 5.9) | 62 | 0 | 0 | 78 | 78 |
| Sucrose | 5 | Poloxamer 188 | 0.125 | 40:1 | Water (pH 5.7) | 70 | 0 | 0 | 70 | 78 |
| Sucrose | 60 | Poloxamer 188 | 3 | 20:1 | Water (pH 6.1) | 75 | 0 | 0 | 84 | 106 |
| Sucrose | 30 | Poloxamer 188 | 1.5 | 20:1 | Water (pH 6.1) | 104 | 0 | 0 | 92 | 79 |
| Sucrose | 10 | Poloxamer 188 | 0.5 | 20:1 | Water (pH 6.2) | 66 | 0 | 0 | 88 | 79 |

TABLE 3-continued

Formulations using Botulinum Neurotoxin Complex[a] - Two Excipients with One Being a Sugar

| Excipient 1 | | Excipient 2 | | | | Recovered Potency[b] (%) | | | | |
| --- | --- | --- | --- | --- | --- | --- | --- | --- | --- | --- |
| | | | | | | | Ambient Temperatrue[c] | | Below Freezing Temperature[d] | |
| Type | Amount (mg) | Type | Amount (mg) | Ratio | Solution (pH) | Initial | 3 months | 12 months | 3 months | 12 months |
| Sucrose | 5 | Poloxamer 188 | 0.25 | 20:1 | Water (pH 5.9) | 64 | 0 | 0 | 78 | 78 |
| Sucrose | 55 | Poloxamer 188 | 5.5 | 10:1 | Water (pH 6.7) | 99 | 0 | 0 | 115 | 115 |
| Sucrose | 50 | Poloxamer 188 | 5 | 10:1 | Water | 43 | — | — | — | — |
| Sucrose | 27 | Poloxamer 188 | 2.7 | 10:1 | Water (pH 6.2) | 92 | 0 | 0 | 80 | 80 |
| Sucrose | 48 | Poloxamer 188 | 12 | 4:1 | Water (pH 6.4) | 110 | 0 | 0 | 85 | 113 |
| Sucrose | 24 | Poloxamer 188 | 6 | 4:1 | Water (pH 6.4) | 102 | 0 | 0 | 88 | 84 |
| Sucrose | 10 | Poloxamer 188 | 2.5 | 4:1 | Water (pH 6.4) | 84 | 0 | 0 | 104 | 87 |
| Sucrose | 5 | Poloxamer 188 | 1.25 | 4:1 | Water (pH 6.4) | 72 | 0 | 0 | 92 | 82 |
| Sucrose | 40 | Poloxamer 188 | 20 | 2:1 | Water (pH 6.9) | 113 | 78 | 74 | 102 | 111 |
| Sucrose | 20 | Poloxamer 188 | 10 | 2:1 | Water (pH 6.5) | 101 | 87 | 0 | 117 | 115 |
| Sucrose | 10 | Poloxamer 188 | 5 | 2:1 | Water (pH 6.9) | 94 | 0 | 0 | 92 | 106 |
| Sucrose | 5 | Poloxamer 188 | 2.5 | 2:1 | Water (pH 6.6) | 105 | 61 | 0 | 108 | 102 |
| Sucrose | 2.5 | Poloxamer 188 | 1.25 | 2:1 | Water (pH 6.4) | 87 | — | — | 85 | 86 |
| Sucrose | 1.25 | Poloxamer 188 | 0.625 | 2:1 | Water (pH 6.2) | 71 | — | — | 81 | 90 |
| Sucrose | 50 | Poloxamer 188 | 50 | 1:1 | Water | 59 | — | — | — | — |
| Sucrose | 20 | Poloxamer 188 | 40 | 1:2 | Water (pH 6.9) | 115 | 117 | 101 | 117 | 115 |
| Sucrose | 5 | Poloxamer 188 | 50 | 1:10 | Water | 55 | — | — | — | — |
| Sucrose | 60 | Poloxamer 188 | 6 | 10:1 | 10 mM SC (pH 5.5) | 111 | 97 | | 101 | 115 |
| Sucrose | 40 | Poloxamer 188 | 20 | 2:1 | 10 mM SC (pH 5.5) | 113 | 112 | 89 | 115 | 101 |
| Sucrose | 20 | Poloxamer 188 | 10 | 2:1 | 10 mM SC (pH 5.5) | 77 | 81 | 101 | 81 | 115 |
| Sucrose | 5 | Poloxamer 188 | 2.5 | 2:1 | 10 mM SC (pH 5.5) | 92 | — | — | 90 | 102 |
| Sucrose | 2.5 | Poloxamer 188 | 1.25 | 2:1 | 10 mM SC (pH 5.5) | 80 | — | — | 102 | 80 |
| Sucrose | 1.25 | Poloxamer 188 | 0.625 | 2:1 | 10 mM SC (pH 5.5) | 106 | — | — | 102 | 77 |
| Sucrose | 0.625 | Poloxamer 188 | 0.3125 | 2:1 | 10 mM SC (pH 5.5) | 80 | — | — | 92 | 92 |
| Sucrose | 20 | Poloxamer 188 | 10 | 2:1 | 10 mM SC (pH 6.5) | 90 | 91 | 67 | 115 | 97 |
| Sucrose | 20 | Poloxamer 188 | 10 | 2:1 | 10 mM PP (pH 5.5) | 112 | 113 | 0 | 113 | 115 |
| Sucrose | 20 | Poloxamer 188 | 10 | 2:1 | 10 mM PP (pH 6.5) | 93 | 90 | 63 | 119 | 84 |
| Sucrose | 20 | Poloxamer 188 | 40 | 1:2 | 10 mM SC (pH5.5) | 107 | 115 | 101 | 115 | 117 |
| Sucrose | 30 | Poloxamer 188 | 1.5 | 20:1 | 10 mM NaCl (pH 6.0) | 104 | 0 | 0 | 104 | 102 |
| Sucrose | 55 | Poloxamer 188 | 5.5 | 10:1 | 10 mM NaCl (pH 6.1) | 104 | 0 | 0 | 84 | 84 |
| Sucrose | 27 | Poloxamer 188 | 2.7 | 10:1 | 10 mM NaCl (pH 6.1) | 102 | 0 | 0 | 96 | 81 |
| Sucrose | 48 | Poloxamer 188 | 12 | 4:1 | 10 mM NaCl (pH 6.2) | 96 | 0 | 0 | 97 | 92 |
| Sucrose | 24 | Poloxamer 188 | 6 | 4:1 | 10 mM NaCl (pH 6.2) | 100 | 0 | 0 | 66 | 0 |
| Sucrose | 40 | Poloxamer 188 | 20 | 2:1 | 10 mM NaCl (pH 6.4) | 84 | 80 | 80 | 102 | 102 |
| Sucrose | 20 | Poloxamer 188 | 10 | 2:1 | 10 mM NaCl (pH 6.2) | 117 | 50 | 89 | 115 | 117 |
| Sucrose | 5 | Poloxamer 188 | 2.5 | 2:1 | 10 mM NaCl (pH 6.1) | 87 | — | — | 106 | 92 |
| Sucrose | 2.5 | Poloxamer 188 | 1.25 | 2:1 | 10 mM NaCl (pH 6.0) | 92 | — | — | 82 | 102 |
| Sucrose | 1.25 | Poloxamer 188 | 0.625 | 2:1 | 10 mM NaCl (pH 5.8) | 85 | — | — | 92 | 105 |
| Sucrose | 0.625 | Poloxamer 188 | 0.3125 | 2:1 | 10 mM NaCl (pH 5.8) | 92 | — | — | 78 | 92 |
| Sucrose | 10 | Polysorbate 80 | 0.5 | 20:1 | Water (pH 5.8) | 98 | — | — | 82 | 82 |
| Sucrose | 5 | Polysorbate 80 | 0.25 | 20:1 | Water (pH 5.8) | 78 | — | — | 92 | 92 |
| Sucrose | 10 | Polysorbate 80 | 2.5 | 4:1 | Water (pH 6.0) | 96 | — | — | 104 | 104 |
| Sucrose | 5 | Polysorbate 80 | 1.25 | 4:1 | Water (pH 6.0) | 102 | — | — | 90 | 90 |
| Sucrose | 50 | Glycine | 50 | 1:1 | Water | 0 | 0 | 0 | 0 | 0 |
| Sucrose | 50 | Glycine | 5 | 10:1 | Water | 0 | 0 | 0 | 0 | 0 |
| Sucrose | 5 | Glycine | 50 | 1:10 | Water | 0 | 0 | 0 | 0 | 0 |
| Lactose | 50 | Mannitol | 50 | 1:1 | Water | 23 | — | — | — | — |
| Lactose | 5 | PVP 17 | 0.5 | 10:1 | Water | 52 | — | — | — | — |
| Lactose | 5 | PVP 17 | 5 | 1:1 | Water | 57 | — | — | — | — |
| Lactose | 0.5 | PVP 17 | 0.5 | 1:1 | Water | 0 | 0 | 0 | 0 | 0 |
| Lactose | 5 | PVP 17 | 10 | 1:2 | Water | 65 | — | — | — | — |
| Lactose | 5 | PVP 17 | 20 | 1:4 | Water | 49 | — | — | — | — |
| Lactose | 5 | PVP 17 | 50 | 1:10 | Water | 52 | — | — | — | — |
| Lactose | 0.5 | PVP 17 | 5 | 1:10 | Water | 65 | — | — | — | — |
| Lactose | 5 | PVP 17 | 100 | 1:20 | Water | 0 | — | — | — | — |
| Lactose | 0.5 | PVP 17 | 10 | 1:20 | Water | 47 | — | — | — | — |
| Lactose | 0.5 | PVP 17 | 20 | 1:40 | Water | 65 | — | — | — | — |
| Lactose | 0.5 | PVP 17 | 50 | 1:100 | Water | 0 | — | — | — | — |
| Lactose | 55 | PEG 3550 | 5.5 | 10:1 | Water (pH 4.9) | 96 | 61 | 62 | 112 | 98 |
| Lactose | 40 | PEG 3550 | 20 | 2:1 | Water (pH 5.6) | 96 | 58 | 55 | 110 | 117 |
| Lactose | 50 | PEG 3350 | 50 | 1:1 | Water | 53 | — | — | — | — |
| Lactose | 55 | PEG 3550 | 5.5 | 10:1 | 10 mM SC (pH 5.5) | 96 | 62 | 62 | 82 | 102 |
| Lactose | 40 | PEG 3550 | 20 | 2:1 | 10 mM SC (pH 5.5) | 79 | 66 | 70 | 92 | 104 |
| Lactose | 55 | Poloxamer 188 | 5.5 | 10:1 | Water (pH 4.7) | 108 | 80 | 55 | 106 | 92 |
| Lactose | 40 | Poloxamer 188 | 20 | 2:1 | Water (pH 5.9) | 88 | 60 | 46 | 107 | 104 |
| Lactose | 20 | Poloxamer 188 | 10 | 2:1 | Water (pH 5.6) | 63 | 69 | 0 | 95 | 113 |
| Lactose | 5 | Poloxamer 188 | 2.5 | 2:1 | Water (pH 5.8) | 107 | — | — | 110 | 106 |
| Lactose | 2.5 | Poloxamer 188 | 1.25 | 2:1 | Water (pH 5.8) | 87 | — | — | 92 | 82 |
| Lactose | 1.25 | Poloxamer 188 | 0.625 | 2:1 | Water (pH 5.7) | 92 | — | — | 96 | 104 |
| Lactose | 0.625 | Poloxamer 188 | 0.3125 | 2:1 | Water (pH 5.6) | 73 | — | — | 66 | 100 |

TABLE 3-continued

Formulations using Botulinum Neurotoxin Complex[a] - Two Excipients with One Being a Sugar

| Excipient 1 | | Excipient 2 | | | | Recovered Potency[b] (%) | | | | |
| | | | | | | Initial | Ambient Temperatrue[c] | | Below Frerezing Temperature[d] | |
| Type | Amount (mg) | Type | Amount (mg) | Ratio | Solution (pH) | | 3 months | 12 months | 3 months | 12 months |
|---|---|---|---|---|---|---|---|---|---|---|
| Lactose | 55 | Poloxamer 188 | 5.5 | 10:1 | 10 mM SC (pH 5.5) | 100 | 78 | 58 | 96 | 102 |
| Lactose | 40 | Poloxamer 188 | 20 | 2:1 | 10 mM SC (pH 5.5) | 93 | 66 | 59 | 107 | 122 |
| Lactose | 20 | Poloxamer 188 | 10 | 2:1 | 10 mM SC (pH 5.5) | 101 | 73 | 69 | 99 | 117 |
| Lactose | 5 | Poloxamer 188 | 2.5 | 2:1 | 10 mM SC (pH 5.5) | 107 | — | — | 92 | 112 |
| Lactose | 2.5 | Poloxamer 188 | 1.25 | 2:1 | 10 mM SC (pH 5.5) | 86 | — | — | 102 | 101 |
| Lactose | 1.25 | Poloxamer 188 | 0.625 | 2:1 | 10 mM SC (pH 5.5) | 106 | — | — | 90 | 107 |
| Lactose | 0.625 | Poloxamer 188 | 0.3125 | 2:1 | 10 mM SC (pH 5.5) | 74 | — | — | 61 | 81 |
| Lactose | 20 | Poloxamer 188 | 10 | 2:1 | 10 mM SC (pH 6.5) | 81 | 56 | 56 | 113 | 117 |
| Lactose | 20 | Poloxamer 188 | 10 | 2:1 | 10 mM PP (pH 5.5) | 115 | 88 | 85 | 107 | 114 |
| Lactose | 20 | Poloxamer 188 | 10 | 2:1 | 10 mM PP (pH 6.5) | 91 | 65 | 65 | 103 | 93 |
| Lactose | 20 | Poloxamer 188 | 10 | 2:1 | 10 mM NaCl (pH 5.5) | 115 | 87 | 101 | 115 | 115 |
| Lactose | 5 | Poloxamer 188 | 2.5 | 2:1 | 10 mM NaCl (pH 5.5) | 107 | — | — | 92 | 112 |
| Lactose | 2.5 | Poloxamer 188 | 1.25 | 2:1 | 10 mM NaCl (pH 5.5) | 86 | — | — | 102 | 101 |
| Lactose | 1.25 | Poloxamer 188 | 0.625 | 2:1 | 10 mM NaCl (pH 5.5) | 106 | — | — | 90 | 107 |
| Lactose | 0.625 | Poloxamer 188 | 0.3125 | 2:1 | 10 mM NaCl (pH 5.5) | 74 | — | — | 61 | 81 |
| Trehalose | 50 | Mannitol | 50 | 10:1 | Water | 0 | 0 | 0 | 0 | 0 |
| Trehalose | 50 | Mannitol | 5 | 1:1 | Water | 0 | 0 | 0 | 0 | 0 |
| Trehalose | 5 | Mannitol | 50 | 1:10 | Water | 0 | 0 | 0 | 0 | 0 |
| Trehalose | 50 | PEG 3350 | 5 | 10:1 | Water | 41 | — | — | — | — |
| Trehalose | 50 | PEG 3350 | 50 | 1:1 | Water | 0 | 0 | 0 | 0 | 0 |
| Trehalose | 5 | PEG 3350 | 50 | 1:10 | Water | 36 | — | — | — | — |
| Trehalose | 50 | Poloxamer 188 | 5 | 10:1 | Water | 50 | — | — | — | — |
| Trehalose | 50 | Poloxamer 188 | 50 | 1:1 | Water | 53 | — | — | — | — |
| Trehalose | 5 | Poloxamer 188 | 50 | 1:10 | Water | 75 | — | — | — | — |
| Trehalose | 50 | Glycine | 5 | 10:1 | Water | 0 | 0 | 0 | 0 | 0 |
| Trehalose | 50 | Glycine | 50 | 1:1 | Water | 0 | 0 | 0 | 0 | 0 |
| Trehalose | 5 | Glycine | 50 | 1:10 | Water | 0 | 0 | 0 | 0 | 0 |

[a]Amount of botulinum neurotoxin serotype A complex added per formulation was 150 units. Total volume of formulation was 1.0 mL.
[b]Recovery is expressed as a percentage and is calculated by dividing the potency of the active ingredient determined after reconstitution divided by the potency of the active ingredient determined before addition to the formulation. 3 months refers to the length of time a formulation was minimally stored at the indicated temperature. 12 months refers to the length of time a formulation was minimally stored at the indicated temperature.
[c]Ambient temperature is between about 18° C. to about 22° C.
[d]Below freezing temperature is between about −5° C. to about −20° C.

As another example, although no detectable recovered potency was observed when about 5 mg to about 50 mg of sucrose (about 0.5 (w/v) to about 5% (w/v)) was used as the sole excipient, or when about 50 mg of PEG 3350 (about 5% (w/v)) was used as the sole excipient, in combination about 35% to about 44% increased recovered potency of the Clostridial toxin active ingredient was exhibited (Table 3).

Clostridial toxin pharmaceutical compositions comprising lactose and a non-protein polymer also expanded the range of excipient amounts effective at producing initial recovered potency and long-term stability of the Clostridial toxin active ingredient. For example, when used as the sole excipient, lactose was effective at increasing recovered potency at about 10 mg to about 50 mg (about 1% (w/v) to about 5% (w/v)) (Table 2), whereas PVP 17 was effective at increasing recovered potency at about 5 mg to about 20 mg (about 0.5% (w/v) to about 2% (w/v)) (Table 2). However, about 5 mg of lactose (about 0.5% (w/v)) in combination with from about 0.5 mg of PVP 17 (about 0.05% (w/v)) increased initial recovered potency of the Clostridial toxin active ingredient to about 52% (Table 3) (each of these excipients at these amounts alone resulted in no detectable recovery, see Table 2). As another example, about 5 mg of lactose (about 0.5% (w/v)) in combination with from about 50 mg of PVP 17 (about 5% (w/v)) increased initial recovered potency of the Clostridial toxin active ingredient to about 52% (Table 3) (each of these excipients at these concentrations alone resulted in no detectable recovery, see Table 2).

Furthermore, the addition of lactose, at amounts this sugar alone is ineffective to produce initial recovered potency of the Clostridial toxin active ingredient, appeared to enhance initial recovered potency in Clostridial toxin pharmaceutical compositions comprising an amount of PVP 17 sufficient to produce an initial recovered potency as the sole excipient. For example, about 5 mg of lactose (0.5% (w/v)) in combination with about 5 mg to about 20 mg of PVP 17 (about 0.5% (w/v) to about 2% (w/v)) increased initial recovered potency of the Clostridial toxin active ingredient to about 57%, about 65%, and about 49%, respectively (Table 3). This recovered potency is significantly higher that the recovery observed when PVP 17 is used as the sole excipient (See Table 2, 5 mg of PVP 17, 0.5% (w/v) alone at about 48%; 10 mg of PVP 17, 1% (w/v) alone at about 52%; 20 mg of PVP 17, 2% (w/v) alone at about 43%). Similarly, about 0.5 mg of lactose (0.05% (w/v)) in combination with about 5 mg to about 20 mg of PVP 17 (about 0.5% (w/v) to about 2% (w/v)) increased initial recovered potency of the Clostridial toxin active ingredient to about 65%, about 47%, and about 65%, respectively (Table 3). In general, this recovered potency is significantly higher that the recovery observed when PVP 17 is used as the sole excipient (See Table 2, 5 mg of PVP 17, 0.5% (w/v) alone at about 48%; 10 mg of PVP 17, 1% (w/v) alone at about 52%; 20 mg of PVP 17, 2% (w/v) alone at about 43%).

Similar results were seen when lactose was combined with PEG 3350. Clostridial toxin pharmaceutical compositions comprising about 50 mg lactose (about 5% (w/v))

resulted in an initial recovered potency of 35% (Table 2), whereas, Clostridial toxin compositions comprising about 50 mg PEG 3350 (about 5% (w/v)) resulted in no initial recovered potency of the Clostridial toxin active ingredient (Table 2). However, Clostridial toxin compositions comprising about 50 mg lactose (about 5% (w/v)) and about 50 mg PEG 3350 (about 5% (w/v)) resulted in an initial recovered potency of 53% (Table 3). Enhancement of initial recovered potency was also observed in Clostridial toxin compositions comprising about lactose and PEG 3350 in various buffered solutions (see Table 3).

Clostridial toxin pharmaceutical compositions comprising a sugar and a surfactant resulted in an effective increased recovered potency and long-term stability of the Clostridial toxin active ingredient over a wide range of excipient amounts. For example, both sucrose alone and Poloxamer 188 alone resulted in no detectable recovered potency of a Clostridial toxin active ingredient (Table 2). Surprisingly Clostridial toxin pharmaceutical compositions comprising from about 1.25 mg to about 60 mg of sucrose (about 0.125% (w/v) to about 6% (w/v)) in combination with about 0.25 mg to about 50 mg of Poloxamer 188 (about 0.025% (w/v) to about 5% (w/v)), all resulted in increased recovered potency of the Clostridial toxin active ingredient of about 43% to about 115% (Table 3). In addition, all such combinations resulted in long-term stability of at least one year of the Clostridial toxin active ingredient when stored at least at below freezing temperatures (Table 3).

Interestingly, in Clostridial toxin pharmaceutical compositions comprising sucrose and Poloxamer 188, the addition of various buffers to the formulation did not appear to have a great effect on initial recovered potency or long-term stability of the Clostridial toxin active ingredient when stored at below freezing temperatures (Table 3). Surprisingly, however, the addition of various buffers to Clostridial toxin pharmaceutical compositions comprising sucrose and Poloxamer 188 dramatically improved long-term stability of the Clostridial toxin active ingredient when stored at ambient temperatures (Table 3). The addition of sodium chloride to Clostridial toxin pharmaceutical compositions comprising sucrose and Poloxamer 188 did not appear to have a great affect on initial recovered potency or long-term stability of the Clostridial toxin active ingredient (Table 3).

Similar results where seen when sucrose was combined with polysorbate 80. Clostridial toxin compositions comprising about sucrose as the sole excipient resulted in no detectable recovered potency of a Clostridial toxin active ingredient (Table 2). However, Clostridial toxin compositions comprising about 10 mg to about 20 mg sucrose (about 1% (w/v) to about 2% (w/v)) and about 0.25 mg to about 2.5 mg polysorbate 80 (about 0.025% (w/v) to about 0.25% (w/v)) resulted in an initial recovered potency of about 78% to about 102% (Table 3). The enhancement of long term stability was also observed in Clostridial toxin compositions comprising about sucrose and polysorbate 80 (see Table 3).

As another example, both sucrose alone and Poloxamer 188 alone resulted in no detectable recovered potency of a Clostridial toxin active ingredient (Table 2). Surprisingly Clostridial toxin pharmaceutical compositions comprising from about 1.25 mg to about 60 mg of sucrose (about 0.125% (w/v) to about 6% (w/v)) in combination with about 0.25 mg to about 50 mg of Poloxamer 188 (about 0.025% (w/v) to about 5% (w/v)), all resulted in increased recovered potency of the Clostridial toxin active ingredient of about 43% to about 115% (Table 3). In addition, all such combinations resulted in long-term stability of at least one year of the Clostridial toxin active ingredient when stored at least at below freezing temperatures (Table 3).

Clostridial toxin pharmaceutical compositions comprising lactose and Poloxamer 188 also expanded the range of excipient amounts effective at producing initial recovered potency and long-term stability of the Clostridial toxin active ingredient. For example, when used as the sole excipient, lactose was effective at recovering the Clostridial toxin active ingredient at about 10 mg to about 50 mg (about 1% (w/v) to about 5% (w/v)) (Table 2), whereas Poloxamer 188 alone resulted in no detectable recovered potency of a Clostridial toxin active ingredient (Table 2). However, about 0.625 to about 5 mg of lactose (about 0.0625% (w/v) to about 0.5% (w/v)) in combination with about 0.3125 mg to about 2.5 mg Poloxamer 188 (about 0.03125% (w/v) to about 0.25% (w/v)) increased initial recovered potency of the Clostridial toxin active ingredient to about 73% to about 107 (Table 3) (each of these excipients at these amounts alone resulted in no detectable recovery, see Table 2). In addition, all such combinations resulted in long-term stability of at least one year of the Clostridial toxin active ingredient when stored at least at below freezing temperatures (Table 3).

Furthermore, the addition of Poloxamer 188, at amounts this surfactant alone is ineffective to produce recovery of the Clostridial toxin active ingredient, appeared to enhance initial recovered potency in Clostridial toxin pharmaceutical compositions comprising an amount of lactose sufficient to produce an initial recovered potency as the sole excipient. For example, about 20 mg to about 55 mg of lactose (about 2% (w/v) to about 5.5% (w/v)) in combination with about 5.5 mg to about 20 mg of Poloxamer 188 (about 0.55% (w/v) to about 2% (w/v)) increased initial recovered potency of the Clostridial toxin active ingredient to about 63% to about 108% (Table 3). This recovered potency is significantly higher that the recovery observed when lactose was used as the sole excipient (See Table 2, 10 mg of lactose, 1% (w/v) alone at about 15%; 20 mg of lactose, 2% (w/v) alone at about 41%; 50 mg of lactose, 5% (w/v) alone at about 35%).

Depending on the amounts added, the addition of various buffers to Clostridial toxin pharmaceutical compositions comprising lactose and Poloxamer 188 affected the initial recovered potency or long-term stability of the Clostridial toxin active ingredient (Table 3). For example, Clostridial toxin pharmaceutical compositions comprising about 20 mg lactose and 10 mg Poloxamer 188 resulted in an initial recovered potency of about 63% (Table 2). However, the addition of an about pH 5.5 to an about pH 6.5 buffered solution to this formulation resulted in an increased initial recovered potency of about 81% to about 115% (Table 3). Likewise, the addition of a buffer to these formulations resulted in enhanced long-term stability of at least one year when stored at either ambient or below freezing temperatures. Similarly, the addition of sodium chloride to Clostridial toxin pharmaceutical compositions comprising lactose and Poloxamer 188, although not having a dramatic affect on initial recovered potency, greatly increased long-term stability of the Clostridial toxin active ingredient, especially at when stored at ambient temperatures (Table 3).

Clostridial toxin pharmaceutical compositions comprising two non-protein polymers resulted in enhanced recovered potency and long-term stability of the Clostridial toxin active ingredient. For example, the addition of Dextran 3K, at amounts this non-protein polymer alone is ineffective to produce initial recovered potency of the Clostridial toxin active ingredient, appeared to enhance initial recovered potency in Clostridial toxin pharmaceutical compositions comprising an amount of PEG 3350 sufficient to produce an initial recovered potency as the sole excipient. Thus, compositions comprising both Dextran 3K and PEG 3350 exhibited enhanced initial recovered potency in water (compare 0% initial recovered potency of PEG 3350 alone (Table 2) with 47% initial recovered potency Dextran 3K and PEG 3350 together (Table 4)); in sodium citrate buffers (compare 76% initial recovered potency of PEG 3350 alone in sodium citrate buffer (pH 5.5) (Table 2) with 92% initial recovered potency Dextran 3K and PEG 3350 together in sodium citrate buffer (pH 5.5) (Table 4); and 57% initial recovered potency of PEG 3350 alone in sodium citrate buffer (pH 6.5) (Table 2) with 82% initial recovered potency Dextran 3K and PEG 3350 together in sodium citrate buffer (pH 6.5) (Table 4)); potassium phosphate buffers (compare 80% initial recovered potency of PEG 3350 alone in potassium phosphate buffer (pH 5.5) (Table 2) with 101% initial recovered potency Dextran 3K and PEG 3350 together in potassium phosphate buffer (pH 5.5) (Table 4); and 0% initial recovered potency of PEG 3350 alone in potassium phosphate buffer (pH 6.5) (Table 2) with 102% initial recovered potency Dextran 3K and PEG 3350 together in potassium phosphate buffer (pH 5.5) (Table 4)); and histidine buffers (compare 72% initial recovered potency of PEG 3350 alone in potassium phosphate buffer (pH 5.5) (Table 2) with 82% initial recovered potency Dextran 3K and PEG 3350 together in histidine buffer (pH 5.5) (Table 4)).

Clostridial toxin pharmaceutical compositions comprising PVP 17 and PEG 3350 expanded the range of excipient amounts effective at producing initial recovered potency and long-term stability of the Clostridial toxin active ingredient. For example, when PVP 17 was used as the sole excipient at ranges from about 30 mg to about 250 mg (about 3% (w/v) to about 25% (w/v)), no detectable recovered potency of a Clostridial toxin active ingredient was observed, whereas PEG 3350 only resulted in initial recovered potency at amounts above about 60 mg (about 6% (w/v)) (Table 2). However, Clostridial toxin pharmaceutical compositions comprising about 30 mg to about 40 mg PVP 17 (about 3% (w/v) to about 4% (w/v)) in combination with about 20 mg to about 30 mg of PEG 3350 (about 2% (w/v) to about 3% (w/v)) resulted in initial recovered potency of about 80% (Table 4) (each of these excipients alone resulted in no detectable initial recovered potency). Likewise, when PEG 3350 was used as the sole excipient at ranges above about 60 mg (about 6% (w/v)), no detectable recovered potency of a Clostridial toxin active ingredient was observed, whereas PVP 17 at about 5 mg to about 20 mg (about 0.5% (w/v) to about 2% (w/v)) resulted in an initial recovered potency (Table 2). However, Clostridial toxin pharmaceutical compositions comprising about 40 mg to about 55 mg (about 4% (w/v) to about 5.5% (w/v)) of PEG 3350 in combination with about 20 mg (about 2% (w/v)) of PVP 17 resulted in about 68% initial recovered potency of the Clostridial toxin active ingredient (20 mg (about 2% (w/v)) of PVP 17 alone resulted in a 43% initial recovered potency) (Table 4). This enhanced initial recovery was also observed when various buffered solutions were added to the formulations (Table 4).

Clostridial toxin pharmaceutical compositions comprising a non-protein polymer and a surfactant resulted in an effective increased recovered potency and long-term stability of the Clostridial toxin active ingredient. For example, both Dextran 3K and Poloxamer 188 alone resulted in no detectable recovered potency of a Clostridial toxin active ingredient (Table 2). Surprisingly Clostridial toxin pharmaceutical compositions comprising both Dextran 3K and Poloxamer 188 resulted in an initial recovered potency of the Clostridial toxin active ingredient of about 78% to about 98% (Table 4). Furthermore, this synergistic effect was also observed in Clostridial toxin pharmaceutical compositions comprising Dextran 3K and Poloxamer 188 in buffered solutions (Table 4). Both Dextran 3K and Poloxamer 188 alone resulted in no detectable recovered potency of a Clostridial toxin active ingredient in formulations comprising sodium citrate buffers or potassium phosphate buffer (pH 6.5) (Table 2). However, Clostridial toxin pharmaceutical compositions comprising Dextran 3K and Poloxamer 188 resulted in about 82% to about 100% initial recovered potency with the addition of sodium citrate buffer (pH 5.5); about 85% to about 99% initial recovered potency with the addition of sodium citrate buffer (pH 6.5); about 82% to about 103% initial recovered potency with the addition of potassium phosphate buffer (pH 6.5); about 103% to about 125% initial recovered potency with the addition of histidine buffer (pH 5.5); and about 115% to about 134% initial recovered potency with the addition of histidine buffer (pH 6.5). In addition, such buffered Clostridial toxin pharmaceutical compositions resulted in enhanced long-term stability for at least one year. Similarly, enhanced recover was seen in Clostridial toxin pharmaceutical compositions comprising Dextran 3K and Poloxamer 188 in potassium phosphate buffer (pH 5.5) (compare 66% initial recovered potency for Dextran 3K alone (Table 2); 39% initial recovered potency for Poloxamer 188 alone (Table 2); and about 90% to about 120% initial recovered potency for Dextran 3K and Poloxamer 188 together (Table 4). Clostridial toxin pharmaceutical compositions comprising Dextran 3K and Poloxamer 188 in potassium phosphate buffer (pH 5.5) also demonstrated enhanced long-term stability when stored at either ambient or below freezing temperatures.

Similar degrees of improved initial recovery and long-term stability was observed in Clostridial toxin pharmaceutical compositions comprising Dextran 40K and Poloxamer 188. For example, both Dextran 40K and Poloxamer 188 alone resulted in no detectable recovered potency of a Clostridial toxin active ingredient (Table 2). Surprisingly Clostridial toxin pharmaceutical compositions comprising both Dextran 40K and Poloxamer 188 resulted in an initial recovered potency of the Clostridial toxin active ingredient of about 85% to about 102% (Table 4). This synergistic effect was also observed in Clostridial toxin pharmaceutical compositions comprising Dextran 40K and Poloxamer 188 in buffered solutions. Both Dextran 40K and Poloxamer 188 alone resulted in no detectable recovered potency of a Clostridial toxin active ingredient in formulations comprising potassium phosphate buffer (pH 6.5) (Table 2). However, Clostridial toxin pharmaceutical compositions comprising Dextran 40K and Poloxamer 188 resulted in about 102% to about 115% initial recovered potency with the addition of potassium phosphate buffer (pH 6.5) (Table 4). Furthermore, Clostridial toxin pharmaceutical compositions comprising Dextran 40K and Poloxamer 188 in various other buffered solutions resulted in enhanced recovered potency and long-term stability of the Clostridial toxin active ingredient. Thus, compositions comprising both Dextran 40K and Poloxamer 188 exhibited enhanced initial recovered potency in sodium citrate buffers (compare 81% initial recovered potency of Poloxamer 188 alone in sodium citrate buffer (pH 5.5) (Table 2) with 128% initial recovered potency Dextran 40K and Poloxamer 188 together in sodium citrate buffer (pH 5.5) (Table 4); and 56% initial recovered potency of Poloxamer 188 alone in sodium citrate buffer (pH 5.5) (Table 2) with 100% initial recovered potency Dextran 40K and Poloxamer 188 together in sodium citrate buffer (pH 6.5)

(Table 4)); and potassium phosphate buffer (pH 5.5) (compare 39% initial recovered potency of Poloxamer 188 alone in potassium phosphate buffer (pH 5.5) (Table 2) with 103% initial recovered potency Dextran 40K and Poloxamer 188 together in potassium phosphate buffer (pH 5.5) (Table 4)).

Clostridial toxin pharmaceutical compositions comprising PVP 17 and a surfactant resulted in an effective increased recovered potency and long-term stability of the Clostridial toxin active ingredient over a wide range of excipient amounts. For example, when used as the sole excipient, PVP 17 was effective at increasing recovered potency at amounts ranging from about 5 mg to about 20 mg (about 0.5% (w/v) to about 2% (w/v)). As discussed above, Poloxamer 188 alone resulted in no detectable recovered potency of a Clostridial toxin active ingredient. However, about 0.3125 mg to about 2.5 mg of PVP 17 (about 0.03% (w/v) to about 0.25% (w/v)) in combination with from about 0.625 mg to about 5 mg of Poloxamer 188 (about 0.06% (w/v) to about 0.5% (w/v)) increased recovered potency of the Clostridial toxin active ingredient to about 64% to about 80% (each of these excipients at these concentrations alone resulted in no detectable recovery). Similarly, about 30 mg to about 60 mg of PVP 17 (about 3% (w/v) to about 6% (w/v)) in combination with from about 1.5 mg to about 5 mg of Poloxamer 188 (about 0.15% (w/v) to about 0.5% (w/v)) increased recovered potency of the Clostridial toxin active ingredient to about 68% to about 77% (each of these excipients at these concentrations alone resulted in no detectable recovery). The addition of various buffers or sodium chloride to Clostridial toxin pharmaceutical compositions comprising PVP 17 and Poloxamer 188 did not appear to have a great affect on initial recovered potency or long-term stability of the Clostridial toxin active ingredient (Table 4).

TABLE 4

Formulations using Botulinum Neurotoxin Complex[a] - Two Excipients with One Being a Non-Protein Polymer

| Excipient 1 | | Excipient 2 | | | | Recovered Potency[b] (%) | | | | |
|---|---|---|---|---|---|---|---|---|---|---|
| | | | | | | | Ambient Temperatrue[c] | | Below Frerezing Temperature[d] | |
| Type | Amount (mg) | Type | Amount (mg) | Ratio | Solution (pH) | Initial | 3 months | 12 months | 3 months | 12 months |
| Dextran 3K | 55 | PEG 3350 | 5.5 | 10:1 | Water (pH 7.1) | 0 | 0 | 0 | 0 | 0 |
| Dextran 3K | 40 | PEG 3350 | 20 | 2:1 | Water (pH 6.3) | 82 | 0 | 0 | 0 | 0 |
| Dextran 3K | 30 | PEG 3350 | 30 | 1:1 | Water (pH 6.4) | 0 | 0 | 0 | 0 | 0 |
| Dextran 3K | 20 | PEG 3350 | 40 | 1:2 | Water (pH 6.7) | 47 | 0 | 0 | 0 | 0 |
| Dextran 3K | 5.5 | PEG 3350 | 55 | 1:10 | Water (pH 6.9) | 47 | 0 | 0 | 0 | 0 |
| Dextran 3K | 55 | PEG 3350 | 5.5 | 10:1 | 10 mM SC (pH 5.5) | 82 | 0 | 0 | 92 | 94 |
| Dextran 3K | 40 | PEG 3350 | 20 | 2:1 | 10 mM SC (pH 5.5) | 86 | 0 | 0 | 92 | 92 |
| Dextran 3K | 30 | PEG 3350 | 30 | 1:1 | 10 mM SC (pH 5.5) | 92 | 0 | 0 | 88 | 90 |
| Dextran 3K | 20 | PEG 3350 | 40 | 1:2 | 10 mM SC (pH 5.5) | 82 | 0 | 0 | 82 | 81 |
| Dextran 3K | 5.5 | PEG 3350 | 55 | 1:10 | 10 mM SC (pH 5.5) | 92 | 0 | 0 | 82 | 82 |
| Dextran 3K | 55 | PEG 3350 | 5.5 | 10:1 | 10 mM SC (pH 6.5) | 104 | 0 | 0 | 81 | 80 |
| Dextran 3K | 40 | PEG 3350 | 20 | 2:1 | 10 mM SC (pH 6.5) | 104 | 0 | 0 | 92 | 92 |
| Dextran 3K | 30 | PEG 3350 | 30 | 1:1 | 10 mM SC (pH 6.5) | 82 | 0 | 0 | 82 | 102 |
| Dextran 3K | 20 | PEG 3350 | 40 | 1:2 | 10 mM SC (pH 6.5) | 82 | 0 | 0 | 57 | 78 |
| Dextran 3K | 5.5 | PEG 3350 | 55 | 1:10 | 10 mM SC (pH 6.5) | 82 | 0 | 0 | 71 | 60 |
| Dextran 3K | 55 | PEG 3350 | 5.5 | 10:1 | 10 mM PP (pH 5.5) | 102 | 53 | 0 | 92 | 80 |
| Dextran 3K | 40 | PEG 3350 | 20 | 2:1 | 10 mM PP (pH 5.5) | 59 | 0 | 0 | 92 | 102 |
| Dextran 3K | 30 | PEG 3350 | 30 | 1:1 | 10 mM PP (pH 5.5) | 82 | 0 | 0 | 96 | 104 |
| Dextran 3K | 20 | PEG 3350 | 40 | 1:2 | 10 mM PP (pH 5.5) | 104 | 0 | 0 | 96 | 92 |
| Dextran 3K | 5.5 | PEG 3350 | 55 | 1:10 | 10 mM PP (pH 5.5) | 101 | 0 | 0 | 92 | 80 |
| Dextran 3K | 55 | PEG 3350 | 5.5 | 10:1 | 10 mM PP (pH 6.5) | 81 | 0 | 0 | 106 | 104 |
| Dextran 3K | 40 | PEG 3350 | 20 | 2:1 | 10 mM PP (pH 6.5) | 102 | 0 | 0 | 92 | 82 |
| Dextran 3K | 30 | PEG 3350 | 30 | 1:1 | 10 mM PP (pH 6.5) | 82 | 0 | 0 | 82 | 88 |
| Dextran 3K | 20 | PEG 3350 | 40 | 1:2 | 10 mM PP (pH 6.5) | 104 | 0 | 0 | 88 | 88 |
| Dextran 3K | 5.5 | PEG 3350 | 55 | 1:10 | 10 mM PP (pH 6.5) | 102 | 0 | 0 | 85 | 82 |
| Dextran 3K | 55 | PEG 3350 | 5.5 | 10:1 | 10 mM HB (pH 5.5) | 104 | 46 | 0 | 74 | 92 |
| Dextran 3K | 40 | PEG 3350 | 20 | 2:1 | 10 mM HB (pH 5.5) | 104 | 0 | 0 | 92 | 82 |
| Dextran 3K | 30 | PEG 3350 | 30 | 1:1 | 10 mM HB (pH 5.5) | 80 | 0 | 0 | 75 | 78 |
| Dextran 3K | 20 | PEG 3350 | 40 | 1:2 | 10 mM HB (pH 5.5) | 96 | 0 | 0 | 65 | 94 |
| Dextran 3K | 5.5 | PEG 3350 | 55 | 1:10 | 10 mM HB (pH 5.5) | 82 | 46 | 0 | 94 | 92 |
| Dextran 3K | 55 | PEG 3350 | 5.5 | 10:1 | 10 mM HB (pH 6.5) | 68 | 0 | 0 | 72 | 78 |
| Dextran 3K | 40 | PEG 3350 | 20 | 2:1 | 10 mM HB (pH 6.5) | 87 | 0 | 0 | 90 | 68 |
| Dextran 3K | 30 | PEG 3350 | 30 | 1:1 | 10 mM HB (pH 6.5) | 84 | 0 | 0 | 82 | 60 |
| Dextran 3K | 20 | PEG 3350 | 40 | 1:2 | 10 mM HB (pH 6.5) | 70 | 0 | 0 | 78 | 78 |
| Dextran 3K | 5.5 | PEG 3350 | 55 | 1:10 | 10 mM HB (pH 6.5) | 66 | 0 | 0 | 61 | 54 |
| Dextran 3K | 60 | Poloxamer 188 | 3 | 20:1 | Water (pH 5.6) | 98 | 57 | 57 | 120 | 128 |
| Dextran 3K | 55 | Poloxamer 188 | 5.5 | 10:1 | Water (pH 5.9) | 78 | 0 | 0 | 114 | 128 |
| Dextran 3K | 40 | Poloxamer 188 | 20 | 2:1 | Water (pH 6.5) | 98 | 0 | 0 | 128 | 69 |
| Dextran 3K | 60 | Poloxamer 188 | 3 | 20:1 | 10 mM SC (pH 5.5) | 100 | 0 | 0 | 103 | 105 |
| Dextran 3K | 55 | Poloxamer 188 | 5.5 | 10:1 | 10 mM SC (pH 5.5) | 82 | 0 | 0 | 120 | 115 |
| Dextran 3K | 40 | Poloxamer 188 | 20 | 2:1 | 10 mM SC (pH 5.5) | 85 | 0 | 0 | 130 | 130 |
| Dextran 3K | 60 | Poloxamer 188 | 3 | 20:1 | 10 mM SC (pH 6.5) | 99 | 0 | 0 | 78 | 125 |
| Dextran 3K | 55 | Poloxamer 188 | 5.5 | 10:1 | 10 mM SC (pH 6.5) | 85 | 0 | 0 | 128 | 130 |
| Dextran 3K | 40 | Poloxamer 188 | 20 | 2:1 | 10 mM SC (pH 6.5) | 93 | 0 | 0 | 107 | 128 |
| Dextran 3K | 60 | Poloxamer 188 | 3 | 20:1 | 10 mM PP (pH 5.5) | 90 | 57 | 57 | 67 | 130 |
| Dextran 3K | 55 | Poloxamer 188 | 5.5 | 10:1 | 10 mM PP (pH 5.5) | 95 | 55 | 55 | 128 | 130 |
| Dextran 3K | 40 | Poloxamer 188 | 20 | 2:1 | 10 mM PP (pH 5.5) | 120 | 0 | 0 | 115 | 115 |
| Dextran 3K | 60 | Poloxamer 188 | 3 | 20:1 | 10 mM PP (pH 6.5) | 86 | 0 | 0 | 89 | 133 |

TABLE 4-continued

Formulations using Botulinum Neurotoxin Complex[a] - Two Excipients with One Being a Non-Protein Polymer

| Excipient 1 | | Excipient 2 | | | | Recovered Potency[b] (%) | | | | |
|---|---|---|---|---|---|---|---|---|---|---|
| | | | | | | | Ambient Temperatrue[c] | | Below Frerezing Temperature[d] | |
| Type | Amount (mg) | Type | Amount (mg) | Ratio | Solution (pH) | Initial | 3 months | 12 months | 3 months | 12 months |
| Dextran 3K | 55 | Poloxamer 188 | 5.5 | 10:1 | 10 mM PP (pH 6.5) | 98 | 0 | 0 | 120 | 103 |
| Dextran 3K | 40 | Poloxamer 188 | 20 | 2:1 | 10 mM PP (pH 6.5) | 82 | 0 | 0 | 70 | 113 |
| Dextran 3K | 60 | Poloxamer 188 | 3 | 20:1 | 10 mM HB (pH 5.5) | 103 | 0 | 0 | 104 | 110 |
| Dextran 3K | 55 | Poloxamer 188 | 5.5 | 10:1 | 10 mM HB (pH 5.5) | 122 | 74 | 0 | 128 | 103 |
| Dextran 3K | 40 | Poloxamer 188 | 20 | 2:1 | 10 mM HB (pH 5.5) | 125 | 59 | 0 | 103 | 122 |
| Dextran 3K | 60 | Poloxamer 188 | 3 | 20:1 | 10 mM HB (pH 6.5) | 134 | 0 | 0 | 127 | 103 |
| Dextran 3K | 55 | Poloxamer 188 | 5.5 | 10:1 | 10 mM HB (pH 6.5) | 115 | 0 | 0 | 128 | 110 |
| Dextran 3K | 40 | Poloxamer 188 | 20 | 2:1 | 10 mM HB (pH 6.5) | 115 | 0 | 0 | 128 | 108 |
| Dextran 40K | 60 | Poloxamer 188 | 3 | 20:1 | Water (pH 5.8) | 87 | 0 | 0 | 76 | 78 |
| Dextran 40K | 55 | Poloxamer 188 | 5.5 | 10:1 | Water (pH 6.0) | 85 | 0 | 0 | 78 | 77 |
| Dextran 40K | 40 | Poloxamer 188 | 20 | 2:1 | Water (pH 6.5) | 128 | 0 | 0 | 75 | 90 |
| Dextran 40K | 60 | Poloxamer 188 | 3 | 20:1 | 10 mM SC (pH 5.5) | 102 | 0 | 0 | 100 | 74 |
| Dextran 40K | 55 | Poloxamer 188 | 5.5 | 10:1 | 10 mM SC (pH 5.5) | 115 | 0 | 0 | 83 | 115 |
| Dextran 40K | 40 | Poloxamer 188 | 20 | 2:1 | 10 mM SC (pH 5.5) | 128 | 0 | 0 | 98 | 113 |
| Dextran 40K | 60 | Poloxamer 188 | 3 | 20:1 | 10 mM SC (pH 6.5) | 100 | 0 | 0 | 98 | 98 |
| Dextran 40K | 55 | Poloxamer 188 | 5.5 | 10:1 | 10 mM SC (pH 6.5) | 84 | 0 | 0 | 87 | 69 |
| Dextran 40K | 40 | Poloxamer 188 | 20 | 2:1 | 10 mM SC (pH 6.5) | 100 | 0 | 0 | 134 | 98 |
| Dextran 40K | 60 | Poloxamer 188 | 3 | 20:1 | 10 mM PP (pH 5.5) | 109 | 0 | 0 | 78 | 91 |
| Dextran 40K | 55 | Poloxamer 188 | 5.5 | 10:1 | 10 mM PP (pH 5.5) | 99 | 0 | 0 | 98 | 100 |
| Dextran 40K | 40 | Poloxamer 188 | 20 | 2:1 | 10 mM PP (pH 5.5) | 103 | 0 | 0 | 103 | 100 |
| Dextran 40K | 60 | Poloxamer 188 | 3 | 20:1 | 10 mM PP (pH 6.5) | 110 | 0 | 0 | 83 | 98 |
| Dextran 40K | 55 | Poloxamer 188 | 5.5 | 10:1 | 10 mM PP (pH 6.5) | 102 | 0 | 0 | 97 | 73 |
| Dextran 40K | 40 | Poloxamer 188 | 20 | 2:1 | 10 mM PP (pH 6.5) | 115 | 0 | 0 | 94 | 115 |
| Dextran 40K | 60 | Poloxamer 188 | 3 | 20:1 | 10 mM HB (pH 5.5) | 99 | 0 | 0 | 100 | 100 |
| Dextran 40K | 55 | Poloxamer 188 | 5.5 | 10:1 | 10 mM HB (pH 5.5) | 115 | 62 | 0 | 91 | 72 |
| Dextran 40K | 40 | Poloxamer 188 | 20 | 2:1 | 10 mM HB (pH 5.5) | 130 | 58 | 0 | 112 | 110 |
| Dextran 40K | 60 | Poloxamer 188 | 3 | 20:1 | 10 mM HB (pH 6.5) | 110 | 0 | 0 | 98 | 98 |
| Dextran 40K | 55 | Poloxamer 188 | 5.5 | 10:1 | 10 mM HB (pH 6.5) | 110 | 0 | 0 | 97 | 75 |
| Dextran 40K | 40 | Poloxamer 188 | 20 | 2:1 | 10 mM HB (pH 6.5) | 128 | 0 | 0 | 110 | 130 |
| PVP 17 | 55 | PEG 3350 | 5.5 | 10:1 | Water (pH 6.5) | 0 | 0 | 0 | 0 | 0 |
| PVP 17 | 40 | PEG 3350 | 20 | 2:1 | Water (pH 4.6) | 80 | 0 | 0 | 70 | 70 |
| PVP 17 | 30 | PEG 3350 | 30 | 1:1 | Water (pH 5.0) | 80 | 0 | 0 | 62 | 62 |
| PVP 17 | 20 | PEG 3350 | 40 | 1:2 | Water (pH 5.4) | 68 | 0 | 0 | 66 | 66 |
| PVP 17 | 5.5 | PEG 3350 | 55 | 1:10 | Water (pH 4.1) | 47 | 0 | 0 | 54 | 54 |
| PVP 17 | 55 | PEG 3350 | 5.5 | 10:1 | 10 mM SC (pH 5.5) | 92 | 0 | 0 | 78 | 78 |
| PVP 17 | 40 | PEG 3350 | 20 | 2:1 | 10 mM SC (pH 5.5) | 76 | 0 | 0 | 69 | 69 |
| PVP 17 | 30 | PEG 3350 | 30 | 1:1 | 10 mM SC (pH 5.5) | 80 | 0 | 0 | 68 | 68 |
| PVP 17 | 20 | PEG 3350 | 40 | 1:2 | 10 mM SC (pH 5.5) | 92 | 0 | 0 | 78 | 78 |
| PVP 17 | 5.5 | PEG 3350 | 55 | 1:10 | 10 mM SC (pH 5.5) | 83 | 0 | 0 | 64 | 64 |
| PVP 17 | 55 | PEG 3350 | 5.5 | 10:1 | 10 mM SC (pH 6.5) | — | — | — | — | — |
| PVP 17 | 40 | PEG 3350 | 20 | 2:1 | 10 mM SC (pH 6.5) | — | — | — | — | — |
| PVP 17 | 30 | PEG 3350 | 30 | 1:1 | 10 mM SC (pH 6.5) | — | — | — | — | — |
| PVP 17 | 20 | PEG 3350 | 40 | 1:2 | 10 mM SC (pH 6.5) | — | — | — | — | — |
| PVP 17 | 5.5 | PEG 3350 | 55 | 1:10 | 10 mM SC (pH 6.5) | — | — | — | — | — |
| PVP 17 | 55 | PEG 3350 | 5.5 | 10:1 | 10 mM PP (pH 5.5) | — | — | — | — | — |
| PVP 17 | 40 | PEG 3350 | 20 | 2:1 | 10 mM PP (pH 5.5) | — | — | — | — | — |
| PVP 17 | 30 | PEG 3350 | 30 | 1:1 | 10 mM PP (pH 5.5) | — | — | — | — | — |
| PVP 17 | 20 | PEG 3350 | 40 | 1:2 | 10 mM PP (pH 5.5) | — | — | — | — | — |
| PVP 17 | 5.5 | PEG 3350 | 55 | 1:10 | 10 mM PP (pH 5.5) | — | — | — | — | — |
| PVP 17 | 55 | PEG 3350 | 5.5 | 10:1 | 10 mM PP (pH 6.5) | — | — | — | — | — |
| PVP 17 | 40 | PEG 3350 | 20 | 2:1 | 10 mM PP (pH 6.5) | — | — | — | — | — |
| PVP 17 | 30 | PEG 3350 | 30 | 1:1 | 10 mM PP (pH 6.5) | — | — | — | — | — |
| PVP 17 | 20 | PEG 3350 | 40 | 1:2 | 10 mM PP (pH 6.5) | — | — | — | — | — |
| PVP 17 | 5.5 | PEG 3350 | 55 | 1:10 | 10 mM PP (pH 6.5) | — | — | — | — | — |
| PVP 17 | 55 | PEG 3350 | 5.5 | 10:1 | 10 mM HB (pH 5.5) | 92 | 42 | 42 | 54 | 54 |
| PVP 17 | 40 | PEG 3350 | 20 | 2:1 | 10 mM HB (pH 5.5) | 92 | 0 | 0 | 98 | 98 |
| PVP 17 | 30 | PEG 3350 | 30 | 1:1 | 10 mM HB (pH 5.5) | 109 | 0 | 0 | 112 | 112 |
| PVP 17 | 20 | PEG 3350 | 40 | 1:2 | 10 mM HB (pH 5.5) | 84 | 0 | 0 | 61 | 61 |
| PVP 17 | 5.5 | PEG 3350 | 55 | 1:10 | 10 mM HB (pH 5.5) | 92 | 0 | 0 | 78 | 78 |
| PVP 17 | 55 | PEG 3350 | 5.5 | 10:1 | 10 mM HB (pH 6.5) | 86 | 0 | 0 | 78 | 78 |
| PVP 17 | 40 | PEG 3350 | 20 | 2:1 | 10 mM HB (pH 6.5) | 92 | 0 | 0 | 102 | 102 |
| PVP 17 | 30 | PEG 3350 | 30 | 1:1 | 10 mM HB (pH 6.5) | 78 | 0 | 0 | 74 | 74 |
| PVP 17 | 20 | PEG 3350 | 40 | 1:2 | 10 mM HB (pH 6.5) | 104 | 46 | 46 | 92 | 92 |
| PVP 17 | 5.5 | PEG 3350 | 55 | 1:10 | 10 mM HB (pH 6.5) | 102 | 61 | 61 | 80 | 80 |
| PVP 17 | 10 | Poloxamer 188 | 0.25 | 40:1 | Water (pH 4.3) | 64 | 0 | 0 | 82 | 78 |
| PVP 17 | 5 | Poloxamer 188 | 0.125 | 40:1 | Water (pH 4.2) | 80 | 0 | 0 | 76 | 61 |
| PVP 17 | 60 | Poloxamer 188 | 3 | 20:1 | Water (pH 4.0) | 68 | 0 | 0 | 72 | 72 |
| PVP 17 | 30 | Poloxamer 188 | 1.5 | 20:1 | Water (pH 4.0) | 77 | 0 | 0 | 68 | 80 |
| PVP 17 | 10 | Poloxamer 188 | 0.5 | 20:1 | Water (pH 4.3) | 82 | 0 | 0 | 82 | 68 |
| PVP 17 | 5 | Poloxamer 188 | 0.25 | 20:1 | Water (pH 4.2) | 79 | 0 | 0 | 82 | 62 |

TABLE 4-continued

Formulations using Botulinum Neurotoxin Complex[a] - Two Excipients with One Being a Non-Protein Polymer

| Excipient 1 | | Excipient 2 | | | | | Recovered Potency[b] (%) | | | |
| --- | --- | --- | --- | --- | --- | --- | --- | --- | --- | --- |
| | | | | | | | | Ambient Temperatrue[c] | | Below Frerezing Temperature[d] |
| Type | Amount (mg) | Type | Amount (mg) | Ratio | Solution (pH) | Initial | 3 months | 12 months | 3 months | 12 months |
| PVP 17 | 55 | Poloxamer 188 | 5 | 10:1 | Water (pH 4.1) | 78 | 0 | 0 | 53 | 71 |
| PVP 17 | 27 | Poloxamer 188 | 2.7 | 10:1 | Water (pH 4.1) | 82 | 0 | 0 | 53 | 81 |
| PVP 17 | 48 | Poloxamer 188 | 12 | 4:1 | Water (pH 4.1) | 73 | 0 | 0 | 82 | 65 |
| PVP 17 | 24 | Poloxamer 188 | 6 | 4:1 | Water (pH 4.1) | 78 | 0 | 0 | 53 | 65 |
| PVP 17 | 10 | Poloxamer 188 | 2.5 | 4:1 | Water (pH 4.3) | 78 | 0 | 0 | 82 | 82 |
| PVP 17 | 5 | Poloxamer 188 | 1.25 | 4:1 | Water (pH 4.3) | 80 | 0 | 0 | 68 | 68 |
| PVP 17 | 40 | Poloxamer 188 | 20 | 2:1 | Water (pH 4.3) | 74 | 0 | 0 | 78 | 72 |
| PVP 17 | 20 | Poloxamer 188 | 10 | 2:1 | Water (pH 4.4) | 71 | 0 | 0 | 101 | 97 |
| PVP 17 | 10 | Poloxamer 188 | 5 | 2:1 | Water (pH 4.4) | 79 | 0 | 0 | 83 | 74 |
| PVP 17 | 5 | Poloxamer 188 | 2.5 | 2:1 | Water (pH 4.4) | 63 | 0 | 0 | 82 | 70 |
| PVP 17 | 20 | Poloxamer 188 | 40 | 1:2 | Water (pH 5.7) | 69 | 0 | 0 | 61 | 67 |
| PVP 17 | 10 | Poloxamer 188 | 20 | 1:2 | Water (pH 5.2) | 77 | 0 | 0 | 91 | 64 |
| PVP 17 | 5 | Poloxamer 188 | 10 | 1:2 | Water (pH 5.4) | 82 | 0 | 0 | 117 | 68 |
| PVP 17 | 2.5 | Poloxamer 188 | 5 | 1:2 | Water (pH 5.3) | 80 | 0 | 0 | 70 | 66 |
| PVP 17 | 1.25 | Poloxamer 188 | 2.5 | 1:2 | Water (pH 5.3) | 70 | — | — | 53 | 47 |
| PVP 17 | 0.625 | Poloxamer 188 | 1.25 | 1:2 | Water (pH 5.4) | 73 | — | — | 55 | 78 |
| PVP 17 | 0.3125 | Poloxamer 188 | 0.625 | 1:2 | Water (pH 5.2) | 64 | — | — | 62 | 78 |
| PVP 17 | 0.5 | Poloxamer 188 | 10 | 1:20 | Water (pH 6.4) | 79 | 0 | 0 | 58 | 59 |
| PVP 17 | 0.25 | Poloxamer 188 | 5 | 1:20 | Water (pH 6.4) | 82 | 0 | 0 | 62 | 0 |
| PVP 17 | 55 | Poloxamer 188 | 5.5 | 2:1 | 10 mM SC (pH 5.5) | 86 | 39 | 0 | 78 | 82 |
| PVP 17 | 40 | Poloxamer 188 | 20 | 2:1 | 10 mM SC (pH 5.5) | 86 | 41 | 0 | 88 | 94 |
| PVP 17 | 20 | Poloxamer 188 | 10 | 2:1 | 10 mM SC (pH 5.5) | 65 | 65 | 0 | 101 | 105 |
| PVP 17 | 20 | Poloxamer 188 | 10 | 2:1 | 10 mM SC (pH 6.5) | 87 | 0 | 0 | 97 | 102 |
| PVP 17 | 20 | Poloxamer 188 | 10 | 2:1 | 10 mM PP (pH 5.5) | 71 | 0 | 0 | 79 | 79 |
| PVP 17 | 20 | Poloxamer 188 | 10 | 2:1 | 10 mM PP (pH 6.5) | 65 | 0 | 0 | 63 | 65 |
| PVP 17 | 40 | Poloxamer 188 | 20 | 2:1 | 10 mM NaCl (pH 4.2) | 104 | 0 | 0 | 96 | 104 |
| PVP 17 | 20 | Poloxamer 188 | 10 | 2:1 | 10 mM NaCl (pH 4.4) | 91 | 0 | 0 | 93 | 115 |
| PVP 17 | 10 | Poloxamer 188 | 20 | 1:2 | Water (pH 5.2) | 77 | 0 | 0 | 91 | 64 |
| PVP 17 | 20 | Poloxamer 188 | 40 | 1:2 | 10 mM SC (pH 5.5) | 92 | 39 | 0 | 83 | 96 |
| PVP 17 | 10 | Poloxamer 188 | 20 | 1:2 | 10 mM SC (pH 5.5) | 81 | 71 | 49 | 97 | 85 |
| PVP 17 | 2.5 | Poloxamer 188 | 5 | 1:2 | 10 mM SC (pH 5.5) | 104 | — | — | 76 | 73 |
| PVP 17 | 1.25 | Poloxamer 188 | 2.5 | 1:2 | 10 mM SC (pH 5.5) | 72 | — | — | 92 | 90 |
| PVP 17 | 0.625 | Poloxamer 188 | 1.25 | 1:2 | 10 mM SC (pH 5.5) | 102 | — | — | 102 | 88 |
| PVP 17 | 0.3125 | Poloxamer 188 | 0.625 | 1:2 | 10 mM SC (pH 5.5) | 84 | — | — | 78 | 90 |
| PVP 17 | 10 | Poloxamer 188 | 20 | 1:2 | 10 mM SC (pH 6.5) | 88 | 0 | 0 | 79 | 91 |
| PVP 17 | 10 | Poloxamer 188 | 20 | 1:2 | 10 mM PP (pH 5.5) | 68 | 0 | 0 | 73 | 89 |
| PVP 17 | 10 | Poloxamer 188 | 20 | 1:2 | 10 mM PP (pH 6.5) | 88 | 0 | 0 | 88 | 88 |
| PVP 17 | 60 | Poloxamer 188 | 3 | 20:1 | 10 mM HB (pH 5.5) | 79 | 0 | 0 | 80 | 80 |
| PVP 17 | 55 | Poloxamer 188 | 5.5 | 10:1 | 10 mM HB (pH 5.5) | 92 | 0 | 0 | 0 | 0 |
| PVP 17 | 40 | Poloxamer 188 | 20 | 2:1 | 10 mM HB (pH 5.5) | 72 | 0 | 0 | 92 | 92 |
| PVP 17 | 20 | Poloxamer 188 | 40 | 1:2 | 10 mM HB (pH 5.5) | 106 | 42 | 42 | 102 | 102 |
| PVP 17 | 60 | Poloxamer 188 | 3 | 20:1 | 10 mM HB (pH 6.5) | 104 | 46 | 46 | 100 | 100 |
| PVP 17 | 55 | Poloxamer 188 | 5.5 | 10:1 | 10 mM HB (pH 6.5) | 112 | 0 | 0 | 91 | 91 |
| PVP 17 | 40 | Poloxamer 188 | 20 | 2:1 | 10 mM HB (pH 6.5) | 91 | 0 | 0 | 102 | 102 |
| PVP 17 | 20 | Poloxamer 188 | 40 | 1:2 | 10 mM HB (pH 6.5) | 100 | 0 | 0 | 0 | 0 |
| PVP 17 | 60 | Poloxamer 188 | 3 | 20:1 | 10 mM NaCl (pH 3.0) | 58 | 0 | 0 | 54 | 54 |
| PVP 17 | 30 | Poloxamer 188 | 1.5 | 10:1 | 10 mM NaCl (pH 3.0) | 78 | 0 | 0 | 80 | 92 |
| PVP 17 | 55 | Poloxamer 188 | 5.5 | 10:1 | 10 mM NaCl (pH 4.0) | 68 | 0 | 0 | 92 | 92 |
| PVP 17 | 27 | Poloxamer 188 | 2.7 | 10:1 | 10 mM NaCl (pH 4.0) | 76 | 0 | 0 | 88 | 83 |
| PVP 17 | 48 | Poloxamer 188 | 12 | 4:1 | 10 mM NaCl (pH 4.1) | 92 | — | — | 82 | 82 |
| PVP 17 | 24 | Poloxamer 188 | 6 | 4:1 | 10 mM NaCl (pH 4.1) | 102 | 0 | 0 | 78 | 79 |
| PVP 17 | 40 | Poloxamer 188 | 20 | 2:1 | 10 mM NaCl (pH 4.3) | 102 | — | — | 55 | 55 |
| PVP 17 | 20 | Poloxamer 188 | 10 | 2:1 | 10 mM NaCl (pH 4.3) | 78 | 0 | 0 | 88 | 82 |
| PVP 17 | 10 | Poloxamer 188 | 20 | 1:2 | 10 mM NaCl (pH 4.7) | 115 | 0 | 0 | 80 | 81 |
| PVP 17 | 2.5 | Poloxamer 188 | 5 | 1:2 | 10 mM NaCl (pH 5.2) | 94 | — | — | 101 | 79 |
| PVP 17 | 1.25 | Poloxamer 188 | 2.5 | 1:2 | 10 mM NaCl (pH 5.2) | 88 | — | — | 100 | 102 |
| PVP 17 | 0.625 | Poloxamer 188 | 1.25 | 1:2 | 10 mM NaCl (pH 5.2) | 96 | — | — | 98 | 77 |
| PVP 17 | 0.3125 | Poloxamer 188 | 0.625 | 1:2 | 10 mM NaCl (pH 5.2) | 85 | — | — | 76 | 80 |
| PVP 17 | 10 | Polysorbate 80 | 0.5 | 20:1 | Water (pH 4.2) | 82 | — | — | 81 | 81 |
| PVP 17 | 5 | Polysorbate 80 | 0.25 | 20:1 | Water (pH 4.2) | 84 | — | — | 77 | 77 |
| PVP 17 | 10 | Polysorbate 80 | 2.5 | 4:1 | Water (pH 4.4) | 90 | — | — | 82 | 82 |
| PVP 17 | 5 | Polysorbate 80 | 1.25 | 4:1 | Water (pH 4.4) | 90 | — | — | 104 | 104 |
| PEG 3350 | 50 | Mannitol | 5 | 10:1 | Water | 0 | 0 | 0 | 0 | 0 |
| PEG 3350 | 50 | Mannitol | 50 | 1:1 | Water | 26 | — | — | — | — |
| PEG 3350 | 5 | Mannitol | 50 | 1:10 | Water | 30 | — | — | — | — |
| PEG 3350 | 60 | Poloxamer 188 | 3 | 20:1 | Water (pH 7.0) | 0 | 0 | 0 | 0 | 0 |
| PEG 3350 | 55 | Poloxamer 188 | 5.5 | 10:1 | Water (pH 7.0) | 0 | 0 | 0 | 0 | 0 |
| PEG 3350 | 50 | Poloxamer 188 | 5 | 10:1 | Water (pH 7.0) | 0 | 0 | 0 | 0 | 0 |
| PEG 3350 | 40 | Poloxamer 188 | 20 | 2:1 | Water (pH 7.0) | 0 | 0 | 0 | 0 | 0 |
| PEG 3350 | 50 | Poloxamer 188 | 50 | 1:1 | Water | 0 | 0 | 0 | 0 | 0 |

TABLE 4-continued

Formulations using Botulinum Neurotoxin Complex[a] - Two Excipients with One Being a Non-Protein Polymer

| Excipient 1 | | Excipient 2 | | | | Recovered Potency[b] (%) | | | | |
|---|---|---|---|---|---|---|---|---|---|---|
| | | | | | | Ambient Temperatrue[c] | | | Below Frerezing Temperature[d] | |
| Type | Amount (mg) | Type | Amount (mg) | Ratio | Solution (pH) | Initial | 3 months | 12 months | 3 months | 12 months |
| PEG 3350 | 5 | Poloxamer 188 | 50 | 1:10 | Water | 0 | 0 | 0 | 0 | 0 |
| PEG 3350 | 60 | Poloxamer 188 | 3 | 20:1 | 10 mM SC (pH 5.5) | 101 | 66 | 46 | 94 | 95 |
| PEG 3350 | 55 | Poloxamer 188 | 5.5 | 10:1 | 10 mM SC (pH 5.5) | 90 | 59 | 0 | 87 | 94 |
| PEG 3350 | 40 | Poloxamer 188 | 20 | 2:1 | 10 mM SC (pH 5.5) | 101 | 59 | 0 | 98 | 99 |
| PEG 3350 | 60 | Poloxamer 188 | 3 | 20:1 | 10 mM SC (pH 6.5) | 70 | 0 | 0 | 58 | 70 |
| PEG 3350 | 55 | Poloxamer 188 | 5.5 | 10:1 | 10 mM SC (pH 6.5) | 66 | 0 | 0 | 58 | 66 |
| PEG 3350 | 40 | Poloxamer 188 | 20 | 2:1 | 10 mM SC (pH 6.5) | 76 | 0 | 0 | 69 | 66 |
| PEG 3350 | 60 | Poloxamer 188 | 3 | 20:1 | 10 mM PP (pH 5.5) | 92 | 0 | 0 | 87 | 77 |
| PEG 3350 | 55 | Poloxamer 188 | 5.5 | 10:1 | 10 mM PP (pH 5.5) | 98 | 0 | 0 | 86 | 101 |
| PEG 3350 | 40 | Poloxamer 188 | 20 | 2:1 | 10 mM PP (pH 5.5) | 83 | 0 | 0 | 96 | 78 |
| PEG 3350 | 60 | Poloxamer 188 | 3 | 20:1 | 10 mM PP (pH 6.5) | 0 | 0 | 0 | 0 | 0 |
| PEG 3350 | 55 | Poloxamer 188 | 5.5 | 10:1 | 10 mM PP (pH 6.5) | 0 | 0 | 0 | 0 | 0 |
| PEG 3350 | 40 | Poloxamer 188 | 20 | 2:1 | 10 mM PP (pH 6.5) | 0 | 0 | 0 | 0 | 0 |
| PEG 3350 | 60 | Poloxamer 188 | 3 | 20:1 | 10 mM HB (pH 5.5) | 75 | 78 | 76 | 91 | 101 |
| PEG 3350 | 55 | Poloxamer 188 | 5.5 | 10:1 | 10 mM HB (pH 5.5) | 98 | 98 | 63 | 98 | 73 |
| PEG 3350 | 40 | Poloxamer 188 | 20 | 2:1 | 10 mM HB (pH 5.5) | 72 | 82 | 65 | 83 | 89 |
| PEG 3350 | 60 | Poloxamer 188 | 3 | 20:1 | 10 mM HB (pH 6.5) | 85 | 109 | 101 | 112 | 92 |
| PEG 3350 | 55 | Poloxamer 188 | 5.5 | 10:1 | 10 mM HB (pH 6.5) | 81 | 101 | 82 | 136 | 87 |
| PEG 3350 | 40 | Poloxamer 188 | 20 | 2:1 | 10 mM HB (pH 6.5) | 65 | 106 | 85 | 120 | 109 |
| PEG 3350 | 50 | Glycine | 5 | 10:1 | Water | 0 | 0 | 0 | 0 | 0 |
| PEG 3350 | 50 | Glycine | 50 | 1:1 | Water | 0 | 0 | 0 | 0 | 0 |
| PEG 3350 | 5 | Glycine | 50 | 1:10 | Water | 0 | 0 | 0 | 0 | 0 |

[a]Amount of botulinum neurotoxin serotype A complex added per formulation was 150 units. Total volume of formulation was 1.0 mL.
[b]Recovery is expressed as a percentage and is calculated by dividing the potency of the active ingredient determined after reconstitution divided by the potency of the active ingredient determined before addition to the formulation. 3 months refers to the length of time a formulation was minimally stored at the indicated temperature. 12 months refers to the length of time a formulation was minimally stored at the indicated temperature.
[c]Ambient temperature is between about 18° C. to about 22° C.
[d]Below freezing temperature is between about −5° C. to about −20° C.

Similar increased initial recovered potency of the Clostridial toxin active ingredient was observed with PVP 17 in combination with Polysorbate 80 (Table 4). Clostridial toxin compositions comprising about 5 mg to about 10 mg of PVP 17 (about 0.5% (w/v) to about 1% (w/V)) as the sole excipient resulted in about 48% to about 52% recovered potency of a Clostridial toxin active ingredient (Table 2). However, Clostridial toxin compositions comprising about 5 mg to about 10 mg of PVP 17 (about 0.5% (w/v) to about 1% (w/V)) and about 0.25 mg to about 2.5 mg polysorbate 80 (about 0.025% (w/v) to about 0.25% (w/v)) resulted in an initial recovered potency of about 82% to about 90% (Table 4). The enhancement of long term stability was also observed in Clostridial toxin compositions comprising about sucrose and polysorbate 80 (see Table 4).

Clostridial toxin pharmaceutical compositions comprising PEG 3350 and a surfactant resulted in enhanced initial recovered potency and long-term stability of the Clostridial toxin active ingredient when formulated with certain buffered solutions. For example, both PEG 3350 alone and Poloxamer 188 alone resulted in no detectable recovered potency of a Clostridial toxin active ingredient (Table 2). Similarly, Clostridial toxin pharmaceutical compositions comprising PEG 3350 and Poloxamer 188 in water resulted in no detectable recovered potency of a Clostridial toxin active ingredient (Table 4). Surprisingly, however, Clostridial toxin pharmaceutical compositions comprising PEG 3350 and Poloxamer 188 in buffered formulations all resulted in effective recovered potency of the Clostridial toxin active ingredient, and in many cases resulted in enhanced initial recovery and long-term stability (Table 4). For example, Clostridial toxin pharmaceutical compositions comprising about 60 mg PEG 3350 (about 6% (w/v)) in about pH 5.5 sodium citrate buffer resulted in an initial recovered potency of about 76%, whereas compositions comprising about 20 mg PEG 3350 (about 2% (w/v)) in about pH 5.5 sodium citrate buffer resulted in an initial recovered potency of about 81%. However, Clostridial toxin pharmaceutical compositions comprising about 40 mg to about 60 mg PEG 3350 (about 4% (w/v) to about 6% (w/v)) and about 3 mg to about 20 mg of Poloxamer 188 (about 0.3% (w/v) to about 2% (w/v)) in about pH 5.5 sodium citrate buffer resulted in an initial recovered potencies of about 90% to about 101%. Long term stability of the Clostridial toxin active ingredient was also enhanced in these formulations (Table 4).

Similarly, Clostridial toxin pharmaceutical compositions comprising about 60 mg PEG 3350 (about 6% (w/v)) in about pH 6.5 sodium citrate buffer resulted in an initial recovered potency of about 57%, whereas compositions comprising about 20 mg PEG 3350 (about 2% (w/v)) in about pH 6.5 sodium citrate buffer resulted in an initial recovered potency of about 80%. However, Clostridial toxin pharmaceutical compositions comprising about 40 mg to about 60 mg PEG 3350 (about 4% (w/v) to about 6% (w/v)) and about 3 mg to about 20 mg of Poloxamer 188 (about 0.3% (w/v) to about 2% (w/v)) in about pH 6.5 sodium citrate buffer resulted in an initial recovered potencies of about 83% to about 98%. Long term stability of the Clostridial toxin active ingredient was also enhanced in these formulations (Table 4).

Clostridial toxin pharmaceutical compositions comprising a polyol and a surfactant also resulted in recovered potency of the Clostridial toxin active ingredient. For example, both mannitol alone and Poloxamer 188 alone resulted in no detectable recovered potency of a Clostridial toxin active ingredient (Table 2). Surprisingly Clostridial toxin pharmaceutical compositions comprising mannitol and Poloxamer 188 resulted in recovered potency of the Clostridial toxin active ingredient (Table 5).

Clostridial toxin pharmaceutical compositions comprising an amino acid and a surfactant also resulted in recovered potency of the Clostridial toxin active ingredient. For example, both glycine alone and Poloxamer 188 alone resulted in no detectable recovered potency of a Clostridial toxin active ingredient (Table 2). Surprisingly Clostridial toxin pharmaceutical compositions comprising glycine and Poloxamer 188 resulted in recovered potency of about 30% to about 35% of the Clostridial toxin active ingredient (Table 5).

the Clostridial toxin active ingredient. For example, Clostridial toxin pharmaceutical compositions comprising about 10 mg sucrose (1% (w/v)) and about 10 mg PVP 17 (1% (w/v)) exhibited an initial recovered potency of the Clostridial toxin active ingredient of about 77% (Table 4). Likewise, Clostridial toxin pharmaceutical compositions comprising about 10 mg sucrose (about 1% (w/v)) and about 10 mg Poloxamer 188 (about 1% (w/v)) exhibited an initial recovered potency of the Clostridial toxin active ingredient of about 59% (Table 4). Similarly, Clostridial toxin pharmaceutical compositions comprising about 10 mg to about 20 mg of Kollodon 17 (about 1% (w/v) to about 2% (w/v)) and about 10 mg to about 20 mg Poloxamer 188 (about 1% (w/v) to about 2% (w/v)) exhibited an initial recovered

TABLE 5

Formulations using Botulinum Neurotoxin Complex[a] - Two Excipients with One Being a Surfactant

| Excipient 1 | | Excipient 2 | | | | Recovered Potency[b] (%) | | | | |
|---|---|---|---|---|---|---|---|---|---|---|
| | | | | | | | Ambient Temperatrue[c] | | Below Freerezing Temperature[d] | |
| Type | Amount (mg) | Type | Amount (mg) | Ratio | Solution (pH) | Initial | 3 months | 12 months | 3 months | 12 months |
| Poloxamer 188 | 50 | Mannitol | 5 | 10:1 | Water | 30 | — | — | — | — |
| Poloxamer 188 | 50 | Mannitol | 50 | 1:1 | Water | 33 | — | — | — | — |
| Poloxamer 188 | 5 | Mannitol | 50 | 1:10 | Water | 35 | — | — | — | — |
| Poloxamer 188 | 50 | Glycine | 5 | 10:1 | Water | 33 | — | — | — | — |
| Poloxamer 188 | 50 | Glycine | 50 | 1:1 | Water | 26 | — | — | — | — |
| Poloxamer 188 | 5 | Glycine | 50 | 1:10 | Water | 0 | 0 | 0 | 0 | 0 |

[a]Amount of botulinum neurotoxin serotype A complex added per formulation was 150 units. Total volume of formulation was 1.0 mL.
[b]Recovery is expressed as a percentage and is calculated by dividing the potency of the active ingredient determined after reconstitution divided by the potency of the active ingredient determined before addition to the formulation. 3 months refers to the length of time a formulation was minimally stored at the indicated temperature. 12 months refers to the length of time a formulation was minimally stored at the indicated temperature.
[c]Ambient temperature is between about 18° C. to about 22° C.
[d]Below freezing temperature is between about −5° C. to about −20° C.

Example 3

Non-Protein Stabilized Formulations—Three Excipients

Experiments were carried out to determine the effects of formulations comprising three different non-protein excipients on Clostridial toxin active ingredient recovery after reconstitution. The non-protein excipients tested were added separately or in combination with the listed buffers or salts (Table 6). All of the formulations were compounded, lyophilized, reconstituted and potency assessed in the same manner, and with the same Clostridial toxin active ingredient used in each formulation, except that each formulation was prepared with different non-protein excipients or with different amounts of the non-protein excipients.

The tested formulations were compounded, processed, stored and reconstituted as described in Example 1. Recovered potency was determined using the mouse LD$_{50}$ bioassay described in Example 1. Recovery is expressed as a percentage and is calculated by dividing the potency of the Clostridial toxin active ingredient in the stored reconstitution formulation by the potency of the active Clostridial toxin ingredient determined prior to its addition into the test solution. The results show that a Clostridial toxin pharmaceutical composition comprising a Clostridial toxin complex could be stabilized when the formulation comprised three non-protein excipients (Table 6).

Clostridial toxin pharmaceutical compositions comprising a sugar, a non-protein polymer and a surfactant resulted in an effective recovered potency and long-term stability of potency of the Clostridial toxin active ingredient of about 71% to about 82% (Table 4). However, Clostridial toxin pharmaceutical compositions comprising about 10 mg sucrose (about 1% (w/v)), about 10 mg PVP 17 (about 1% (w/v)), and about 10 mg Poloxamer 188 (about 1% (w/v)), exhibited a recovered potency of the Clostridial toxin active ingredient of about 102% (Table 6). A similar increase in initial recovered potency, of about 89%, was observed in Clostridial toxin pharmaceutical compositions comprising about 15 mg sucrose (about 1.5% (w/v)), about 30 mg PVP 17 (about 3% (w/v)), and about 15 mg Poloxamer 188 (about 1.5% (w/v)) (Table 6). The addition of various buffers or sodium chloride to Clostridial toxin pharmaceutical compositions comprising sucrose, PVP 17 and Poloxamer 188 enhanced initial recovered potency or long-term stability of the Clostridial toxin active ingredient, depending on the amounts of each excipient added (Table 6).

Clostridial toxin pharmaceutical compositions comprising two different sugars and a surfactant resulted in an effective recovered potency and long-term stability of the Clostridial toxin active ingredient. For example, compositions comprising sucrose, lactose and Poloxamer 188 resulted in initial recovered potency of about 81% to about 114% (Table 6). Surprisingly, Clostridial toxin pharmaceutical compositions comprising sucrose, lactose and Poloxamer 188 enhanced initial recovered potency with the addition of about pH 6.5 sodium citrate buffer. For example, Clostridial toxin pharmaceutical compositions comprising about 20 mg sucrose (about 2% (w/v)) and about 20 mg lactose (about 2% (w/v)) in about pH 6.5 sodium citrate buffer resulted in 41% initial recovered potency (Table 3).

Likewise, Clostridial toxin pharmaceutical compositions comprising about 20 mg sucrose (about 2% (w/v)) and about 10 mg Poloxamer 188 (about 1% (w/v)) in about pH 6.5 sodium citrate buffer resulted in 90% initial recovered potency (Table 3). Similarly, Clostridial toxin pharmaceutical compositions comprising about 20 mg lactose (about 2% (w/v)) and about 10 mg Poloxamer 188 (about 1% (w/v)) in about pH 6.5 sodium citrate buffer resulted in 81% initial recovered potency (Table 3). However, compositions comprising all three excipients in about pH 6.5 sodium citrate buffer resulted in about 99% initial recovered potency (Table 6).

Clostridial toxin pharmaceutical compositions comprising a sugar and two different non-protein polymers resulted in enhanced recovered potency and long-term stability of the Clostridial toxin active ingredient. For example, Clostridial toxin pharmaceutical compositions comprising about 5 mg to about 20 mg of sucrose (about 0.5% (w/v) to about 2% (w/v)) and about 5 mg to about 15 mg PVP 17 (about 0.5% (w/v) to about 1.5% (w/v)) resulted in initial recovered potency of about 58% to about 77% (Table 3). Likewise, Clostridial toxin pharmaceutical compositions comprising about 5 mg to about 50 mg of sucrose (about 0.5% (w/v) to about 5% (w/v)) and about 5 mg to about 50 mg PEG 3350 (about 0.5% (w/v) to about 5% (w/v)) resulted in initial recovered potency of about 35% to about 44% (Table 3).

Similarly, Clostridial toxin pharmaceutical compositions comprising about 30 mg to about 40 mg of PVP 17 (about 3% (w/v) to about 4% (w/v)) and about 20 mg to about 30 mg PEG 3350 (about 2% (w/v) to about 2% (w/v)) resulted in initial recovered potency of about 80% (Table 4). However, compositions comprising all three excipients resulted in about 82% to about 102% initial recovered potency (Table 6).

Clostridial toxin pharmaceutical compositions comprising two different non-protein polymers and a surfactant resulted in an effective recovered potency and long-term stability of the Clostridial toxin active ingredient. For example, Clostridial toxin pharmaceutical compositions comprising Dextran 3K, PEG 3350 and Poloxamer 188 resulted in initial recovered potencies of about 81% to about 104% when in water, about 88% to about 106% when in about pH 5.5 sodium citrate buffer, about 76% to about 96% when in about pH 6.5 sodium citrate buffer, about 87% to about 96% when in about pH 6.5 potassium phosphate buffer, about 82% to about 106% when in about pH 6.5 potassium phosphate buffer, about 70% to about 102% when in about pH 5.5 histidine buffer, and about 65% to about 102% when in about pH 6.5 histidine buffer (Table 6). Similarly, Clostridial toxin pharmaceutical compositions comprising PVP 17, PEG 3350 and Poloxamer 188 resulted in an effective recovered potency and long-term stability of the Clostridial toxin active ingredient (Table 6).

TABLE 6

Formulations using Botulinum Neurotoxin Complex[a] - Three Excipients

| Excipient 1 | | Excipient 2 | | Excipient 3 | | | | Recovered Potency[b] (%) | | | | |
| | | | | | | | | | | | Ambient Temperatrue[c] | | Below Frerezing Temperature[d] | |
| Type | Amount (mg) | Type | Amount (mg) | Type | Amount (mg) | Ratio | Solution (pH) | Initial | 3 months | 12 months | 3 months | 12 months |
| --- | --- | --- | --- | --- | --- | --- | --- | --- | --- | --- | --- | --- |
| Sucrose | 30 | PVP 17 | 30 | Poloxamer 188 | 3 | 10:10:1 | Water (pH 4.2) | 75 | — | — | 79 | 62 |
| Sucrose | 15 | PVP 17 | 15 | Poloxamer 188 | 1.5 | 10:10:1 | Water (pH 4.6) | 82 | 0 | 0 | 70 | 70 |
| Sucrose | 27.5 | PVP 17 | 27.5 | Poloxamer 188 | 5.5 | 5:5:1 | Water (pH 4.2) | 66 | 0 | 0 | 65 | 65 |
| Sucrose | 13.5 | PVP 17 | 13.5 | Poloxamer 188 | 2.7 | 5:5:1 | Water (pH 4.2) | 82 | 0 | 0 | 76 | 76 |
| Sucrose | 20 | PVP 17 | 10 | Poloxamer 188 | 5 | 4:2:1 | Water (pH 4.5) | 104 | 59 | 55 | 110 | 113 |
| Sucrose | 20 | PVP 17 | 20 | Poloxamer 188 | 10 | 2:2:1 | Water (pH 4.4) | 102 | 49 | 0 | 96 | 103 |
| Sucrose | 24 | PVP 17 | 24 | Poloxamer 188 | 12 | 2:2:1 | Water (pH 4.4) | 88 | 0 | 0 | 62 | 61 |
| Sucrose | 12 | PVP 17 | 12 | Poloxamer 188 | 6 | 2:2:1 | Water (pH 4.4) | 88 | 0 | 0 | 65 | 80 |
| Sucrose | 30 | PVP 17 | 15 | Poloxamer 188 | 15 | 2:1:1 | Water (pH 4.3) | 80 | 0 | 0 | 115 | 91 |
| Sucrose | 15 | PVP 17 | 30 | Poloxamer 188 | 15 | 1:2:1 | Water (pH 4.3) | 89 | — | — | 84 | 88 |
| Sucrose | 20 | PVP 17 | 20 | Poloxamer 188 | 20 | 1:1:1 | Water (pH 4.6) | 81 | 0 | 0 | 81 | 85 |
| Sucrose | 10 | PVP 17 | 10 | Poloxamer 188 | 10 | 1:1:1 | Water (pH 4.6) | 102 | 46 | 0 | 79 | 92 |
| Sucrose | 12 | PVP 17 | 24 | Poloxamer 188 | 24 | 1:2:2 | Water (pH 4.8) | 104 | 0 | 0 | 82 | 92 |
| Sucrose | 10 | PVP 17 | 20 | Poloxamer 188 | 30 | 1:2:3 | Water (pH 5.0) | 97 | 49 | 0 | 102 | 95 |
| Sucrose | 20 | PVP 17 | 10 | Poloxamer 188 | 5 | 4:2:1 | 10 mM SC (pH 5.5) | 83 | 51 | 49 | 73 | 89 |
| Sucrose | 20 | PVP 17 | 10 | Poloxamer 188 | 5 | 4:2:1 | 10 mM SC (pH 6.5) | 101 | 52 | 41 | 101 | 103 |
| Sucrose | 20 | PVP 17 | 10 | Poloxamer 188 | 5 | 4:2:1 | 10 mM PP (pH 5.5) | 85 | 68 | 41 | 115 | 101 |
| Sucrose | 20 | PVP 17 | 10 | Poloxamer 188 | 5 | 4:2:1 | 10 mM PP (pH 6.5) | 89 | 69 | 38 | 103 | 101 |
| Sucrose | 20 | PVP 17 | 20 | Poloxamer 188 | 10 | 2:2:1 | 10 mM SC (pH 5.5) | 83 | 51 | 0 | 97 | 91 |
| Sucrose | 20 | PVP 17 | 20 | Poloxamer 188 | 10 | 2:2:1 | 10 mM SC (pH 6.5) | 100 | 0 | 0 | 87 | 113 |
| Sucrose | 20 | PVP 17 | 20 | Poloxamer 188 | 10 | 2:2:1 | 10 mM PP (pH 5.5) | 93 | 58 | 41 | 110 | 99 |
| Sucrose | 20 | PVP 17 | 20 | Poloxamer 188 | 10 | 2:2:1 | 10 mM PP (pH 6.5) | 63 | 55 | 0 | 57 | 89 |
| Sucrose | 15 | PVP 17 | 30 | Poloxamer 188 | 15 | 1:2:1 | 10 mM SC (pH 5.5) | 106 | 58 | 0 | 103 | 101 |
| Sucrose | 20 | PVP 17 | 20 | Poloxamer 188 | 20 | 1:1:1 | 10 mM SC (pH 5.5) | 96 | — | — | 95 | 91 |
| Sucrose | 12 | PVP 17 | 24 | Poloxamer 188 | 24 | 1:2:2 | 10 mM SC (pH 5.5) | 104 | 65 | 0 | 100 | 105 |
| Sucrose | 10 | PVP 17 | 20 | Poloxamer 188 | 30 | 1:2:3 | 10 mM SC (pH 5.5) | 108 | 63 | 0 | 107 | 96 |
| Sucrose | 14 | PVP 17 | 14 | Poloxamer 188 | 1.4 | 10:10:1 | 10 mM NaCl (pH 4.1) | 92 | 0 | 0 | 88 | 75 |
| Sucrose | 27.5 | PVP 17 | 27.5 | Poloxamer 188 | 5.5 | 5:5:1 | 10 mM NaCl (pH 4.2) | 92 | 0 | 0 | 75 | 75 |
| Sucrose | 13.75 | PVP 17 | 13.75 | Poloxamer 188 | 2.75 | 5:5:1 | 10 mM NaCl (pH 4.2) | 88 | 0 | 0 | 78 | 92 |
| Sucrose | 20 | PVP 17 | 10 | Poloxamer 188 | 5 | 4:2:1 | 10 mM NaCl (pH 4.5) | 107 | 59 | 51 | 115 | 113 |
| Sucrose | 20 | PVP 17 | 20 | Poloxamer 188 | 10 | 2:2:1 | 10 mM NaCl (pH 4.4) | 103 | 49 | 0 | 103 | 117 |
| Sucrose | 24 | PVP 17 | 24 | Poloxamer 188 | 12 | 2:2:1 | 10 mM NaCl (pH 4.3) | 82 | 0 | 0 | 85 | 72 |
| Sucrose | 12 | PVP 17 | 12 | Poloxamer 188 | 6 | 2:2:1 | 10 mM NaCl (pH 4.4) | 80 | 0 | 0 | 75 | 84 |
| Sucrose | 20 | PVP 17 | 20 | Poloxamer 188 | 20 | 1:1:1 | 10 mM NaCl (pH 4.5) | 82 | 0 | 0 | 92 | 92 |
| Sucrose | 10 | PVP 17 | 10 | Poloxamer 188 | 10 | 1:1:1 | 10 mM NaCl (pH 4.6) | 92 | 50 | 52 | 83 | 92 |
| Sucrose | 20 | Lactose | 20 | Poloxamer 188 | 10 | 2:2:1 | Water (pH 5.5) | 89 | 84 | 67 | 102 | 108 |

TABLE 6-continued

Formulations using Botulinum Neurotoxin Complex[a] - Three Excipients

| Excipient 1 | | Excipient 2 | | Excipient 3 | | | | Recovered Potency[b] (%) | | | | |
| --- | --- | --- | --- | --- | --- | --- | --- | --- | --- | --- | --- | --- |
| | | | | | | | | | Ambient Temperatrue[c] | | Below Frerezing Temperature[d] | |
| Type | Amount (mg) | Type | Amount (mg) | Type | Amount (mg) | Ratio | Solution (pH) | Initial | 3 months | 12 months | 3 months | 12 months |
| Sucrose | 20 | Lactose | 20 | Poloxamer 188 | 10 | 2:2:1 | 10 mM SC (pH 5.5) | 88 | 85 | 67 | 87 | 91 |
| Sucrose | 20 | Lactose | 20 | Poloxamer 188 | 10 | 2:2:1 | 10 mM SC (pH 6.5) | 99 | 65 | 65 | 77 | 117 |
| Sucrose | 20 | Lactose | 20 | Poloxamer 188 | 10 | 2:2:1 | 10 mM PP (pH 5.5) | 114 | 87 | 73 | 115 | 115 |
| Sucrose | 20 | Lactose | 20 | Poloxamer 188 | 10 | 2:2:1 | 10 mM PP (pH 6.5) | 89 | 101 | 58 | 101 | 114 |
| Sucrose | 20 | Lactose | 20 | Poloxamer 188 | 10 | 2:2:1 | 10 mM NaCl (pH 5.4) | 81 | 101 | 65 | 115 | 101 |
| Sucrose | 25 | Glycine | 25 | Poloxamer 188 | 5 | 5:5:1 | Water (pH 6.1) | 93 | 82 | 82 | 80 | 80 |
| Sucrose | 13.75 | Glycine | 13.75 | Poloxamer 188 | 2.75 | 5:5:1 | Water (pH 6.1) | 92 | — | — | 95 | 95 |
| Sucrose | 10 | PVP 17 | 10 | PEG 3350 | 10 | 1:1:1 | Water (pH 4.9) | 88 | 53 | 53 | 72 | 72 |
| Sucrose | 5 | PVP 17 | 5 | PEG 3350 | 5 | 1:1:1 | Water (pH 4.9) | 102 | 61 | 46 | 82 | 82 |
| Sucrose | 10 | PVP 17 | 20 | PEG 3350 | 10 | 1:2:1 | Water (pH 4.6) | 92 | 0 | 0 | 62 | 62 |
| Sucrose | 5 | PVP 17 | 10 | PEG 3350 | 5 | 1:2:1 | Water (pH 4.6) | 96 | 61 | 0 | 100 | 80 |
| Sucrose | 2.5 | PVP 17 | 5 | PEG 3350 | 2.5 | 1:2:1 | Water (pH 5.0) | 82 | 0 | 0 | 82 | 82 |
| Lactose | 40 | PEG 3550 | 10 | Poloxamer 188 | 10 | 4:1:1 | Water (pH 5.6) | 91 | 59 | 0 | 110 | 102 |
| Lactose | 40 | PEG 3550 | 10 | Poloxamer 188 | 10 | 4:1:1 | 10 mM SC (pH 5.5) | 95 | 60 | 64 | 104 | 95 |
| Dextran 3K | 30 | PEG 3550 | 30 | Poloxamer 188 | 3 | 10:10:1 | Water (pH 6.6) | 82 | 0 | 0 | 82 | 92 |
| Dextran 3K | 50 | PEG 3550 | 5 | Poloxamer 188 | 5 | 5:1:1 | Water (pH 6.2) | 90 | 0 | 0 | 75 | 82 |
| Dextran 3K | 5 | PEG 3550 | 50 | Poloxamer 188 | 5 | 1:5:1 | Water (pH 6.9) | 81 | 0 | 0 | 62 | 62 |
| Dextran 3K | 20 | PEG 3550 | 20 | Poloxamer 188 | 20 | 1:1:1 | Water (pH 6.8) | 104 | 0 | 0 | 0 | 0 |
| Dextran 3K | 30 | PEG 3550 | 30 | Poloxamer 188 | 3 | 10:10:1 | 10 mM SC (pH 5.5) | 102 | 0 | 0 | 67 | 104 |
| Dextran 3K | 50 | PEG 3550 | 5 | Poloxamer 188 | 5 | 5:1:1 | 10 mM SC (pH 5.5) | 92 | 0 | 0 | 92 | 92 |
| Dextran 3K | 5 | PEG 3550 | 50 | Poloxamer 188 | 5 | 1:5:1 | 10 mM SC (pH 5.5) | 88 | 0 | 0 | 88 | 80 |
| Dextran 3K | 20 | PEG 3550 | 20 | Poloxamer 188 | 20 | 1:1:1 | 10 mM SC (pH 5.5) | 106 | 0 | 0 | 82 | 92 |
| Dextran 3K | 30 | PEG 3550 | 30 | Poloxamer 188 | 3 | 10:10:1 | 10 mM SC (pH 6.5) | 79 | 0 | 0 | 88 | 88 |
| Dextran 3K | 50 | PEG 3550 | 5 | Poloxamer 188 | 5 | 5:1:1 | 10 mM SC (pH 6.5) | 96 | 0 | 0 | 88 | 98 |
| Dextran 3K | 5 | PEG 3550 | 50 | Poloxamer 188 | 5 | 1:5:1 | 10 mM SC (pH 6.5) | 76 | 0 | 0 | 92 | 92 |
| Dextran 3K | 20 | PEG 3550 | 20 | Poloxamer 188 | 20 | 1:1:1 | 10 mM SC (pH 6.5) | 95 | 0 | 0 | 102 | 87 |
| Dextran 3K | 30 | PEG 3550 | 30 | Poloxamer 188 | 3 | 10:10:1 | 10 mM PP (pH 5.5) | 92 | 0 | 0 | 104 | 82 |
| Dextran 3K | 50 | PEG 3550 | 5 | Poloxamer 188 | 5 | 5:1:1 | 10 mM PP (pH 5.5) | 92 | 0 | 0 | 96 | 82 |
| Dextran 3K | 5 | PEG 3550 | 50 | Poloxamer 188 | 5 | 1:5:1 | 10 mM PP (pH 5.5) | 96 | 0 | 0 | 82 | 104 |
| Dextran 3K | 20 | PEG 3550 | 20 | Poloxamer 188 | 20 | 1:1:1 | 10 mM PP (pH 5.5) | 87 | 0 | 0 | 92 | 104 |
| Dextran 3K | 30 | PEG 3550 | 30 | Poloxamer 188 | 3 | 10:10:1 | 10 mM PP (pH 6.5) | 96 | 0 | 0 | 96 | 88 |
| Dextran 3K | 50 | PEG 3550 | 5 | Poloxamer 188 | 5 | 5:1:1 | 10 mM PP (pH 6.5) | 100 | 0 | 0 | 104 | 102 |
| Dextran 3K | 5 | PEG 3550 | 50 | Poloxamer 188 | 5 | 1:5:1 | 10 mM PP (pH 6.5) | 106 | 0 | 0 | 98 | 82 |
| Dextran 3K | 20 | PEG 3550 | 20 | Poloxamer 188 | 20 | 1:1:1 | 10 mM PP (pH 6.5) | 82 | 0 | 0 | 106 | 104 |
| Dextran 3K | 30 | PEG 3550 | 30 | Poloxamer 188 | 3 | 10:10:1 | 10 mM HB (pH 5.5) | 70 | 0 | 0 | 92 | 0 |
| Dextran 3K | 50 | PEG 3550 | 5 | Poloxamer 188 | 5 | 5:1:1 | 10 mM HB (pH 5.5) | 90 | 53 | 0 | 86 | 102 |
| Dextran 3K | 5 | PEG 3550 | 50 | Poloxamer 188 | 5 | 1:5:1 | 10 mM HB (pH 5.5) | 102 | 46 | 0 | 82 | 76 |
| Dextran 3K | 20 | PEG 3550 | 20 | Poloxamer 188 | 20 | 1:1:1 | 10 mM HB (pH 5.5) | 75 | 46 | 0 | 92 | 68 |
| Dextran 3K | 30 | PEG 3550 | 30 | Poloxamer 188 | 3 | 10:10:1 | 10 mM HB (pH 6.5) | 87 | 0 | 0 | 102 | 86 |
| Dextran 3K | 50 | PEG 3550 | 5 | Poloxamer 188 | 5 | 5:1:1 | 10 mM HB (pH 6.5) | 92 | 0 | 0 | 84 | 90 |
| Dextran 3K | 5 | PEG 3550 | 50 | Poloxamer 188 | 5 | 1:5:1 | 10 mM HB (pH 6.5) | 102 | 0 | 0 | 106 | 61 |
| Dextran 3K | 20 | PEG 3550 | 20 | Poloxamer 188 | 20 | 1:1:1 | 10 mM HB (pH 6.5) | 65 | 0 | 0 | 96 | 78 |
| PVP 17 | 30 | PEG 3550 | 30 | Poloxamer 188 | 3 | 10:10:1 | Water (pH 5.1) | 66 | 0 | 0 | 58 | 58 |
| PVP 17 | 50 | PEG 3550 | 5 | Poloxamer 188 | 5 | 5:1:1 | Water (pH 4.2) | 82 | 0 | 0 | 70 | 70 |
| PVP 17 | 5 | PEG 3550 | 50 | Poloxamer 188 | 5 | 1:5:1 | Water (pH 6.6) | 0 | 0 | 0 | 0 | 0 |
| PVP 17 | 20 | PEG 3550 | 20 | Poloxamer 188 | 20 | 1:1:1 | Water (pH 5.4) | 78 | 0 | 0 | 66 | 66 |
| PVP 17 | 30 | PEG 3550 | 30 | Poloxamer 188 | 3 | 10:10:1 | 10 mM SC (pH 5.5) | 82 | 0 | 0 | 62 | 62 |
| PVP 17 | 50 | PEG 3550 | 5 | Poloxamer 188 | 5 | 5:1:1 | 10 mM SC (pH 5.5) | 88 | 0 | 0 | 78 | 78 |
| PVP 17 | 5 | PEG 3550 | 50 | Poloxamer 188 | 5 | 1:5:1 | 10 mM SC (pH 5.5) | 96 | 0 | 0 | 96 | 96 |
| PVP 17 | 20 | PEG 3550 | 20 | Poloxamer 188 | 20 | 1:1:1 | 10 mM SC (pH 5.5) | 82 | 0 | 0 | 100 | 100 |
| PVP 17 | 30 | PEG 3550 | 30 | Poloxamer 188 | 3 | 10:10:1 | 10 mM SC (pH 6.5) | — | — | — | — | — |
| PVP 17 | 50 | PEG 3550 | 5 | Poloxamer 188 | 5 | 5:1:1 | 10 mM SC (pH 6.5) | — | — | — | — | — |
| PVP 17 | 5 | PEG 3550 | 50 | Poloxamer 188 | 5 | 1:5:1 | 10 mM SC (pH 6.5) | — | — | — | — | — |
| PVP 17 | 20 | PEG 3550 | 20 | Poloxamer 188 | 20 | 1:1:1 | 10 mM SC (pH 6.5) | — | — | — | — | — |
| PVP 17 | 30 | PEG 3550 | 30 | Poloxamer 188 | 3 | 10:10:1 | 10 mM PP (pH 5.5) | — | — | — | — | — |
| PVP 17 | 50 | PEG 3550 | 5 | Poloxamer 188 | 5 | 5:1:1 | 10 mM PP (pH 5.5) | — | — | — | — | — |
| PVP 17 | 5 | PEG 3550 | 50 | Poloxamer 188 | 5 | 1:5:1 | 10 mM PP (pH 5.5) | — | — | — | — | — |
| PVP 17 | 20 | PEG 3550 | 20 | Poloxamer 188 | 20 | 1:1:1 | 10 mM PP (pH 5.5) | — | — | — | — | — |
| PVP 17 | 30 | PEG 3550 | 30 | Poloxamer 188 | 3 | 10:10:1 | 10 mM PP (pH 6.5) | — | — | — | — | — |
| PVP 17 | 50 | PEG 3550 | 5 | Poloxamer 188 | 5 | 5:1:1 | 10 mM PP (pH 6.5) | — | — | — | — | — |
| PVP 17 | 5 | PEG 3550 | 50 | Poloxamer 188 | 5 | 1:5:1 | 10 mM PP (pH 6.5) | — | — | — | — | — |
| PVP 17 | 20 | PEG 3550 | 20 | Poloxamer 188 | 20 | 1:1:1 | 10 mM PP (pH 6.5) | — | — | — | — | — |
| PVP 17 | 30 | PEG 3550 | 30 | Poloxamer 188 | 3 | 10:10:1 | 10 mM HB (pH 5.5) | 78 | 0 | 0 | 54 | 54 |
| PVP 17 | 50 | PEG 3550 | 5 | Poloxamer 188 | 5 | 5:1:1 | 10 mM HB (pH 5.5) | 92 | 0 | 0 | 88 | 88 |
| PVP 17 | 5 | PEG 3550 | 50 | Poloxamer 188 | 5 | 1:5:1 | 10 mM HB (pH 5.5) | 106 | 70 | 70 | 82 | 82 |
| PVP 17 | 20 | PEG 3550 | 20 | Poloxamer 188 | 20 | 1:1:1 | 10 mM HB (pH 5.5) | 102 | 0 | 0 | 64 | 64 |
| PVP 17 | 30 | PEG 3550 | 30 | Poloxamer 188 | 3 | 10:10:1 | 10 mM HB (pH 6.5) | 95 | 0 | 0 | 92 | 92 |
| PVP 17 | 50 | PEG 3550 | 5 | Poloxamer 188 | 5 | 5:1:1 | 10 mM HB (pH 6.5) | 106 | 50 | 50 | 96 | 96 |
| PVP 17 | 5 | PEG 3550 | 50 | Poloxamer 188 | 5 | 1:5:1 | 10 mM HB (pH 6.5) | 104 | 46 | 46 | 91 | 91 |
| PVP 17 | 20 | PEG 3550 | 20 | Poloxamer 188 | 20 | 1:1:1 | 10 mM HB (pH 6.5) | 110 | 53 | 53 | 104 | 104 |

TABLE 6-continued

Formulations using Botulinum Neurotoxin Complex[a] - Three Excipients

| Excipient 1 | | Excipient 2 | | Excipient 3 | | | | Recovered Potency[b] (%) | | | |
|---|---|---|---|---|---|---|---|---|---|---|---|
| | | | | | | | | Initial | Ambient Temperatrue[c] | | Below Frerezing Temperature[d] |
| Type | Amount (mg) | Type | Amount (mg) | Type | Amount (mg) | Ratio | Solution (pH) | | 3 months | 12 months | 3 months | 12 months |
| PVP 17 | 25 | Glycine | 25 | Poloxamer 188 | 5 | 5:5:1 | Water (pH 5.6) | 79 | 0 | 0 | 78 | 78 |
| PVP 17 | 13.75 | Glycine | 13.75 | Poloxamer 188 | 2.75 | 5:5:1 | Water (pH 5.6) | 83 | — | — | 62 | 63 |

[a]Amount of botulinum neurotoxin serotype A complex added per formulation was 150 units. Total volume of formulation was 1.0 mL.
[b]Recovery is expressed as a percentage and is calculated by dividing the potency of the active ingredient determined after reconstitution divided by the potency of the active ingredient determined before addition to the formulation. 3 months refers to the length of time a formulation was minimally stored at the indicated temperature. 12 months refers to the length of time a formulation was minimally stored at the indicated temperature.
[c]Ambient temperature is between about 18° C. to about 22° C.
[d]Below freezing temperature is between about −5° C. to about −20° C.

Example 4

Non-Protein Stabilized Formulations—150 kDa Clostridial Toxin

Experiments were carried out to prepare multiple formulations where the Clostridial toxin active ingredient contained in the formulations was a 150-kDa Clostridial toxin (Table 7). The non-protein excipients tested were added separately or in combination with the listed buffers or salts (Table 7). All of the formulations were compounded, lyophilized, reconstituted and potency assessed in the same manner, and with the same Clostridial toxin active ingredient used in each formulation, except that each formulation was prepared with different non-protein excipients or with different amounts of the non-protein excipients.

The tested formulations were compounded, processed, stored and reconstituted as described in Example 1, except that the Clostridial toxin active ingredient added was about 150 units of a 150 kDa BoNT/A. Recovered potency was determined using the mouse $LD_{50}$ bioassay described in Example 1. Recovery is expressed as a percentage and is calculated by dividing the potency of the Clostridial toxin active ingredient in the stored reconstitution formulation by the potency of the active Clostridial toxin ingredient determined prior to its addition into the test solution. The results show that a Clostridial toxin pharmaceutical composition comprising a 150-kDa Clostridial toxin could be stabilized when the formulation comprised two or more non-protein excipients (Table 7).

Clostridial toxin pharmaceutical compositions comprising a sugar and a surfactant resulted in an effective initial recovered potency of the Clostridial toxin active ingredient. For example, both sucrose alone and Poloxamer 188 alone resulted in no detectable recovered potency of a Clostridial toxin active ingredient (Table 7). Surprisingly Clostridial toxin pharmaceutical compositions comprising sucrose in combination with Poloxamer 188 resulted in recovered potency of the Clostridial toxin active ingredient of about 113% (Table 7). These findings regarding 150 kDa BoNT/A are similar to the synergistic recovery observed with the 900-kDa BoNT/A toxin complex in Examples 1-3, where Clostridial toxin pharmaceutical compositions comprising sucrose in combination with Poloxamer 188 resulted in 99% initial recovered potency (Table 3).

Clostridial toxin pharmaceutical compositions comprising lactose and/or Poloxamer 188 yielded mixed results as those seen with the 900-Kda BoNT/A toxin complex in Examples 1-3. For example, pharmaceutical compositions comprising lactose as the sole excipient did not result in any detectable recovered potency of the Clostridial toxin active ingredient (150 kDa BoNT/A) (Table 7). This lack of recovery was unexpected given the finding of recovered potency of about 35% for pharmaceutical compositions comprising lactose as the sole excipient when the Clostridial toxin active ingredient was the 900-kDa BoNT/A toxin complex (Table 2). Clostridial toxin pharmaceutical compositions comprising Poloxamer 188 as the sole excipient resulted in no detectable recovered potency of a Clostridial toxin active ingredient (Table 7), a finding similar to those discussed in Example 1. More strikingly, Clostridial toxin pharmaceutical compositions comprising lactose and Poloxamer 188 as excipients resulted in an initial recovered potency of about 110% (Table 7). Thus, like the 900-kDa BoNT/A toxin complex, there is a synergistic recovery of the 150 kDa BoNT/A in pharmaceutical compositions comprising lactose and Poloxamer 188.

Clostridial toxin pharmaceutical compositions comprising two non-protein polymers also resulted in an effective initial recovered potency of the Clostridial toxin active ingredient. For example, Clostridial toxin pharmaceutical compositions comprising Dextran 40K and/or Poloxamer 188 also yielded comparable results as those seen with the 900-kDa BoNT/A toxin complex in Examples 1-3. For example, recovery of the 150 kDa BoNT/A was observed in pharmaceutical compositions comprising Dextran 40K and Poloxamer 188, although the initial recovered potency was lower for the 150 kDa BoNT/A (compare about 50% initial recovered potency of the 150 kDa BoNT/A in Table 7 versus about 85% initial recovered potency of the 900-kDa BoNT/A toxin complex in Table 4).

Clostridial toxin pharmaceutical compositions comprising PEG 3350 and/or Poloxamer 188 yielded somewhat different results as those seen with the 900-kDa BoNT/A toxin complex in Examples 1-3. For example, initial recovery potency of about 47% of the 150 kDa BoNT/A was observed in pharmaceutical compositions comprising PEG 3350 and Poloxamer 188 (Table 7). This recovery was unexpected given the finding that no recovered potency was detected for pharmaceutical compositions comprising PEG 3350 and Poloxamer 188 when the Clostridial toxin active ingredient was the 900-kDa BoNT/A toxin complex (Table 4). However, Clostridial toxin pharmaceutical compositions comprising PEG 3350 and/or Poloxamer 188 in about pH 5.5 sodium citrate buffer yielded comparable results as those seen with the 900-kDa BoNT/A toxin complex in Examples 1-3. For example, recovery of the 150 kDa BoNT/A was observed in pharmaceutical compositions comprising PEG 3350 and/or Poloxamer 188 in about pH 5.5 sodium citrate buffer, although the initial recovered potency was lower for the 150 kDa BoNT/A (compare about 52% initial recovered potency of the 150 kDa BoNT/A in Table 7 versus about 90% initial recovered potency of the 900-kDa BoNT/A toxin complex in Table 4). Similarly, recovery of the 150 kDa BoNT/A was observed in pharmaceutical compositions comprising PEG 3350 and/or Poloxamer 188 in about pH 5.5 potassium phosphate buffer, although the initial recovered potency was lower for the 150 kDa BoNT/A (compare about 53% initial recovered potency of the 150 kDa BoNT/A in Table 7 versus about 98% initial recovered potency of the 900-kDa BoNT/A toxin complex in Table 4).

Clostridial Toxin Target Cells, U.S. patent application Ser. No. 11/776,075 (Jul. 11, 2007); Dolly, J. O. et al., Activatable Clostridial Toxins, U.S. patent application Ser. No. 11/829,475 (Jul. 27, 2007); Foster, K. A. et al., Fusion Proteins, International Patent Publication WO 2006/059093 (Jun. 8, 2006); and Foster, K. A. et al., Non-Cytotoxic Protein Conjugates, International Patent Publication WO 2006/059105 (Jun. 8, 2006), each of which is incorporated by reference in its entirety.

To determine the recovered potency of a retargeted Clostridial toxin, the reconstituted formulation was assayed by a in vitro light chain assay. In this assay, the solid formulation is reconstituted in 1.0 mL of digestion buffer

TABLE 7

Formulations using 150 kDa Botulinum Neurotoxin[a]

| Excipient 1 | | Excipient 2 | | | | Recovered |
|---|---|---|---|---|---|---|
| Type | Amount (mg) | Type | Amount (mg) | Ratio | Solution (pH) | Potency[b] (%) |
| Poloxamer 188 | 50 | — | — | — | Water (pH 6.5) | 0 |
| Poloxamer 188 | 20 | — | — | — | Water (pH 6.5) | 0 |
| Sucrose | | — | — | — | Water (pH 6.0) | 0 |
| Sucrose | 60 | Poloxamer 188 | 6 | 10:1 | Water (pH 6.5) | 113 |
| Lactose | 60 | — | — | — | Water (pH 4.4) | 0 |
| Lactose | 60 | Poloxamer 188 | 6 | 10:1 | Water (pH 4.7) | 110 |
| Dextran 40K | 60 | — | — | — | Water (pH 5.0) | 0 |
| Dextran 40K | 60 | Poloxamer 188 | 6 | 10:1 | Water (pH 5.8) | 50 |
| Dextran 40K | 60 | Poloxamer 188 | 6 | 10:1 | 10 mM SC (pH 5.5) | 46 |
| Dextran 40K | 60 | Poloxamer 188 | 6 | 10:1 | 10 mM SC (pH 7.2) | 0 |
| Dextran 40K | 60 | Poloxamer 188 | 6 | 10:1 | 10 mM PP (pH 5.5) | 49 |
| Dextran 40K | 60 | Poloxamer 188 | 6 | 10:1 | 10 mM PP (pH 7.2) | 50 |
| PEG 3350 | 60 | — | — | — | Water (pH 6.6) | 0 |
| PEG 3350 | 60 | — | — | — | 10 mM SC (pH 5.5) | 0 |
| PEG 3350 | 60 | — | — | — | 10 mM PP (pH 5.5) | 0 |
| PEG 3350 | 60 | Poloxamer 188 | 6 | 10:1 | Water (pH 6.8) | 47 |
| PEG 3350 | 60 | Poloxamer 188 | 6 | 10:1 | 10 mM SC (pH 5.5) | 52 |
| PEG 3350 | 60 | Poloxamer 188 | 6 | 10:1 | 10 mM SC (pH 7.2) | 0 |
| PEG 3350 | 60 | Poloxamer 188 | 6 | 10:1 | 10 mM PP (pH 5.5) | 53 |
| PEG 3350 | 60 | Poloxamer 188 | 6 | 10:1 | 10 mM PP (pH 7.2) | 0 |

[a]Amount of 150 kDa botulinum neurotoxin serotype A added per formulation was 150 units. Total volume of formulation was 1.0 mL.
[b]Recovery is expressed as a percentage and is calculated by dividing the potency of the active ingredient determined after reconstitution divided by the potency of the active ingredient determined before addition to the formulation.

Example 5

Non-Protein Stabilized Formulations—Re-Targeted Clostridial Toxin

Experiments were carried out to prepare multiple formulations where the Clostridial toxin active ingredient contained in the formulations was a re-targeted Clostridial toxin (Table 8). The non-protein excipients tested were added separately or in combination with the listed buffers or salts (Table 6). All of the formulations were compounded, lyophilized, reconstituted and potency assessed in the same manner, and with the same Clostridial toxin active ingredient used in each formulation, except that each formulation was prepared with different non-protein excipients or with different amounts of the non-protein excipients.

The tested formulations were compounded, processed, stored and reconstituted as described in Example 1, except that the Clostridial toxin active ingredient added was about 250 ng of a 100 kDa re-targeted BoNT/A, where the modification was the substitution of the BoNT/A binding domain with an opioid ligand, see e.g., Steward, L. E. et al., Modified Clostridial Toxins with Enhanced Translocation Capabilities and Altered Targeting Activity For Non-Clostridial Toxin Target Cells, U.S. patent application Ser.

comprising 2 mM DTT, 300 µM ZnCl$_2$, and 50 mM HEPES (pH 7.4) and incubated at 37° C. for 30 minutes. After the incubation, 500 µL the incubated formulation is transferred to a new tube and 5.0 µL of 200 µM of a quench-release fluorescent substrate (SNAPTIDE® 520) was added. This mixture is incubated at 30° C. for about 18 to about 20 hours to allow for the Clostridial toxin active ingredient to digest the quench-release fluorescent substrate. The reaction is stopped by adding 25 µL of 5% TFA to the digestion mixture. The quenched digestion mixture was then analyzed by routine reversed-phase high performance liquid chromatography (RP-HPLC) methods to separate and measure the amount of quench-release fluorescent substrate cleaved by the reconstituted formulation. For this RP-HPLC analysis, the quenched digestion mixture was transferred to HPLC vials and 25 µL of this mixture was injected into the column (Waters SYMMETRY 300™ C18, 3.5 µm, 4.6×150 mm) set at a flow rate of 1.0 mL/min and a column temperature of 35° C. The run time was 20 minutes with a 5 minute injection delay. The gradient mobile phase was Solution A, comprising 0.1% TFA in water, and Solution B, comprising 0.1% TFA in acetonitrile. The gradient program was as follows: 0-10 minutes 90% A and 10% B, 10-15 minutes 80% A and 20% B, and 15-20 minutes 100% B. The multi-wavelength fluorescent detector was set to an excitation wavelength of 322 nm and an emission wavelength of 420 nm and data was collected and analyzed using standard software. Cleavage products were identified by retention time using fluorescent detections and quantitated by peak area. Cleaved quench-release fluorescent substrate typically eluted at a retention time of 5.7 minutes.

Recovery is expressed as a percentage and is calculated by dividing the potency of the Clostridial toxin active ingredient in the stored reconstitution formulation by the potency of the active Clostridial toxin ingredient determined prior to its addition into the test solution. Clostridial toxin pharmaceutical composition comprising a re-targeted Clostridial toxin could be stabilized when the formulation comprised two or more non-protein excipients in a manner similar to the 900-kDa BoNT/A toxin complex and the 150 kDa BoNT/A.

The results showed that a Clostridial toxin pharmaceutical compositions comprising a sugar and a surfactant resulted in an effective initial recovered potency of the Clostridial toxin active ingredient. For example, Clostridial toxin pharmaceutical compositions comprising sucrose or lactose in combination with Poloxamer 188 resulted in recovered potency of the re-targeted Clostridial toxin similar to the results observed with the 900-kDa BoNT/A toxin complex (see Examples 1-3) and the 150 kDa BoNT/A (Example 4).

The results also showed that a Clostridial toxin pharmaceutical compositions comprising a non-protein polymer and a surfactant also resulted in an effective initial recovered potency of the Clostridial toxin active ingredient. For example, Clostridial toxin pharmaceutical compositions comprising Dextran 40K or PEG 3550 in combination with Poloxamer 188 resulted in recovered potency of the re-targeted Clostridial toxin similar to the results observed with the 900-kDa BoNT/A toxin complex (see Examples 1-3) and the 150 kDa BoNT/A (Example 4).

What is claimed:

1. An animal protein free method to stabilize a serotype A Clostridial botulinum neurotoxin, comprising:
    (a) compounding an aqueous carrier with two or more non-animal derived non-protein excipients and a biologically active serotype A Clostridial botulinum neurotoxin to form a compounded formulation; and
    (b) lyophilizing or vacuum-drying the compounded formulation to thereby provide a stable powdered formulation;
wherein:
    the two or more non-animal derived non-protein excipients comprise (i) a surfactant and (ii) a disaccharide selected from the group consisting of trehalose and sucrose;
    the powdered formulation retains an initial potency of at least about 50% of the theoretical maximum potency of the botulinum toxin after reconstitution with normal saline or water;
    the powdered formulation has a pH from about 5 to about 7.3 after reconstitution with normal saline or water;
    the powdered formulation is suitable for intramuscular or subcutaneous administration after reconstitution with normal saline or water; and
    the powdered formulation is animal protein free and polysaccharide free.

2. The method of claim 1, wherein the compounded formulation further comprises a buffer.

3. The method of claim 1, wherein the surfactant is poloxamer.

4. The method of claim 1, wherein the pH of the compounded formulation is between about 5.5 and about 6.5.

5. The method of claim 1, wherein the disaccharide is sucrose.

6. The method of claim 1, wherein the disaccharide is trehalose.

7. The method of claim 1, wherein the biologically active serotype A Clostridial botulinum neurotoxin is pure approximately 150 kDa toxin.

8. An animal protein free method to stabilize a serotype A Clostridial botulinum neurotoxin, comprising:
    (a) compounding an aqueous carrier with two or more non-animal derived non-protein excipients and a biologically active serotype A Clostridial botulinum neurotoxin to form a compounded formulation; and
    (b) lyophilizing or vacuum drying the compounded formulation to thereby provide a stable powdered formulation;
wherein:
    the two or more non-animal derived non-protein excipients comprise (i) a surfactant and (ii) a disaccharide selected from the group consisting of trehalose and sucrose present in an amount of between about 5 mg to about 250 mg for each about 150 units of the botulinum neurotoxin;
    the powdered formulation has a pH from about 5 to about 7.3 after reconstitution with normal saline or water;
    the powdered formulation retains an initial potency of at least about 50% of the theoretical maximum potency of the botulinum toxin after reconstitution with normal saline or water;
    the powdered formulation is suitable for intramuscular or subcutaneous administration after reconstitution with normal saline or water; and
    the compounded formulation is animal protein free and polysaccharide free.

9. The method of claim 8, wherein the disaccharide is sucrose.

10. The method of claim 8, wherein the disaccharide is trehalose.

11. The method of claim 8, wherein the surfactant is poloxamer.

12. The method of claim 8, wherein the biologically active serotype A Clostridial botulinum neurotoxin is pure approximately 150 kDa toxin.

13. The method of claim 8, wherein the compounded formulation retains of at least about 50% of the theoretical maximum potency of the botulinum toxin after storage for three months at below freezing temperature.

14. The method of claim 8, wherein the compounded formulation further comprises a polymer.

15. The method of claim 8, wherein the compounded formulation further comprises a buffer.

16. The method of claim 2, wherein the buffer is citrate or phosphate buffer.

17. The method of claim 15, wherein the buffer is citrate or phosphate buffer.

18. The method of claim 8, wherein the pH of the compounded formulation is between about 5.5 and about 6.5.

19. The method of claim 1, wherein the compounded formulation comprises between about 100 units to about 200 units of the botulinum toxin.

20. The method of claim 1, wherein the compounded formulation retains of at least about 50% of the theoretical maximum potency of the botulinum toxin after storage for three months at below freezing temperature.

21. The method of claim 1, wherein the compounded formulation further comprises a polymer.

* * * * *